US012356910B2

(12) United States Patent
Di et al.

(10) Patent No.: US 12,356,910 B2
(45) Date of Patent: Jul. 15, 2025

(54) GENE-EDITED BASIL PLANTS RESISTANT TO DOWNY MILDEW

(71) Applicant: Rutgers, The State University of New Jersey, New Brunswick, NJ (US)

(72) Inventors: Rong Di, East Brunswick, NJ (US); Michael A. Lawton, Highland Park, NJ (US); James E. Simon, Princeton, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 17/914,647

(22) PCT Filed: Mar. 29, 2021

(86) PCT No.: PCT/US2021/024697
§ 371 (c)(1),
(2) Date: Sep. 26, 2022

(87) PCT Pub. No.: WO2021/195630
PCT Pub. Date: Sep. 30, 2021

(65) Prior Publication Data
US 2023/0210073 A1   Jul. 6, 2023

Related U.S. Application Data

(60) Provisional application No. 63/000,586, filed on Mar. 27, 2020.

(51) Int. Cl.
| C12N 9/22 | (2006.01) |
| A01H 1/00 | (2006.01) |
| C12N 15/82 | (2006.01) |

(52) U.S. Cl.
CPC ............. *A01H 1/1255* (2021.01); *C12N 9/22* (2013.01); *C12N 15/8282* (2013.01)

(58) Field of Classification Search
CPC ..... C12N 15/8282; C12N 9/22; A01H 1/1255
See application file for complete search history.

(56) References Cited

U.S. PATENT DOCUMENTS

| 10,159,212 | B1 | 12/2018 | Simon et al. |
| 2009/0170703 | A1 | 7/2009 | Van Den Ackerveken et al. |
| 2010/0058498 | A1 | 3/2010 | Apuya et al. |
| 2014/0141044 | A1 | 5/2014 | Bhatt et al. |
| 2016/0272995 | A1 | 9/2016 | Lee |
| 2016/0298130 | A1 | 10/2016 | Van Damme et al. |
| 2018/0265887 | A1 | 9/2018 | Acosta et al. |
| 2019/0144878 | A1* | 5/2019 | Van Damme ......... C12Y 114/11 800/298 |
| 2019/0348154 | A1 | 11/2019 | Fröse et al. |

FOREIGN PATENT DOCUMENTS

| WO | WO 2019/041034 A1 | 3/2019 |
| WO | WO 2019/068647 A1 | 4/2019 |

OTHER PUBLICATIONS

Zeilmaker et al., 2015, Downy Mildew Resistant 6 and DMR 6-LIKE Oxygenase 1 are partially redundant but distinct suppressors of immunity in *Arabidopsis*. The Plant Journal, 81(2), 210-222. (Year: 2015).*
NCBI Nucleotide GeneBank. Submitted ,Jan. 24, 2020, Ocimum basilicum cultivar *Genoveser* DMR1 gene, complete cds GenBank: MT000722.1 (Year: 2020).*
Navet, N. ,2019, Dissecting the Molecular Basis of Basil-Peronospora Belbahrii Interactions and Genetic Engineering for Disease Resistance (Doctoral dissertation, University of Hawai'i at Manoa). (Year: 2019).*
Navet et al., 2020, Efficient targeted mutagenesis in allotetraploid sweet basil by CRISPR/Cas9. Plant Direct, 4(6), e00233. (Year: 2020).*
Shao et al., 2018, A qPCR approach to quantify the growth of basil downy mildew pathogen Peronospora belbahrii during infection. Current Plant Biology, 15, 2-7. (Year: 2018).*
Damme et al., 2009, Downy mildew resistance in *Arabidopsis* by mutation of Homoserine Kinase. The Plant Cell, 21(7), 2179-2189. (Year: 2009).*
Navet et al. (Published Year: 2019, Publication: Abstracts of Presentations Plant Health 2019, p. S2.22, Paragraph 3, https://doi.org/10.1094/PHYTO-109-10-S2.1), Accessed in https://apsjournals.apsnet.org/doi/10.1094/PHYTO-109-10-S2.1) (Year: 2019).*
Anzalone et al., 2019, Search-and-replace genome editing without double-strand breaks or donor DNA. Nature, 576(7785), 149-157. (Year: 2019).*
Navet'20 et al., 2020, Efficient targeted mutagenesis in allotetraploid sweet basil by CRISPR/Cas9. Plant Direct, 4(6), e00233. (Year: 2020).*
Hua et al., 2019, Genome engineering in rice using Cas9 variants that recognize Ng PAM sequences. Molecular plant, 12(7), 1003-1014. (Year: 2019).*
Fakhr et al., 2016, Precise and efficient siRNA design: a key point in competent gene silencing. Cancer gene therapy, 23(4), 73-82. (Year: 2016).*

(Continued)

*Primary Examiner* — David H Kruse
*Assistant Examiner* — Santosh Sharma
(74) *Attorney, Agent, or Firm* — Klarquist Sparkman, LLP

(57) ABSTRACT

The disclosure provides methods of making gene-edited plants that are resistant to downy mildew, such as plants with reduced expression of homoserine kinase (HSK), 2-oxoglutarate-Fe(II) oxygenase (2OGO), or both. The disclosure further provides methods of making gene-edited modified plants that are cold tolerant, such as plants with reduced expression of MYB14. In some examples, CRISPR/Cas methods are used, wherein the plants include a mutated HSK, 2OGO, and/or MYB14 gene resulting in reduced expression and/or gene activity. Plants generated using the methods are provided. Such plants can include other desirable traits. HSK, 2OGO, and/or MYB14 nucleic acid and protein molecules are provided, as are gRNAs specific for HSK, 2OGO, or MYB14 and vectors containing such.

17 Claims, 18 Drawing Sheets

Specification includes a Sequence Listing.

(56) References Cited

OTHER PUBLICATIONS

APS Annual Meeting, "Fungal and oomycete pathogens: New approaches to disease resistance," Aug. 3-7, 2019, Cleveland, Ohio, Abstract.
Chen et al., AtMYB14 Regulates Cold Tolerance in *Arabidopsis, Plant Mol Biol Report.* 31:87-97, 2013.
Deschamps and Simon, "*Agrobacterium tumefaciens*-mediated transformation of *Ocimum basilicum* and *C. citriodorum,*" *Plant Cell Rep.* 21:359-364, 2002.
International Search Report and Written Opinion mailed on Sep. 14, 2021 in International Application No. PCT/US2021/024697 (12 pages).
Phippen and Simon, "Shoot regeneration of young leaf explants from basil (*Ocimum basilicum* L.)," *In Vitro Cell. Dev. Biol.* 36:250-254, 2000.
Project No. NJ12960 Grant Report, "CRISPR-Editing of Sweet Basil Susceptibility Genes to Improve Downy Mildew Resistance," https://portal.nifa.usda.gov/web/crisprojectpages/1005372-improvement-of-crop-disease-resistance-and-stress-tolerance-by-crisprcas-gene-editing.html, 2018, 3 pages.
Pyne et al., "A rapid screening approach to identify resistance to basil downy mildew (*Peronospora belbahrii*)," *HortSci.* 49:1041-1045, 2014.
Roos, "2014 Basil Downy Mildrew Outbreak Our Worst One Yet," NC State Extension, 2014.
Van Damme et al., "Identification of *Arabidopsis* loci required for susceptibility to the downy mildew pathogen *Hyaloperonospora parasitica*," *Mol Plant Microbe Interact.* 18:583-592, 2005.
Van Damme et al., "*Arabidopsis* DMR6 encodes a putative 2OG-Fe(II) oxygenase that is defense-associated but required for susceptibility to downy mildew," *Plant J.* 54:785-793, 2008.
Van Damme et al., "Downy mildew resistance in *Arabidopsis* by mutation of Homoserine Kinase," *Plant Cell* 21:2179-2189, 2009.
Zeilmaker et al., "Downy Mildew Resistant 6 and DMR6-LIKE Oxygenase 1 are partially redundant but distinct suppressors of immunity in *Arabidopsis,*" *Plant J.* 81:210-2022, 2015.
Zhang et al., "CRISPR-Editing of Sweet Basil (*Ocimum basilicum* L.) Homoserine Kinase Gene for Improved Downy Mildew Disease Resistance," *Front Genome Ed.*, 3:629769, 2021, 8 pages.
Navet and Tian, "Efficient targeted mutagenesis in allotetraploid sweet basil by CRISPR/Cas9," *Plant Direct*, 4(6): e00233, 2020.
Itay Gonda et al., "The genome sequence of tetraploid sweet basil, *Ocimum basilicum* L., provides tools for advanced genome editing and molecular breeding," *DNA Research*, 27(5): 1-10, 2020.

* cited by examiner

FIG. 1

(SEQ ID NOS: 2 and 3)

```
Query    1   MAAVCLKLNFAAAAAASASATTVANLSSP--KPQTHLRFNPSASALSTSAYSK         51
             MA       F            S P         R   S    L
Sbjct    1   MASLC----FQSPSKPISYFQPKSNPSPPLFAKVSVFRCRASVQTLV              43

Query   52   STEPLPVFSSVKSFAPATVANLGPGFDFLGCAVDGIGDYVSLRVDPDVHPGEVSISNITG  111
             + EP PVF SVK+FAPATVANLGPGFDFLGCAVDG+GD+V+LRVDP V  GEVSIS ITG
Sbjct   44   AVEPEPVFVSVKTFAPATVANLGPGFDFLGCAVDGLGDHVTLRVDPSVRAGEVSISEITG  103

Query  112   AGSKLSKNPLWNCAGIAAIAVMKMLSIRSVGLSLSLEKGLPLGSGLGSSAASAAAAAVAV  171
              +KLS NPL NCAGIAAIA MKML IRSVGLSL L KGLPLGSGLGSSAASAAAAAVAV
Sbjct  104   TTTKLSTNPLRNCAGIAAIATMKMLGIRSVGLSLDLHKGLPLGSGLGSSAASAAAAAVAV  163

Query  172   NELFGGPLSPSELVFAGLESEAKVSGYHADNVAPSILGGFVLIRSYDPLELMQLKFPHEK  231
             NE+FG  L   +LV AGLESEAKVSGYHADN+AP I+GGFVLIR+Y+PL+L   L+FP +K
Sbjct  164   NEIFGRKLGSDQLVLAGLESEAKVSGYHADNIAPAIMGGFVLIRNYEPLDLKPLRFPSDK  223

Query  232   SLYFVLVNPEFEAPTKKMRAALPQEITMSHHIWNSSQAGALVASVLQGDLVGLGKALSSD  291
              L+FVLV+P+FEAPTKKMRAALP EI M HH+WNSSQA ALVA+VL+GD V LGKALSSD
Sbjct  224   DLFFVLVSPDFEAPTKKMRAALPTEIPMVHHVWNSSQAAALVAAVLEGDAVMLGKALSSD  283

Query  292   KIVEPKRAPLIPGMEAVKKAAIAAGAFGCTISGAGPTAVAVTDSEEKGREIGEKMVEAFE  351
             KIVEP RAPLIPGMEAVKKAA+  AGAFGCTISGAGPTAVAV DSEEKG+ IGEKMVEAF
Sbjct  284   KIVEPTRAPLIPGMEAVKKAALEAGAFGCTISGAGPTAVAVIDSEEKGQVIGEKMVEAFW  343

Query  352   KEGNLKALAMVRQLDRVGARLVSSVPR    378
             K G+LK++A V++LD VGARLV+SV R
Sbjct  344   KVGHLKSVASVKKLDNVGARLVNSVSR    370
```

FIG. 2

(SEQ ID NOS: 6 and 7)

```
Query   1    METKVIS-GTQFTSLPSCYVRPESERPKLSEVADCEDVPVIDLGCGDRGLIVKQIGDACR   59
             M  K+IS G + T+LP  YVRP S+RP+LSEV+  ED P+IDL   DR +++QI  AC
Sbjct   1    MAAKLISTGFRHTTLPENYVRPISDRPRLSEVSQLEDFPLIDLSSTDRSFLIQQIHQACA   60

Query   60   EYGFFQVINHAVPKDIVDKMVGVAHEFFSLSVEEKMKLYSDDPSKTMRLSTSFNVRKETV   119
              +GFFQVINH V K I+D+MV VA EFFS+S+EEKMKLYSDDP+KT RLSTSFNV+KE V
Sbjct   61   RFGFFQVINHGVNKQIIDEMVSVAREFFSMSMEEKMKLYSDDPTKTTRLSTSFNVKKEEV   120

Query   120  HNWRDYLRLHCYPLEKYAPEWPSNPSSFKDIVSTYCKEVRALGFWLQEAISESLGLHKDC   179
             +NWRDYLRLHCYP+ KY  EWPSNP SFK+IVS Y +EVR +GF ++E ISESLGL KD
Sbjct   121  NNWRDYLRLHCYPIHKYVNEWPSNPPSFKEIVSKYSREVREVGFKIEELISESLGLEKDY   180

Query   180  LKNVLGEQGQHMAINFYPACPEPDLTFGLPAHTDPNALTILLQDLLVSGLQVLKDGKWLA   239
             +K VLGEQGQHMA+N+YP CPEP+LT+GLPAHTDPNALTILLQD  V GLQ+L DG+W A
Sbjct   181  MKKVLGEQGQHMAVNYYPPCPEPELTYGLPAHTDPNALTILLQDTTVCGLQILIDGQWFA   240

Query   240  IKPQPDAFVINIGDQIQAFSNGKYRSVWHRAVVNSNKARLSVASFLCPCDAANISAPNEL   299
             + P PDAFVINIGDQ+QA SNG Y+SVWHRAV N+    RLSVASFLCP D A +S    L
Sbjct   241  VNPHPDAFVINIGDQLQALSNGVYKSVWHRAVTNTENPRLSVASFLCPADCAVMSPAKPL   300

Query   300  TTGDD---RAIYRGFTYAEYYKKFWSRNLDQEHCLELFKN   336
              +D   + +Y+ FTYAEYYKKFWSRNLDQEHCLE F N
Sbjct   301  WEAEDDETKPVYKDFTYAEYYKKFWSRNLDQEHCLENFLN   340
```

FIG. 3

ATGGAAACGAAGGTCATTAGTGGAACACAGTTCGCAAGCCTGCCGAGTTGCTATGTCCGTCCAG
AATCCGAGAGGCCTAAGTTATCTGAAGTTGCTGATTGCGAAGATGTTCCCGTCATTGATTTGGG
CTGCGGAGATCGTAGCCTGATAGTCAAACAGATCGGTGATGCTTGTCGAGAATATGGATTTTTC
CAGGTtacttaatgtttgaacgtacctcagctactcgttgaaccactagtccaagtgctgattt
cgtttcctcttttggatgtattctgtcaggtGATCAATCATGCCGTGCCGAAAGACATAGTGGA
TAAAATGGTGGGGGTGGCGCATGAATTCTTCAGTCTATCTGTGGAGGAGAAGATGAAATTATAC
TCTGATGACCCTTCAAAAACGATGCGACTCTCTACGAGTTTCAACGTTAGAAAGGAGACCGTTC
ACAACTGGAGAGACTATCTCAGGCTTCATTGCTACCCCTTGGAGAAATACGCGCCTGAATGGCC
GTCTAATCCCTCTTCTTTCAAGtaagccaacctgttttcttagtagtgccagcaaaagattgtt
gatatgaatcgcattttcatttgtaggGATATCGTAAGCACATACTGCAAAGAAGTTCGGGCCC
TGGGATTCTGGTTGCAAGAGGCCATATCGGAGAACCTCGGTTTACACAAAGACTGCCTCAAGAA
TGTATTGGGAGAGCAAGGGCAACACATGGCCATCAACTTCTATCCTGCATGCCCAGAACCAGAT
CTGACTTTCGGATTACCCGCTCATACAGATCCGAATGCGCTCACCATTCTCCTTCAAGATTTAC
TGGTTTCGGGTCTTCNGGTTCTCAAGGGATGGGAAATGGTTAGCAATAAAGCCCCAGCCAGATG
CTTTTGTCATCAACATTGGNGATCAAATCCAGgtgaacactatggaaaatgcatttgtgnccct
ttgcccacaaaaactgcgattcgggtaagatttaggggaaagaggatgaatcatcatcttactg
tttcacgaattaggggatttatcccaccatttgaagttggggtaaattatcctatagtttatt
tccattagagtatttaccctccgtgaataacgatgtcaactgttttgtcacgtcacacccttta
attcccgcgtggaaaaaataattcttttttccagggtattggacgaaaataaaatcgttttgt
ttaacgtcgtccctaatatcgatttatgggaaattcaggaaaattatccgttctcacaagtcat
gttccaacgtttccattaatatgggttgaactgcgtcgttttcgttcaatgcccttaaaataaa
gaacttaatattttttccacgctggcatttaacgtgtgaagtaacgaatgtttgacatagtcat
acatggaggatagaatacccctaaaaatcccctgagaagtgaaacagtaagataacttacccttc
acgattcgtcgtgtgttttcagatcggaggagcattgctctttatatctactgaacaaacttat
cagttcagatgcataagaaaaacagttttagcatctccttactgaactatctgtgcaactcact
tccgGCATTCAGTAATGGGAAGTACAGAAGCGTGTGGCATCGAGCTGTCGTAAATTCGAACAAA
GCCAGACTCTCGGTCGCTTCATTCCTCTGCCCGTGCGATGCAGCAAATATCAGCGCTCCAAATG
AACTTACAACCGGCGATGATCGAGCAATATACAGAGGTTTTACATATGCCGAGTACTACAAAAA
GTTCTGGAGCCGGAACCTGGATCAGGAGCACTGCCTGGAACTATTCAAGAATTAG (SEQ ID NO: 4)

FIG. 4

```
ATGGAAACGAAGGTCATTAGTGGAACACAGTTCGCAAGCCTGCCGAGTTGCTATGTCCGTCCAG
AATCCGAGAGGCCTAAGTTATCTGAAGTTGCTGATTGCGAAGATGTTCCCGTCATTGATTTGGG
CTGCGGAGATCGTAGCCTGATAGTCAAACAGATCGGTGATGCTTGTCGAGAATATGGATTTTTC
CAGGTtacttaatgtttgaacgtacctcagctactcgttgaaccactagtccaagtgctgattt
cgtttcctcttttggatgtattctgtcaggtGATCAATCATGCCGTGCCGAAAGACATAGTGGA
TAAAATGGTGGGGGTGGCGCATGAATTCTCCAGTCTATCCGTGGAGGAGAAGATGAAATTATAC
TCTGATGACCCTTCCAAAACTATGCGACTCTCCACGAGTTTCAACGTTAGAAAGGAGACCGTAC
ACAACTGGAGAGACTATCTCAGGCTTCACTGTTACCCCTTGGAGAAATACGCGCCTGAATGGCC
ATCTAATCCCTCTTCTTTCAAGtaagccaacctgttttcttagtagtgccagcaagagattttt
gagatgaatcgtattttcatttgtaggGATATCGTAAGCACATACTGCAAAGAAGTTCGGGCCC
TGGGATTCTGGTTGCAAGAGGCCATATCGGAGAGCCTCGGTTTACACAAAGACTGCCTCAAGAA
TGTATTGGGAGAGCAAGGGCAACATATGGCCATCAACTTTTATCCTGCATGCCCAGAACCAGAT
CTGACTTTCGGATTACCCGCTCATACAGATCCGAATGCACTCGCCATTCTCCTTCAAGATTTAC
TGGTTTCGGGTCTTCAGGTTCTCAAGGATGGGAAATGGTTAGCAATAAAGCCCCGGCCAGATGC
TTTTGTCATCAACATTGGTGATCAAATCCAGGtgaccactatttgtacaattgttatgtaagaa
tgcccttTatggaaaactgcgattcgggtaagatctaggggaaagaggatgaatccttgtctta
ctgtttcacgaattaggggatttTatcccacaatttcgttcaatgccctaaaaataaagaaatt
aatattttTccacgctggaatttaatgtgtgaagtaaaaatatttgacatcgtcattcatggg
gtgaaacagtaagataacttacccttcatgattcgtcgtgttttttcagatcggaggagcatgg
ctcttttTatctactgaacaaacttatcagttcagatgcataagaaaaactattttagcatctc
cttaccgaactctctctgcaactcacttctgcaggCATTCAGTAATGGGAAGTACAGAAGCGTG
TGGCATCGAGCCGTCGTAAATTCAAACAAAGCTAGACTCTCGGTTGCTTCGTTCCTCTGCCCGT
GTGATGCAGCGAATATCAGCGTTCCAAATGAACTTACAACCGGCGATGATCGAGCAATATACAG
AGGTTTTACATATGCCGAGTACTACAAAAAGTTCTGGAGCCGGAACCTGGACCAGGAGCACTGC
CTGGAACTATTCAAGAATTAG (SEQ ID NO: 5)
```

FIG. 5

(SEQ ID NOS: 10 and 11)

```
Query    1   MVRAACCEKMGVKKGAWSPQEDEILINYIHKYGHGNWRALPKQAGLLRCGKSCRLRWINY   60
             M RA CCEKMGVK+G W+P+ED+ILINYIH YGH NWRALPK AGLLRCGKSCRLRWINY
Sbjct    1   MGRAPCCEKMGVKRGPWTPEEDQILINYIHLYGHSNWRALPKHAGLLRCGKSCRLRWINY   60

Query   61   LKPDIKRGNFTQQEEQTIINLHQMLGNRWSTIAARLPGRTDNEIKNVWHTHLKKKLKDN-  119
             L+PDIKRGNFT QEEQTIINLH+ LGNRWS IAA+LPGRTDNEIKNVWHTHLKK+L   N
Sbjct   61   LRPDIKRGNFTPQEEQTIINLHESLGNRWSAIAAKLPGRTDNEIKNVWHTHLKKRLSKNL  120

Query  120   KYCQDPKRLS-ISECDNNIENVDIIIANSPQGCSSEISSVTDSSLEKIVVKKEEVDYSSE  178
                     D K ++ I+E N +    I+    S Q  S+ I++    S+       K+++    +
Sbjct  121   NNGGDTKDVNGINETTNEDKGSVIVDTASLQQFSNSITTFDISN-----DNKDDIMSYED  175

Query  179   YFPTIDESYWSE----DLFKGDAKEISE-----DVDAKIECVKDSKVEDGSMDFWYNLFT  229
                      ID+S+WS+      D   + K+I +      D ++K     +SK+ +   M+FW+++FT
Sbjct  176   ISALIDDSFWSDVISVDNSNKNEKKIEDWEGLIDRNSKKCSYSNSKLYNDDMEFWFDVFT  235

Query  230   ---RAGDMPDLPEF    240
                R + D+PEF
Sbjct  236   SNRRIEEFSDIPEF    249
```

FIG. 6

```
ATGGTGAGAGCGGCTTGCTGTGAGAAGATGGGAGTGAAGAAAGGGGCATGGAGCCCCCAAGAAG
ACGAGATTCTAATCAATTACATTCACAAATATGGGCATGGAAATTGGAGAGCTCTCCCAAAACA
AGCTGGtacccacttaattaatttcttctgaattttatttatgtctttcagaaaatgcaatcat
aatcataatttGCAGGGCTGTTGAGATGCGGGAAGAGTTGCAGACTGCGATGGATAAACTATTT
GAAGCCAGATATTAAAAGGGGAAATTTTACTCAACAAGAGGAACAAACCATTATCAACTTGCAT
CAAATGCTTGGAAACAGGTcagtctgtcaattttttttttgggtacaatgttctagtttgattt
ccttataaaattattaagtttattgttcttcagttccatttattatacgcagtttaatttat
aattattaactagggtttaattatatcaatgactgttaatatttaatccgtaaaaacacgattt
caatttcaatttaagtgttaatgtatattgaaataatgaatttatgttttgtgagttgtagtgt
tatgtttcttttaggaaaagttttctgtgttagggaattttacgtcttactggttaaaatgtg
cgatacacatattttaatatgaaaatgtagaatagcggttgtttaaaatacgttgagtatgtga
ttggttggtcgctatttgatttgattgattactagagaatcatagatgcaagctgcgtattaac
gaacaaaagtcttgcaattaatcgcttttaacaaatactgaattattcgtaacacgacaaaata
acaattgtctttaagaagaagaaaaaaaggagtcgatcccttctctttaaacgtgcgtcttgga
aacaaaaatcaagaattgctgctataattaatcacataatgaatattgctcttattttaaatgc
cttttagatctacacagtccttaatatatatatatatatatatatatatatatatata
ttgtcacagacaactatgcaagcaagcatcgttctgcatatatctccttaggattttgtgtctc
aacagctaattaattaaatcaaggcacaagatttaatgtttcttcattataatttacctatacc
tcgttatgctgctaatcgccattattttactgctaaaaatctaaatctaattgccccaactcac
gcaaatatcttatgtattacattttttttttatttacagattatttttttttggatttatAGGTG
GTCTACGATCGCAGCACGATTACCTGGACGAACAGACAATGAGATAAAAAATGTTTGGCACACA
CATTTGAAGAAAAAACTTAAAGATAATAAGTATTGTCAAGATCCCAAGAGACTTTCAATTTCAG
AATGTGACAACAATATTGAAAATGTGGACATTATTATTGCTAATAGTCCACAAGGATGTTCTAG
TGAAATATCATCAGTGACCGATTCATCGCTCGAGAAATAGTTGTGAAGAAGGAAGAAGTGGAT
TATTCATCGGAGTATTTTCCGACGATCGACGAGAGTTACTGGTCGGAAGATTTGTTCAAGGGGG
ATGCTAAGGAAATAAGTGAAGATGTTGATGCCAAGATAGAATGTGTGAAGGATTCAAAAGTTGA
GGATGGCAGCATGGACTTTTGGTACAACCTTTTTACTAGAGCTGGTGACATGCCTGATTTGCCA
GAATTTTAG    (SEQ ID NO: 9)
```

FIG. 9A
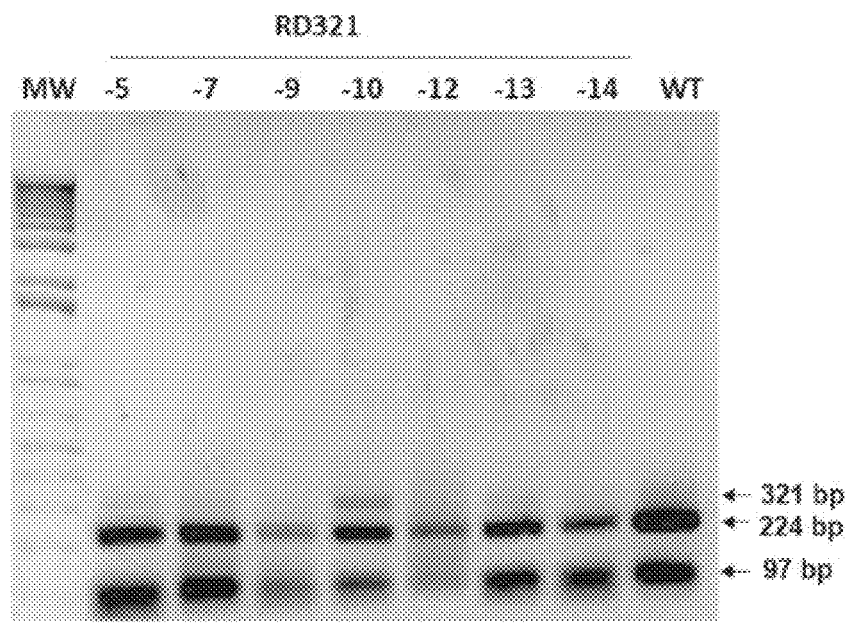
FIG. 9B
321-5    673    TCCGTCAAATCTTTCGCCCCCGCCACCGTCGCCAACTT--GGCCCA SEQ ID NO: 72
WT       181    TCCGTCAAATCTTTCGCCCCCGCCACCGTCGCCAACTTGGGCCCT SEQ ID NO: 73
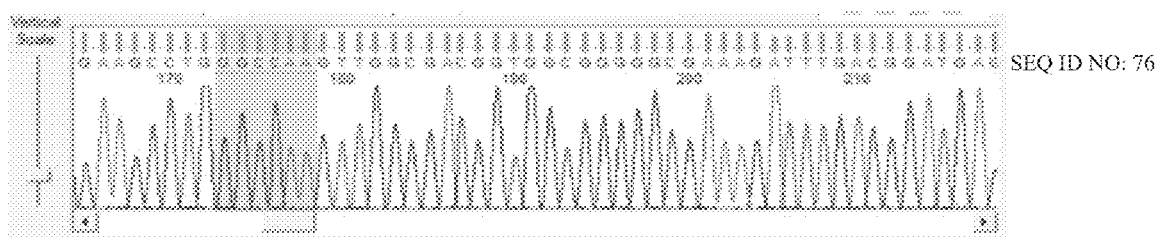
SEQ ID NO: 76
321-13    612    ATGGCCGCCGTCTG--TGAAGCTCAATTTCGCCGCCGCCGCCGCC SEQ ID NO: 74
WT        1     ATGGCCGCCGTCTGCCTGAAGCTCAACTTCGCCGCCGCCGCCGCC SEQ ID NO: 75
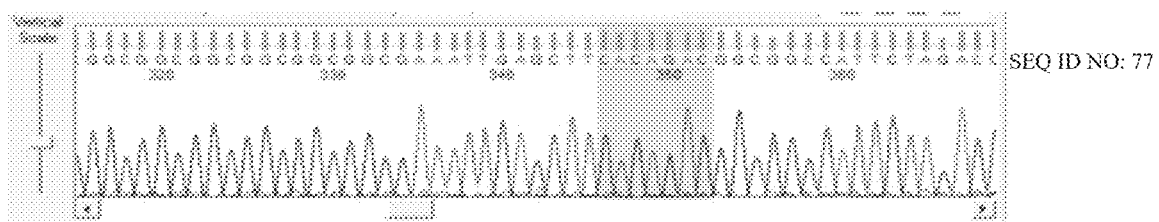
SEQ ID NO: 77

FIG. 15A

| T₀ generation Mutant line | Indel % | Inferred Indel Types — underline gRNA target, bold: insertion (Ns), shaded: PAM | Mutation type fs: frameshift aa: amino acid |
|---|---|---|---|
| | | TCAAATCTTTCGCCCCGCCCCCGCAACTGGACCCAACTTGGAATCGCCAACTTCGACTTTCTGGGATGCG (SEQ ID NO:33) WT ApaI PAM | |
| 321-5 | 22 | TCAAATCTTTCGCCCCGCCCCGCAACTGGACCCAACTGGAA...CAA...CTTCGACTTTCTGGGATGCG (SEQ ID NO:34) | -1 (fs) |
| 321-7 | 19 | TCAAATCTTTCGCCCCGCCCCGCAACTGGACCCAACTTGGA------TTTCTGGGATGCG (SEQ ID NO:35) | -13 (fs) |
| 321-8 | 21 | TCAAATCTTTCGCCCCGCCCCGCAACTGGACCCAACTTGGANNCTTCGACTTTCTGGGATGCG (SEQ ID NO:36) | +6 (+2 aa) |
| 321-10 | 19 | TCAAATCTTTCGCCCCGCCCCGCAACTGGACCCAACTTGGANNNNNCTTCGACTTTCTGGGATGCG (SEQ ID NO:37) | +15 (+5 aa) |
| 321-13 | 22 | | |
| 321-14 | 20 | | |
| 321-12 | 22 | TCAAATCTTTCGCCCCGCCCCGCAACTGGACCCAACTTGG-CTTCGACTTTCTGGGATGCG (SEQ ID NO:38) | -1 (fs) |
| | | TCAAATCTTTCGCCCCGCCCCGCAACTGGACCCAACTTG--CTTCGACTTTCTGGGATGCG (SEQ ID NO:39) | -2 (fs) |
| | | TCAAATCTTTCGCCCCGCCCCGCAACTGGACCCAA----------TTTCTGGGATGCG (SEQ ID NO:40) | -10 (fs) |
| | | TCAAATCTTTCGCCCCGCCCCGCAACTGGA-------------TTTCTGGGATGCG (SEQ ID NO:41) | -13 (fs) |
| | | TCAAATCTTTCGCCCCGCCCCGCAG------------------------GTC (SEQ ID NO:42) | -24 (-8 aa) |
| | | TCAAATCTTTCGCCCCGCCCCGCAACTGGACCCAACTTGGANNCTTCGACTTTCTGGGATGCG (SEQ ID NO:43) | +6 (+2 aa) |
| | | TCAAATCTTTCGCCCCGCCCCGCAACTGGACCCAACTTGGANNNNNCTTCGACTTTCTGGGATGCG (SEQ ID NO:44) | +15 (+5 aa) |

FIG. 15B

| T₁ generation | | Inferred Indel Types | |
|---|---|---|---|
| 321-5-2 | 20 | TCAAATCTTTCGGCCCGCCGCCACCGTCGCCAACTTGGG--CC░░░░CTTCGACTTTCTGGATGCG (SEQ ID NO:45) | -1 (fs) |
| 321-5-5 | 21 | TCAAATCTTTCGGCCCGCCGC░░░░░░░░░░░░░░AAATTGGG (SEQ ID NO:46) | -13 (fs) |
| 321-5-7 | 22 | TCAAATCTTTCGGCCCGCCGCCACCGTCGCCAACTTGGG (SEQ ID NO:47) | +6 (+2 aa) |
| 321-5-8 | 22 | TCAAATCTTTCGGCCCGCCGCCACCGTCGCCAACTTGGG░░░░░░░░░░░░░░░░░░░░░░CTTCGACTTTCTGGATGCG (SEQ ID NO:48) | +15 (+5 aa) |
| 321-13-3 | 21 | | |
| 321-13-4 | 22 | | |
| 321-13-5 | 22 | | |
| 321-5-1 | 33 | TCAAATCTTTCGGCCCGCCGC░░░░░░░░░░░░░AACT░░░░░░░TCTGGGATGCG (SEQ ID NO:49) | -15 (-5 aa) |
| | | TCAAATCTTTCGGCCCGCCGC░░░░░░░░░░░░AACT (SEQ ID NO:50) | -18 (-6 aa) |
| | | TCGGGGATGCGTGAAATCTTCGACTTCGACTTTCTGGATGCG (SEQ ID NO:51) | +1 (fs) |
| 321-5-9 | 20 | TCAAATCTTTCGGCCCGCCGCGACGTGCGACTTGGG--CC░░░░CTTCGACTTTCTGGATGCG (SEQ ID NO:52) | -1 (fs) |
| | | TCAAATCTTTCGGCCCGCCGC░░░░░░░░░░░░░░AACT (SEQ ID NO:53) | -13 (fs) |
| | | TCAAATCTTTCGGCCCGCCGCGACGCGCAACGTC (SEQ ID NO:54) | -16 (fs) |
| | | TCAAATCTTTCGGCCCGCCGCCACCGTCGCCAACTTGGG (SEQ ID NO:55) | +6 (+2 aa) |
| | | TCAAATCTTTCGGCCCGCCGCCACCGTCGCCAACTTGGG░░░░░░░░░░░░░░░░░░░░░░CTTCGACTTTCTGGATGCG (SEQ ID NO:56) | +15 (+5 aa) |
| 321-13-1 | 19 | TCAAATCTTTCGGCCCGCCGCCACCGTCGCCAACTTGGG--CC░░░░CTTCGACTTTCTGGATGCG (SEQ ID NO:57) | -1 (fs) |
| | | TCAAATCTTTCGGCCCGCCGCCACT░░░░░░░░░░AACGCC (SEQ ID NO:58) | -10 (fs) |
| | | TCAAATCTTTCGGCCCGCCGC░░░░░░░░░░░░░░AACT (SEQ ID NO:59) | -13 (fs) |
| | | TCAAATCTTTCGGCCCGCCGC░░░░░░░░░░░░░░░░░ACGTC (SEQ ID NO:60) | -24 (-8 aa) |
| | | TCAAATCTTTCGGCCCGCCGCCACCGTCGCCAACTTGGG (SEQ ID NO:61) | +6 (+2 aa) |
| | | TCAAATCTTTCGGCCCGCCGCCACCGTCGCCAACTTGGG░░░░░░░░░░░░░░░░░░░░░░CTTCGACTTTCTGGATGCG (SEQ ID NO:62) | +15 (+5 aa) |
| 321-13-2 | 17 | TCAAATCTTTCGGCCCGCCGCCACCGTCGCCAACTTGGG--CC░░░░CTTCGACTTTCTGGATGCG (SEQ ID NO:63) | -1 (fs) |
| | | TCAAATCTTTCGGCCCGCCGCCACT░░░░░░░░░░AA (SEQ ID NO:64) | -10 (fs) |
| | | TCAAATCTTTCGGCCCGCCGC░░░░░░░░░░░░░CACCGTC (SEQ ID NO:65) | -13 (fs) |
| | | TCAAATCTTTCGGCCCGCCGC░░░░░░░░░░░░░░░░░ACGTC (SEQ ID NO:66) | -24 (-8 aa) |
| 321-13-9 | 18 | TCAAATCTTTCGGCCCGCCGCGACGTGCGACTTGTCGACTTTCTGGATGCG (SEQ ID NO:67) | -1 (fs) |
| | | TCAAATCTTTCGGCCCGCCGCCACT░░░░░░░░░░AA (SEQ ID NO:68) | -10 (fs) |
| | | TCAAATCTTTCGGCCCGCCGC░░░░░░░░░░░░░░AACT (SEQ ID NO:69) | -13 (fs) |
| | | TCAAATCTTTCGGCCCGCCGCCACCGTCGCCAACTTGGG (SEQ ID NO:70) | +6 (+2 aa) |
| | | TCAAATCTTTCGGCCCGCCGCCACCGTCGCCAACTTGGG░░░░░░░░░░░░░░░░░░░░CC░░░░CTTCGACTTTCTGGATGCG (SEQ ID NO:71) | +15 (+5 aa) |

GENE-EDITED BASIL PLANTS RESISTANT TO DOWNY MILDEW

CROSS-REFERENCE TO RELATED APPLICATIONS

This is the U.S. National Stage of International Application No. PCT/US2021/024697, filed Mar. 29, 2021, which was published in English under PCT Article 21 (2), which in turn claims the benefit of U.S. Provisional Application No. 63/000,586, filed Mar. 27, 2020, both herein incorporated by reference in their entireties.

ACKNOWLEDGMENT OF GOVERNMENT SUPPORT

This invention was made with government support under Grant No. USDA-NIFA-2018-67014-28494-824040 awarded by the United States Department of Agriculture. The government has certain rights in the invention.

FIELD

The disclosure provides methods of making gene-edited plants that are resistant to downy mildew, such as basil plants with reduced expression of homoserine kinase (HSK), 2-oxoglutarate-Fe(II) oxygenase (2OGO), or both. Plants generated using the methods are provided. Such plants can include other desirable traits, such as chill tolerance and reduced bitter taste.

INCORPORATION OF SEQUENCE LISTING

The Sequence Listing is submitted as an ASCII text file, created on Jun. 23, 2023, 111,919 bytes, named 7213-104205-03_ST25.txt, which is incorporated by reference herein.

BACKGROUND

Sweet basil (*Ocimum basilicum* L., Lamiaceae) is the most economically important annual culinary herb in the United States. The increasing demand for fresh market-basil from consumers has resulted in intensive year-round basil production from field and greenhouse systems. In recent years, downy mildew (DM) disease, caused by the oomycete fungus *Peronospora belbahrii* Thines, has become a significant limiting factor in basil production. Downy mildews are obligate biotrophic pathogens that penetrate into host tissues, grow intercellularly and form haustoria in mesophyll and epidermal cells for nutrient uptake. The pathogen produces chlorotic lesions on basil leaves with dark brown sporangia on the abaxial side of the leaf surfaces, greatly reducing basil quality and market value. To-date, almost all sweet basil cultivars are DM susceptible, whereas resistant lines that incorporate genetic resistance from other Ocimum species exhibit sexual incompatibility with sweet basil. At the same time, extant DM tolerant commercial cultivars are under constant threat from newly emerged *P. belbahrii* races. Thus, methods of making plants that are resistant to downy mildew, including basil plants, are needed.

SUMMARY

Provided herein are methods for increasing downy mildew (DM) resistance in a plant, a plant part, or a plant cell, such as basil plant, basil plant part, or basil cell. Such methods can include introducing one or more exogenous nucleic acid molecules that reduces expression of a homoserine kinase (HSK) gene, a 2-oxoglutarate-Fe(II) oxygenase (2OGO) gene or both, into a plant, a plant part, or a plant cell, thereby generating a gene-edited plant, gene-edited plant part, or gene-edited plant cell comprising the exogenous nucleic acid. The HSK gene can encode a protein comprising at least 80%, at least 85%, at least 90%, at least 95%, at least 96%, at least 97%, at least 98%, at least 99%, or 100% identity to SEQ ID NO: 2, and the 2OGO gene can encode a protein comprising at least 80%, at least 85%, at least 90%, at least 95%, at least 96%, at least 97%, at least 98%, at least 99%, or 100% identity to SEQ ID NO: 6. The one or more exogenous nucleic acid molecules reduce expression of HSK and/or 2OGO in the gene-edited plant, gene-edited plant part, or gene-edited plant cell in comparison to a wild type plant, wild type plant part, or wild type plant cell, and wherein the gene-edited plant, gene-edited plant part, or gene-edited plant cell has increased DM resistance in comparison to a wild type plant, wild type plant part, or wild type plant cell. In some examples, DM resistance is increased at least 10%, at least 20%, at least 30%, at least 40%, at least 50%, at least 75%, at least 90%, at least 100%, at least 200%, or at least 400%, for example relative to a plant, plant part, or a plant cell, relative to a native or wild-type plant of the same variety (such as one with a native 2OGO and/or HSK gene sequence).

The method can further include introducing one or more exogenous inhibitory nucleic acid molecules that reduces expression of a MYB14 gene into a plant, a plant part, or a plant cell, thereby generating a gene-edited plant, gene-edited plant part, or gene-edited plant cell comprising the exogenous nucleic acid. The MYB14 gene can encode a protein comprising at least 80%, at least 85%, at least 90%, at least 95%, at least 96%, at least 97%, at least 98%, at least 99%, or 100% identity to SEQ ID NO: 10. The one or more exogenous inhibitory nucleic acid molecules reduce expression of the MYB14 in the plant, plant part, or plant cell in comparison to a wild type plant, wild type plant part, or wild type plant cell, and wherein the plant, plant part, or plant cell has increased chilling tolerance in comparison to a wild type plant, wild type plant part, or wild type plant cell.

Also provided herein are methods for increasing chill or cold tolerance in a plant, a plant part, or a plant cell, such as basil plant, basil plant part, or basil cell. Such methods can include introducing one or more exogenous nucleic acid molecules that reduces expression of a MYB14 gene into a plant, a plant part, or a plant cell, thereby generating a gene-edited plant, gene-edited plant part, or gene-edited plant cell comprising the exogenous nucleic acid. The MYB14 gene can encode a protein comprising at least 80%, at least 85%, at least 90%, at least 95%, at least 96%, at least 97%, at least 98%, at least 99%, or 100% identity to SEQ ID NO: 10. The one or more exogenous nucleic acid molecules reduce expression of MYB14 in the gene-edited plant, gene-edited plant part, or gene-edited plant cell in comparison to a wild type plant, wild type plant part, or wild type plant cell, and wherein the gene-edited plant, gene-edited plant part, or gene-edited plant cell has increased chill or cold tolerance in comparison to a wild type plant, wild type plant part, or wild type plant cell. In some examples, chill or cold tolerance is increased at least 10%, at least 20%, at least 30%, at least 40%, at least 50%, at least 75%, at least 90%, at least 100%, at least 200%, or at least 400%, for example relative to a plant, plant part, or a plant cell, relative to a native or wild-type plant of the same variety (such as one with a native MYB14 gene sequence).

Also provided are gene-edited plants, gene-edited plant parts, and gene-edited plant cells, such as basil plant, basil plant part, or basil cell. For example, a gene-edited plant, gene-edited plant part, or gene-edited plant cell can include one or more exogenous nucleic acids that decrease expression of an HSK gene encoding a protein comprising at least 80%, at least 85%, at least 90%, at least 95%, at least 96%, at least 97%, at least 98%, at least 99%, or 100% identity to SEQ ID NO: 2, a 2OGO gene encoding a protein comprising at least 80%, at least 85%, at least 90%, at least 95%, at least 96%, at least 97%, at least 98%, at least 99%, or 100% identity to SEQ ID NO: 6, or both, wherein decreased expression of the HSK protein and/or 2OGO protein increases resistance to downy mildew in comparison to a wild type plant, wild type plant part, or wild type plant cell. Such can include one or more exogenous inhibitory nucleic acid molecules that reduces expression of a MYB14 gene into a plant, wherein the MYB14 gene encodes a protein having at least 80%, at least 85%, at least 90%, at least 95%, at least 96%, at least 97%, at least 98%, at least 99%, or 100% identity to SEQ ID NO: 10. The one or more exogenous nucleic acid molecules reduce expression of MYB14 increasing chilling tolerance in comparison to a wild type plant, wild type plant part, or wild type plant cell.

In one example, a gene-edited plant, gene-edited plant part, or gene-edited plant cell can include one or more exogenous nucleic acids that decrease expression of a MYB14 gene encoding a protein comprising at least 80%, at least 85%, at least 90%, at least 95%, at least 96%, at least 97%, at least 98%, at least 99%, or 100% identity to SEQ ID NO:10, wherein decreased expression of the MYB14 protein increases chill or cold tolerance in comparison to a wild type plant, wild type plant part, or wild type plant cell.

Also provided are nucleic acid molecules (such as gRNAs) and vectors including such, which can be used to decrease expression of HSK, 2OGO, and/or MYB14, in a plant or plant cell. Exemplary gRNA sequences are provided in SEQ ID NOS: 17, 18, and 22, and can be part of a ribonucleoprotein complex. Exemplary vector sequences are provided in SEQ ID NOS: 15, 16, 20 and 21.

Also provided are gene-edited plant, gene-edited plant part, or gene-edited plant cells comprising a non-native HSK, 2OGO, and/or MYB14 gene sequence, such as one or more of the mutations shown in SEQ ID NOS: 34-71 (see FIGS. 15A-B).

The foregoing and other objects and features of the disclosure will become more apparent from the following detailed description, which proceeds with reference to the accompanying figures.

BRIEF DESCRIPTION OF THE DRAWINGS

FIG. 1 is an alignment of ObHSK (Query; SEQ ID NO: 2) and AtHSK (Sbjct; SEQ ID NO: 3) protein sequences.

FIG. 2 is an alignment of Ob2OGO (Query; SEQ ID NO: 6) and At2OGO (Sbjct; SEQ ID NO: 7) protein sequences.

FIG. 3 is an exemplary Ob2OGO gDNA sequence (SEQ ID NO: 4). The larger intron in the middle is shown in lower case.

FIG. 4 is an exemplary Ob2OGO gDNA sequence (SEQ ID NO: 5). The smaller intron in the middle is shown in lower case.

FIG. 5 is an alignment of ObMYB14 (Query; SEQ ID NO: 10) and AtMYB14 (Sbjct; SEQ ID NO: 11) protein sequences.

FIG. 6 is an exemplary ObMYB14 gDNA sequence (SEQ ID NO: 9). The intron in the middle is shown in lower case.

FIGS. 9A-9B: Identification of RD321 mutants. A. RFLP analysis of the 321 bp PCR fragments spanning the target site by ApaI. MW, molecular weight marker. WT, wild type plant. B. Sequencing of the cloned PCR fragments from RD321-5 (SEQ ID NO: 72) and RD321-13 (SEQ ID NO: 74) aligned with homologous sequences from wild type plants (SEQ ID NOs: 73 and 75 respectively). The underlined DNA sequence indicates the target site for gene editing the ObHSK gene. The sequence "GGGCCC" is recognized by the restriction enzyme ApaI.

FIGS. 15A-15B: Gene editing profiles generated by ICE analysis for all individual To and $T_1$ ObHSK-edited sweet basil plants. SEQ ID NO: shown in parenthesis after the sequence (from top to bottom, SEQ ID NOS: 33-71). "+" indicates addition of nucleotide base (N). "−" indicates deletion of nucleotide base. "f.s." indicates frameshifting mutations. "PAM" (AGG) indicates the protospacer adjacent motif for Cas9. "a.a" stands for amino acid.

SEQUENCE LISTING

Figures 7A, 7B, 7C, 7D:
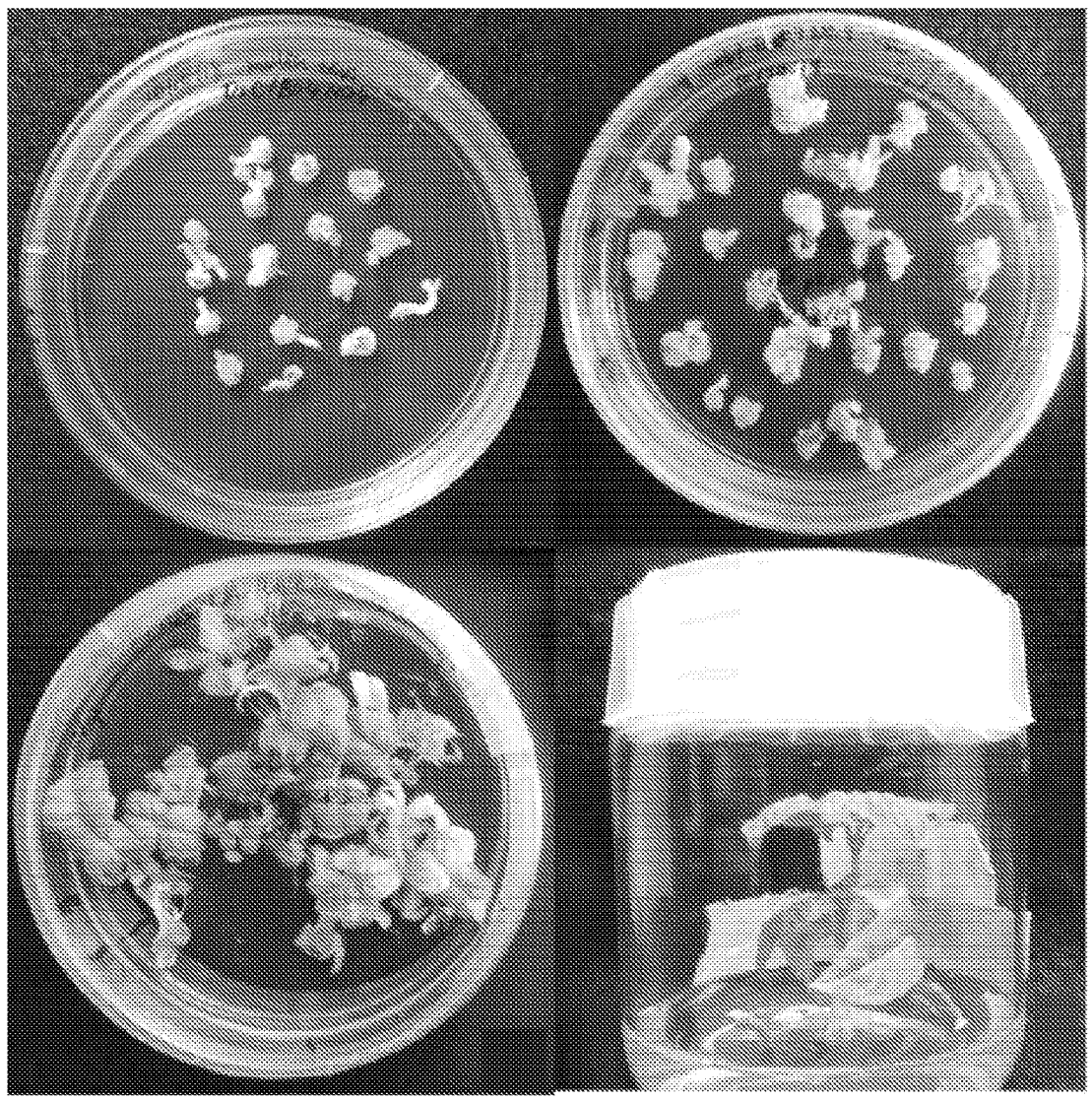
FIGS. 7A-7D: Transformation and regeneration of sweet basil RUSB22 with pRD321 by gene gun bombardment. A. Callus induction from mature embryos. B. Shoot induction from transformed embryos. C. Shoot elongation. D. Root induction.
Figures 8A, 8B, 8C, 8D:
FIGS. 8A-8D: Transformation and regeneration of sweet basil RUSB22 with pRD327 by Agrobacterium. A. Dissection of embryos from mature seeds. B. Callus induction from transformed embryos. C. Shoot induction. D. Root induction.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOS: 1 and 2 are an exemplary HSK gDNA and protein sequences, respectively, from *Ocimum basilicum* L. (ObHSK).

SEQ ID NO: 3 is an exemplary HSK protein sequence from *Arabidopsis* (AtHSK).

SEQ ID NOS: 4 and 5 are an exemplary 2OGO gDNA sequences from *Ocimum basilicum* L. (ObOGO), with a larger intron, and a smaller intron, respectively.

SEQ ID NO: 6 is an exemplary 2OGO protein sequence from *Ocimum basilicum* L. (ObOGO).

SEQ ID NO: 7 is an exemplary 2OGO protein sequence from *Arabidopsis* (AtOGO).

SEQ ID NOS: 8 and 9 are an exemplary MYB14 coding and gDNA sequences from *Ocimum basilicum* L. (ObMYB14), respectively.

SEQ ID NO: 10 is an exemplary MYB14 protein sequence from *Ocimum basilicum* L. (ObMYB14).

SEQ ID NO: 11 is an exemplary MYB14 protein sequence from *Arabidopsis* (AtMYB14).

SEQ ID NO: 12 is an exemplary 23-nt target sequence within ObHSK suitable for gene editing.

SEQ ID NO: 13 is an exemplary 19-nt target sequence within Ob2OGO suitable for gene editing.

SEQ ID NO: 14 is an exemplary 23-nt target sequence within ObHSK suitable for gene editing.

SEQ ID NO: 15 is the nucleic acid sequence of vector pRD321 suitable for ObHSK gene editing. [$P_{AtU6}$::ObHSK-ApaI gRNA::2XP$_{35S}$::hCas9::T$_{NOS}$ in the backbone of pGEM3Zf(+)]. The elements of pRD321 are nt 1-3197 is the pGEM3Zf(+) backbone; nt 3198-34392 is HindIII PAtU6; nt 3493-3515 is ObHSK-ApaI gRNA; nt 3516-3599 is crRNA scaffold; nt 3600-3630 is Spacer XbaI, nt 3631-4532 is SphI 2× 35S promoter XhoI; nt 4533-8811 is optimized 3× FLAG/NLS/hCas9/NLS/TGA/SacI; and nt 8812-9106 is NOS terminator/BamHI/EcoRI.

SEQ ID NO: 16 is the nucleic acid sequence of vector pRD327 suitable for Ob2OGO gene editing. [$P_{AtU6}$::Ob2OGO-ApaI gRNA::2XP$_{35S}$::hCas9::T$_{NOS}$ in the backbone of pCAMBIA2300]The elements of pRD327 are nt 1-8686 pCAMBIA2300 backbone; nt 8687-8981 is HindIII PAtU6; nt 8982-9000 is Ob2OGO-ApaI gRNA; nt 9001-9084 is crRNA scaffold; nt 9085-9115 is Spacer XbaI, nt 9116-10,017 is SphI 2× 35S promoter XhoI; nt 10,018-14,295 is optimized 3× FLAG/NLS/hCas9/NLS/TGA/SacI; and nt 14,295-nt 14591 is NOS terminator/BamHI/EcoRI.

SEQ ID NO: 17 is an exemplary ObHSK guide RNA sequence GCCACCGTCGCCAACTTGGGCCC in gDNA. One skilled in the art will appreciate that the RNA would contain "U" in place of the "T" nucleotides.

SEQ ID NO: 18 is an exemplary Ob2OGO guide RNA sequence is GCAAAGAAGTTCGGGCCCT in gDNA. One skilled in the art will appreciate that the RNA would contain "U" in place of the "T" nucleotides.

SEQ ID NO: 19 is an exemplary *Arabidopsis* U6 promoter sequence.

SEQ ID NO: 20 is the nucleic acid sequence of vector pRD322 suitable for ObHSK gene editing. [$P_{AtU6}$::ObHSK-ApaI gRNA::2XP$_{35S}$::hCas9::T$_{NOS}$ in the backbone of pCAMBIA2300]. The elements of pRD322 are nt 1-8686 pCAMBIA2300 backbone; nt 8687-8981 is HindIII PAtU6; nt 8982-9004 is Ob2HSK-ApaI gRNA; nt 9005-9088 is crRNA scaffold; nt 9089-9119 is Spacer XbaI, nt 9120-10,021 is SphI 2× 35S promoter XhoI; nt 10,022-14,299 is optimized 3× FLAG/NLS/hCas9/NLS/TGA/SacI; and nt 14,300-nt 14595 is NOS terminator/BamHI/EcoRI.

SEQ ID NO: 21 is the nucleic acid sequence of vector pRD488 suitable for ObMYB14 gene editing. [$P_{AtU6}$::ObMYB14-PvuI gRNA::2XP35S::hCas9::T$_{NOS}$ in the backbone of pCAMBIA2300]. The elements of pRD488 are nt 1-8686 pCAMBIA2300 backbone; nt 8687-8981 is HindIII PAtU6; nt 8982-9004 is ObMYB14-PvuI gRNA; nt 9005-9088 is crRNA scaffold; nt 9089-9119 is Spacer XbaI, nt 9120-10,021 is SphI 2X 35S promoter XhoI; nt 10,011-14,299 is optimized 3X FLAG/NLS/hCas9/NLS/TGA/SacI; and nt 14,300-nt 14595 is NOS terminator/BamHI/EcoRI.

SEQ ID NO: 22 is an exemplary Ob2MYB14 guide RNA sequence GACCAGTAACTCTCGTCGATCGT in gDNA. One skilled in the art will appreciate that the RNA would contain "U" in place of the "T" nucleotides.

SEQ ID NOS: 23 and 24 are forward and reverse primers, respectively for ObHSK gDNA.

SEQ ID NOS: 25 and 26 are forward and reverse primers, respectively for RD321.

SEQ ID NOS: 27 and 28 are forward and reverse primers, respectively for ObHSK gDNA.

SEQ ID NOS: 29 and 30 are forward and reverse primers, respectively for ITS-qPCR.

SEQ ID NOS: 31 and 32 are forward and reverse primers, respectively for beta tubulin-qPCR.

SEQ ID NO: 33 is an exemplary portion of an ObHSK sequence that can be targeted for mutation.

SEQ ID NOs: 34-71 are exemplary ObHSK mutated sequences.

SEQ ID NOs: 72-75 are exemplary PCR fragments from RD321-5 (SEQ ID NO: 72), RD321-13 (SEQ ID NO: 74), or WT (SEQ ID NOS: 73 & 75).

SEQ ID NOs: 76 and 77 are exemplary displays of the sequencing analysis.

SEQ ID NOs: 78 and 79 are exemplary ObHSK gDNA PCR fragments, 321-5-2-12 $T_2$ and 321-5-8-1 $T_2$ respectively.

SEQ ID NOs: 80-82 are exemplary sequencing chromatograms of ObHSK gDNA PCR fragments.

DETAILED DESCRIPTION

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a plant" includes one or a plurality of such plants. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference in their entireties. All GenBank® Accession numbers cited herein are incorporated by reference in their entirety for the sequence available on Mar. 27, 2020.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties sought to be obtained by a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

Backcross: The mating of a hybrid to one of its parents. For example hybrid progeny, for example a first generation hybrid ($F_1$), can be crossed back one or more times to one of its parents. Backcrossing can be used to introduce one or more single locus conversions (such as one or more desirable traits) from one genetic background into another.

Basil downy mildew (BDM): The pathogen *Peronospora belbahrii* responsible for causing downy mildew in basil plants. Initial symptoms usually include yellow areas visible on the upper leaf surface often confined within the veins of the leaf. In situations of high disease pressure brought about by greatly increased levels of pathogen spores in the crop canopy brown to black leaf lesions resulting from cell death appear and may expand, subsequently.

The spectrum of resistance through susceptibility to BDM can be measured by fungal sporulation as opposed to symptomatic leaf yellowing, which may be the result of extenuating factors such as nitrogen deficiency. Thus, response can be measured on the basis of % sporulation. In one example, a scale from 0 to 4 is used, comparing all genotypes in a given test (0=no sporulation, 1=1% to 10% sporulation, 2=11% to 25% sporulation, 3=26% to 50% sporulation, and 4=51% to 100% sporulation). This scale facilitates rapid scoring of multiple leaves from individual plants or plots of multiple plants (i.e. homogenous varieties or breeding lines), while providing a repeatable and representative measure of disease reaction on an individual plant basis. For selection of individual plants, six mature leaves are detached from each plant and assigned a score from which a Disease Severity Index (DSI) is calculated on a single-plant basis using the equation:

$$DSI = \frac{\sum (\text{single leaf} \times \text{disease rating})}{(\text{number of leaves scored} \times \text{maximum disease rating})}$$

For isogenic varieties or breeding lines replicated plots, typically grown to between 10-15 feet in height, are assigned a score based on the aggregate level of sporulation among plants. In this case disease severity can be reported as the mean score exhibited across replicated plots on a given date or scoring dates can be combined and used to calculate area under the disease progress curve (AUDPC).

As used herein, "resistance" "to BDM is used to describe plants for which sporulation over the growing season or cycle of the plant has not been observed in any environment and across all levels of disease pressure including the most severe.

As used herein, "resistance" to BDM is used to describe plants for which sporulation over the growing season or cycle of the plant has not been observed in any significant amount across the environments and across all levels of disease pressure including the most severe. Highly resistant and resistant plants may exhibit slight sporulation late in the growing season under the most severe symptoms and exhibit significantly less foliar injury and sporulation than tolerant plants.

As used herein, "tolerance" to BDM is used to describe plants exhibiting some degree of symptoms and/or fungal sporulation that does not preclude its sale in the marketplace. Thus, total yield may decrease but not the extent of significant economic impact with regard to the sale of the product. BDM tolerance can vary according to the number and nature of genes conferring the host response. BDM tolerance can also be subject to interaction with the environment, which directly affects the level of disease pressure and will vary under different environmental conditions, inoculum density, plant age and length of season. Nevertheless, the disclosed gene-edited sweet basil varieties have exhibited under field conditions no-to-few BDM symptoms, depending upon when the rating occurs, and are referred to herein a BDM resistant/tolerant. In addition, the gene-edited plants significantly outperformed commercial controls to which they have been compared, relative to the expression of BDM on the susceptible control sweet basils and the absence of even minimal signs of BDM on these new sweet basils.

Biomass: Organic matter derived from an organism, such as a plant or part thereof. In some examples, biomass refers to all the above ground plant material at a particular point of time, thus including the leaves, stems and may include flowers (at varying stages of development given the flowering period ranges over a period of time). Biomass can include all vegetative and reproductive material produced by the plant at time of harvest.

Cas9: An RNA-guided RNA endonuclease enzyme that can cut DNA. Cas9 has two active cutting sites (HNH and RuvC), one for each strand of the double helix. Catalytically inactive (deactivated) Cas9 (dCas9) is also encompassed by this disclosure. In some examples, a dCas9 includes one or more of the following point mutations: D10A, H840A, and N863A.

Cas9 nucleic acid and protein sequences are publicly available. For example, GenBank® Accession Nos. nucleotides 796693 . . . 800799 of CP012045.1 and nucleotides 1100046 . . . 1104152 of CP014139.1 disclose Cas9 nucleic acids, and GenBank® Accession Nos. AMA70685.1 and AKP81606.1 disclose Cas9 proteins. In some examples, the Cas9 is a deactivated form of Cas9 (dCas9), such as one that is nuclease deficient (e.g., those shown in GenBank® Accession Nos. AKA60242.1 and KR011748.1). In certain examples, Cas9 has at least 80% sequence identity, for example at least 85%, at least 90%, at least 95%, at least 96%, at least 97%, at least 98%, or at least 99% sequence identity to such sequences, and retains the ability to cut DNA.

Cell. Cell as used herein includes a plant cell, whether isolated, in tissue culture or incorporated in a plant or plant part.

Chill or cold tolerance: The ability of a plant to survive and grow (e.g., withstand) in an environment about 0 to 15° C., such as 2 to 15° C., 4 to 10° C., or 4 to 5° C. Thus, plants with chill or cold tolerance display fewer or no chilling injuries, such as chlorosis, necrosis, tissue or organ collapse (e.g. leaves) or growth retardation, as compared to that observed with a native plant of the same type. Chilling tolerance or resistance can include plants (e.g., basil plants) that are intact plants with or without roots, and/or detached stems and leaves, or leaves only, and refers to the plants or parts of plants observable response after being exposed or subjected to chilling and cold temperatures. This could occur when growing in the field and/or in pots and containers (following episodes of low temperatures that can induce chilling injury), or at any time post-harvest during handling, storage, shipping/transport and/or at the retail or consumer end.

Complementarity: The ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

CRISPRs (Clustered Regularly Interspaced Short Palindromic Repeats): The CRISPR RNA array is a defining feature of naturally occurring bacterial CRISPR systems. The term "CRISPR" refers to the architecture of the array which includes constant direct repeats (DRs) interspaced with the variable spacers. In some examples, a CRISPR array includes at least a DR-spacer-DR-spacer. CRISPRs are found in approximately 40% of sequenced bacteria genomes and 90% of sequenced archaea. CRISPRs are often associated with cas genes that code for proteins related to CRISPRs (such as Cas9 and Cas13d proteins). CRISPR/Cas systems can be used for DNA targeting, for example to detect a target DNA, modify a target DNA at any desired location, or cut the target DNA at any desired location.

The CRISPR/Cas system is a prokaryotic immune system that confers resistance to foreign genetic elements such as plasmids and phages and provides a form of acquired immunity. CRISPR spacers recognize and cut these exogenous genetic elements in a manner analogous to the mode of action of RNAi in eukaryotic organisms. CRISPR/Cas systems can be used for gene editing (adding, disrupting or changing the sequence of specific genes) and gene regulation. By delivering a Cas9 protein and appropriate guide RNAs into a cell, the organism's genome can be cut at any desired location (such as a plant HSK, 2OGO, or MYB14 gene).

Cross. Synonymous with hybridize or crossbreed. Includes the mating of genetically different individual plants, such as the mating of two parent plants.

Cross-pollination: Fertilization by the union of two gametes from different plants.

Downregulated or knocked down: When used in reference to the expression of a molecule, such as a target nucleic acid (e.g., HSK, 2OGO, and/or MYB14), refers to any process which results in a decrease in production and/or accumulation of the target nucleic acid or protein encoded thereby, but in some examples not complete elimination of the target nucleic acid product or target nucleic acid function. In one example, downregulation or knock down does not result in complete elimination of detectable target nucleic acid expression or target nucleic acid activity. In some examples, the target nucleic acid is a genomic or coding DNA. In some examples, downregulation or knock down of a target RNA includes processes that decrease translation of the target RNA and thus can decrease the presence of corresponding proteins. In one example RNAi or CRISPR/Cas systems are used to downregulate a target nucleic acid (e.g., HSK, 2OGO, and/or MYB14).

Downregulation or knock down includes any detectable decrease in the target nucleic acid or protein encoded thereby. In certain examples, detectable target nucleic acid (or protein) (e.g., HSK, 2OGO, and/or MYB14) in a cell or plant decreases by at least 10%, at least 20%, at least 30%, at least 40%, at least 50%, at least 60%, at least 70%, at least 75%, at least 80%, at least 90%, at least 95%, at least 96%, at least 97%, at least 98%, at least 99%, or 100% (such as a decrease of 40% to 90%, 40% to 80% or 50% to 95%) as compared to a control (such an amount of target nucleic acid or protein detected in a corresponding wild-type cell or plant). In one example, a control is a relative amount of expression in a wild-type plant cell or plant (e.g., one that has not been gene edited, such as one that is non-recombinant and does not include a Cas protein or guide sequence or other exogenous nucleic acid).

Endogenous: With reference to a nucleic acid and/or protein refers to the nucleic acid and/or protein in question as found in a plant in its natural form (i.e., without any human intervention).

Essential oil (EO): A concentrated hydrophobic liquid containing volatile aroma compounds from aromatic plants, such as a sweet basil plant. An oil is "essential" in the sense that it historically was considered by some to be the "essence of" the plant's fragrance; it does not mean indispensable. The essential oil of sweet basil accumulates in glandular trichomes in leaves and flowers of the sweet basil plant and these compounds impart the characteristic aroma/odor of aromatic plants/culinary herbs including sweet basil and can also contribute to flavor and taste. Methods of generating or obtaining an EO from a plant include extraction by distillation (e.g., by using steam or water or combination), expression, solvent extraction, absolute oil extraction, super critical fluid extraction, cold pressing, or combinations thereof. Methods may also include capturing such aromas that are naturally volatizing from the plant using static or nonstatic headspace above the plant material in an enclosed vial or chamber from which the volatiles are then captured.

Exogenous: As used herein with reference to nucleic acid molecule, protein, vector, or cell, refers to any such molecule/cell that does not originate from that particular cell or plant as found in nature. Thus, a non-naturally-occurring nucleic acid or vector is exogenous to a cell once introduced into the cell. An "exogenous" nucleic acid can either not occur in a plant in its natural form, be different from the nucleic acid in question as found in a plant in its natural form, or can be identical to a nucleic acid found in a plant in its natural form, but integrated not within their natural genetic environment. For example a promoter may be endogenous to plant A, but exogenous to plant B. In one example, a gene-edited plant/plant part/cell provided herein includes an exogenous nucleic acid (e.g., RNAi) specific for HSK, 2OGO, and/or MYB14, which in some examples is integrated at genetic loci of the plant.

$F_1$ hybrid: The first generation progeny of the cross of two stable parents that are nonisogenic or isogenic plants.

Gene editing: A type of gene modification in which a nucleic acid molecule, such as DNA, is inserted, deleted or replaced in a native genome of a cell (such as a plant cell) using engineered nucleases, which create site-specific double-strand breaks (DSBs) at desired locations in the genome, and whose improper repair by endogenous natural mechanisms results in an altered/non-native genomic sequence. Thus, the resulting genome is one that does not occur in nature. In some examples, gene editing results in the introduction of an exogenous transgene (e.g., one that does not occur naturally in the cell into which it is introduced) into the genome. In other examples, a gene-edited plant/plant part/cell provided herein is edited using an exogenous nucleic acid (e.g., gRNA) specific for HSK, 2OGO, or MYB14, thereby altering the endogenous sequence of HSK, 2OGO, or MYB14, but the exogenous nucleic acid molecule is not inserted into the genetic material (e.g., it disrupts the DNA target). In either case, such edited plants, plant parts, and cells are referred to as gene-edited plants, gene-edited plant parts, and gene-edited plant cells, respectively. The induced double-strand breaks are repaired through nonhomologous end-joining (NHEJ) or homologous recombination (HR), resulting in targeted mutations or repairs. CRISPR/Cas methods can be used to edit the sequence of one or more target genes, such as HSK, 2OGO, and/or MYB14. For example, gene editing in a plant can be used to confer a desirable trait to the plant, such as resistance or tolerance to downy mildew and/or chill tolerance.

Genetic inactivation/gene silencing/down-regulation: When used in reference to the expression of a nucleic acid molecule, such as a gene (e.g., HSK, 2OGO, and/or MYB14)., refers to any process which results in a decrease in production of a gene product, such as a decrease of at least 20%, at least 50% or at least 75%. Gene silencing occurs when gene expression is significantly reduced (e.g., a reduction of at least 90%, at least 95%, or at least 99%) or even prevented. It can also be referred to as knocking out gene expression, when the gene is completely silenced. A gene product can be RNA or protein. Gene down-regulation or deactivation includes processes that decrease transcription of a gene or stability or translation of mRNA.

For example, a mutation, such as a substitution, partial or complete deletion, insertion, or other variation, can be made to a gene sequence that significantly reduces (and in some cases eliminates) production of the gene product or renders the gene product substantially or completely non-functional. For example, a genetic inactivation of the HSK gene can produce a basil plant having increased resistance to BDM. Genetic inactivation is also referred to herein as "functional deletion".

Genotype. The genetic constitution of a cell, an organism, or an individual (i.e., the specific allele makeup of the individual) usually with reference to a specific character under consideration.

Guide sequence: A polynucleotide sequence having sufficient complementarity with a target polynucleotide sequence to hybridize with the target sequence and direct sequence-specific binding of a Cas protein (such as Cas9) to the target sequence (such as HSK, 2OGO, and/or MYB14). In some examples, the guide sequence is RNA. In some examples, the guide sequence is DNA. The guide nucleic acid can include modified bases or chemical modifications (e.g., see Latorre et al., *Angewandte Chemie* 55:3548-50, 2016). In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about, or at least about, 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. In some embodiments, a guide sequence is 15-25 nucleotides (such as 18-22 or 18 nucleotides).

The ability of a guide sequence to direct sequence-specific binding of a CRISPR complex to a target sequence may be assessed by a suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions.

In some examples, a gRNA comprises a sequence having at least 80%, at least 90%, at least 95%, or 100% sequence identity to any of SEQ ID NO: 17, 18, and 22. In some examples, a gRNA consists of SEQ ID NO: 17, 18, and 22.

Homoserine kinase (HSK): EC 2.7.1.31, is an enzyme that catalyzes the reaction:

ATP+L-homoserine ⇌ ADP+O-phospho-L-homoserine.

It is shown herein that inactivation of HSK in plants increases their tolerance to downy mildew, such as basil downy mildew in basil plants.

HSK sequences are publicly available. For example, GenBank® Accession Nos: NM_127281.2 and NP_179318.1 disclose *Arabidopsis thaliana* nucleic acid and protein sequences, respectively (SEQ ID NO: 3 provides an exemplary protein sequence); GenBank® Accession Nos. NM_001143304.1 and NP_001136776.1 disclose exemplary *Zea mays* HSK nucleic acid and protein sequences, respectively; and GenBank® Accession Nos: XM_004153414.3 and XP_004153462.1 disclose exemplary *Cucumis sativus* HSK nucleic acid and protein sequences, respectively. However, one skilled in the art will appreciate that in some examples, a HSK sequence can include variant sequences (such as allelic variants and homologs) that retain HSK activity. In some examples, when an HSK gene is inactivated in a plant, it increases resistance to downy mildew, such as basil downy mildew.

An exemplary HSK protein sequence from sweet basil is shown in SEQ ID NO: 2. The disclosure thus provides HSK proteins having at least 80%, at least 85%, at least 90%, at least 95%, at least 96%, at least 97%, at least 98%, at least 99%, or 100% sequence identity to SEQ ID NO: 2. An exemplary HSK genomic sequence from sweet basil is shown in SEQ ID NO: 1. The disclosure thus provides HSK encoding nucleic acid molecules, including genomic DNA and cDNA having at least 80%, at least 85%, at least 90%, at least 95%, at least 96%, at least 97%, at least 98%, at least 99%, or 100% sequence identity to SEQ ID NO: 1.

Increase or Decrease: A statistically significant positive or negative change, respectively, in quantity from a control value. An increase is a positive change, such as an increase at least 50%, at least 100%, at least 200%, at least 300%, at least 400% or at least 500% as compared to the control value. A decrease is a negative change, such as a decrease of at least 20%, at least 25%, at least 50%, at least 75%, at least 80%, at least 90%, at least 95%, at least 98%, at least 99%, or at least 100% decrease as compared to a control value. In some examples the decrease is less than 100%, such as a decrease of no more than 90%, no more than 95% or no more than 99%. In some examples, the control value is a value or range of values expected for the same plant that is not gene-edited, e.g., a wild-type plant (e.g., if the test plant is a gene-edited basil plant, the control can be a native or wild-type basil plant of the same variety).

Isolated: An "isolated" biological component (such as a protein, nucleic acid, guide sequence, or cell) has been substantially separated, produced apart from, or purified away from other biological components in the cell or tissue of a plant in which the component occurs, such as other cells, chromosomal and extrachromosomal DNA and RNA, and proteins. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins. Isolated inhibitory nucleic acid molecules (such as guide nucleic acids or vector comprising such), or cells containing such, in some examples are at least 50% pure, such as at least 75%, at least 80%, at least 90%, at least 95%, at least 98%, or at least 100% pure.

MYB Domain Protein 14 (MYB14): A Transcription Factor

It is shown herein that inactivation of MYB14 in plants increases their tolerance to chilling conditions (e.g., about 0-15° C.).

MYB14 sequences are publicly available. For example, GenBank® Accession Nos: NM_128674.4 and NP_180676.1 disclose *Arabidopsis thaliana* nucleic acid and protein sequences, respectively (SEQ ID NO: 11 provides an exemplary protein sequence); GenBank® Accession Nos. NM_001281203.1 and NP_001268132.1 disclose exemplary *Vitis vinifera* MYB14 nucleic acid and protein sequences, respectively; and GenBank® Accession Nos: MG014217.1 and AXF54235.1 disclose exemplary MYB14 nucleic acid and protein sequences, respectively from *Cucurbita pepo*. However, one skilled in the art will appreciate that in some examples, a MYB14 sequence can include variant sequences (such as allelic variants and homologs) that retain MYB14 activity. In some examples, when an MYB14 gene is inactivated in a plant, it increases cold tolerance in plants, such as basil plant.

An exemplary MYB14 protein sequence from sweet basil is shown in SEQ ID NO: 10. The disclosure thus provides MYB14 proteins having at least 80%, at least 85%, at least 90%, at least 95%, at least 96%, at least 97%, at least 98%, at least 99%, or 100% sequence identity to SEQ ID NO: 10. Exemplary MYB14 genomic and cDNA sequences from sweet basil are shown in SEQ ID NO: 8 and 9. The disclosure thus provides MYB14 encoding nucleic acid molecules, including genomic DNA and cDNA having at least 80%, at least 85%, at least 90%, at least 95%, at least 96%, at least 97%, at least 98%, at least 99%, or 100% sequence identity to SEQ ID NO: 8 or 9.

Non-naturally occurring or engineered: Terms used herein as interchangeably and indicate the involvement of the hand of man. The terms, when referring to nucleic acid molecules or polypeptides indicate that the nucleic acid molecule or the polypeptide is at least substantially free from at least one other component with which they are naturally associated in nature and as found in nature. In addition, the terms can indicate that the nucleic acid molecules or polypeptides have a sequence not found in nature.

Operably linked: A first nucleic acid sequence is operably linked with a second nucleic acid sequence when the first nucleic acid sequence is placed in a functional relationship with the second nucleic acid sequence. For instance, a promoter is operably linked to a nucleic acid sequence (such as a guide nucleic acid sequence) if the promoter affects the transcription or expression of the nucleic acid sequence. Generally, operably linked DNA sequences are contiguous and, where necessary to join two protein-coding regions, in the same reading frame.

2-oxoglutarate-Fe(II) oxygenase (2OGO): A mononuclear iron dioxygenase that catalyzes the reaction:

$$2OG+O_2+S \rightarrow succinate+Co_2+SO$$

It is shown herein that inactivation of 2OGO in plants increases their tolerance to downy mildew, such as basil downy mildew in basil plants.

2OGO sequences are publicly available. For example, GenBank® Accession No: NM_122361.3 and NP_197841.1disclose *Arabidopsis thaliana* nucleic acid and protein sequences, respectively (SEQ ID NO: 7 provides an exemplary protein sequence); GenBank® Accession Nos. XM_002273604 and XP_002273604.1 disclose grape flavanone 3-dioxygenase-like nucleic acid and protein sequences, respectively. However, one skilled in the art will appreciate that in some examples, a 2OGO sequence can include variant sequences (such as allelic variants and homologs) that retain 2OGO activity. In some examples, when a 2OGO gene is inactivated in a plant, it increases resistance to downy mildew, such as basil downy mildew.

An exemplary 2OGO protein sequence from sweet basil is shown in SEQ ID NO: 6. The disclosure thus provides 2OGO proteins having at least 80%, at least 85%, at least 90%, at least 95%, at least 96%, at least 97%, at least 98%, at least 99%, or 100% sequence identity to SEQ ID NO: 6. Exemplary 2OGO genomic sequences from sweet basil are shown in SEQ ID NO: 4 and 5. The disclosure thus provides 2OGO encoding nucleic acid molecules, including genomic DNA and cDNA having at least 80%, at least 85%, at least 90%, at least 95%, at least 96%, at least 97%, at least 98%, at least 99%, or 100% sequence identity to SEQ ID NO: 4 or 5.

Plant: Includes reference to an immature or mature whole plant, including a plant from which seed, roots, or leaves have been removed. Seed or embryo that will produce the plant is also considered to be the plant. The present disclosure also includes seeds produced by the plants provided herein, wherein the seeds can include the exogenous one or more exogenous inhibitory nucleic acid molecules that reduce expression of HSK and/or 2OGO, optionally in combination with one or more exogenous inhibitory nucleic acid molecules that reduce expression of MYB14. In one embodiment, the seeds can develop into plants with increased resistance to downy mildew, such as BDM infection, as compared to a wild-type variety of the plant seed. The present disclosure also includes seeds produced by the plants provided herein, wherein the seeds can include the exogenous one or more exogenous inhibitory nucleic acid molecules that reduce expression of MYB14. In one embodiment, the seeds can develop into plants with increased chilling tolerance, as compared to a wild-type variety of the plant seed. As used herein, a "plant cell" includes, but is not limited to, a protoplast, gamete producing cell, and a cell that regenerates into a whole plant.

Any commercially or scientifically valuable plant can be used in accordance with this disclosure. Exemplary plants include plants belonging to the super family Viridiplantae, such as monocotyledonous and dicotyledonous plants including a fodder or forage legume, ornamental plant, food crop, tree, or shrub, such as *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalyptus* spp., *Euclea schimperi*, *Eulalia vi/losa*, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lo tonus bainesli*, *Lotus* spp., *Macro tyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canadensis*, *Phormium cookianum*, *Photinia* spp., *Picea glauca*, *Pinus* spp., *Pisum sativum*, *Podocarpus totara*, *Pogonarthria fleckii*, *Pogonaffhria squarrosa*, *Populus* spp., *Prosopis cineraria*, *Pseudotsuga menziesii*, *Pterolobium stellatum*, *Pyrus communis*, *Quercus* spp., *Rhaphiolepis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barley, rye, oat, peanut, pea, lentil and alfalfa, cotton, rapeseed, canola, pepper, sunflower, tobacco, eggplant, switchgrass, Miscanthus, Setaria, fescue, eucalyptus, a tree, an ornamental plant, a perennial grass and a forage crop. In a specific example, the plant is a basil plant, such as a sweet basil plant. Other exemplary basils are provided herein.

Plant parts: Includes protoplasts, leaves, stems, roots, root tips, anthers, pistils, seed, embryo, pollen, stamen, ovule, microspore, protoplast, sporophyte, gametophyte, cotyledon, hypocotyl, flower, shoot, tissue, petiole, cells, meristematic cells and the like. Includes plant cells of a tissue culture from which plants can be regenerated. In one example a plant part is a plant cell.

Progeny: Offspring; descendants.

Promoter: An array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). In some examples, a promoter used for recombinant expression of a nucleic acid molecule is not naturally occurring in the cell into which it is introduced, is not native to the nucleic acid molecule to which it is attached, or both. In one example, a promoter used is not endogenous (i.e., is exogenous) to the plant in which it is introduced. Exemplary promoters that can be used include the CaMV 35S promoter and the ubiquitin promoter. In one example the promoter is U3 or U6. In one example the U6 promoter is from *Arabidopsis* (e.g., SEQ ID NO: 19) or the U6 promoter of *Medicago truncatula*.

Recombinant or host cell: A cell that has been genetically altered, or is capable of being genetically altered by introduction of an exogenous polynucleotide, such as a recombinant plasmid or vector, such as one that expresses one or more exogenous nucleic acid molecules that reduce expression of HSK, 2OGO, and/or MYB14. Typically, a host cell is a cell in which a vector can be propagated and its nucleic acid expressed. In specific examples, such cells are plant cells, such as from a monocot or dicot. The term also includes any progeny of the subject host cell. It is understood that all progeny may not be identical to the parental cell since there may be mutations that occur during replication. However, such progeny are included when the term "host cell" is used.

Regeneration: The development of a plant from tissue culture. The cells may, or may not have been genetically modified. Plant tissue culture relies on the fact that all plant cells have the ability to generate a whole plant (totipotency). Single cells (protoplasts), pieces of leaves, or roots can often be used to generate a new plant on culture media given the required nutrients and plant hormones.

Ribonucleoprotein (RNP): A complex of ribonucleic acid and DNA-binding protein. In some examples, the RNP includes one or more, such as 2, 3, 4, or 5 different ribonucleic acids, such as gRNAs specific for different targets (such as SEQ ID NO: 17, 18, and 22, wherein the Ts are replaced with Us). In some examples, the DNA-binding protein is a Cas protein, such as a Cas9 native or mutant protein.

Self-pollination: The transfer of pollen from the anther to the stigma of the same plant.

Sequence identity/similarity: The similarity between amino acid (or nucleotide) sequences is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Variants of protein sequences known and disclosed herein are typically characterized by possession of at least about 80%, at least 90%, at least 95%, at least 96%, at least 97%, at least 98% or at least 99% sequence identity counted over the full length alignment with the amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or at least 95% depending on their similarity to the reference sequence. Methods for determining sequence identity over such short windows are available at the NCBI website on the internet. These sequence identity ranges are provided for guidance only; it is entirely possible that strongly significant homologs could be obtained that fall outside of the ranges provided.

Variants of the disclosed nucleic acid sequences are typically characterized by possession of at least about 80%, at least 90%, at least 95%, at least 96%, at least 97%, at least 98% or at least 99% sequence identity counted over the full length alignment with the nucleic acid sequence using the NCBI Blast 2.0, gapped blastn set to default parameters. One of skill in the art will appreciate that these sequence identity ranges are provided for guidance only; it is possible that sequences coding for the disclosed proteins (e.g., HSK, 2OGO, and MYB14) could be obtained that fall outside of the ranges provided.

Single locus converted (conversion) plant: Plants developed by backcrossing and/or by genetic transformation, wherein essentially all of the desired morphological and physiological characteristics of a particular variety (such as downy mildew resistance and/or cold tolerance) are recovered in addition to the characteristics of the single locus transferred into the variety via the backcrossing technique and/or by genetic transformation.

Sweet basil: As used herein, sweet basil (*Ocimum basilicum* L.) or sometimes referred to as American Basil, French Basil, Italian Basil, refers to any plant from the genus and species *Ocimum basilicum*. As used herein, sweet basil may also refer to a variant, progeny, or offspring of such a plant, including a plant or part thereof. The terms variety, cultivar, or the like may be used interchangeably to refer to a plant of the present disclosure. Some basils from other species (*O.* spp.) can appear visually as sweet basils and other non-*O. basilicum* species also used in the methods provided herein.

Tissue culture: A composition that includes isolated cells of the same or a different type or a collection of such cells organized into parts of a plant. In some example, the tissue culture includes a homogenous population of plant cells. In some example, the tissue culture includes a callus tissue. In some example, the tissue culture includes an anther culture or apical stem tip meristem culture. In another example, the tissue culture includes a hairy root culture.

Tolerance and resistance: Tolerance to a disease or condition refers to plants that can tolerate or withstand a certain amount of disease or condition, but do not display significant symptoms or yield losses. Resistance to a disease refers to the ability of a plant to resist or overcome attempted infection. A "tolerant plant" or "tolerant plant variety" need not possess absolute or complete tolerance. Instead, a "tolerant plant," "tolerant plant variety," or a plant or plant variety with "improved tolerance" will have a level of resistance or tolerance which is higher than that of a comparable susceptible plant or variety.

Transformation: The introduction of exogenous genetic material (e.g., guide nucleic acids and vectors containing such) into cells, for example a plant cell. Exemplary mechanisms that are to transfer DNA into plant cells include (but not limited to) electroporation, microprojectile bombardment, *Agrobacterium*-mediated transformation and direct DNA uptake by protoplasts.

Transgene: An exogenous gene or other genetic material (e.g., guide nucleic acids and vectors containing such) that has been transferred into the genome of a plant or plant cell, for example by genetic engineering methods. Exemplary transgenes include cDNA (complementary DNA) segment, which is a copy of mRNA (messenger RNA), and the gene itself residing in its original region of genomic DNA. In one example, describes a segment of DNA containing a gene sequence that is introduced into the genome of a plant or plant cell. This non-native segment of DNA may retain the ability to produce RNA or protein in the transgenic plant, or it may alter the normal function of the transgenic plant's genetic code. In general, the transferred nucleic acid is incorporated into the plant's germ line. Transgene can also describe any DNA sequence, regardless of whether it contains a gene coding sequence or it has been artificially constructed, which has been introduced into a plant or vector construct in which it was previously not found.

Under conditions sufficient for: A phrase that is used to describe any environment that permits a desired activity. In one example the desired activity is expression of an nucleic acid that can specifically reduce or inhibit expression of HSK, 2OGO, and/or MYB14, in combination with other necessary elements, for example to decrease expression of HSK, 2OGO, and/or MYB14 in a plant to increase its downy mildew resistance and/or chill tolerance.

Vector: A nucleic acid molecule into which a foreign nucleic acid molecule can be introduced without disrupting the ability of the vector to replicate and/or integrate in a host cell. In one example, a vector is not native to the cell into which it is introduced. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. In one example a vector includes a guide nucleic acid specific for HSK, 2OGO, and/or MYB14 operably linked to a non-native promoter (e.g., promoter that does not occur naturally in the plant into which it is introduced).

A vector can include nucleic acid sequences that permit it to replicate in a host cell, such as an origin of replication. A vector can also include one or more selectable marker genes and other genetic elements known in the art. An integrating vector is capable of integrating itself into a host nucleic acid. An expression vector is a vector that contains the necessary regulatory sequences to allow transcription and translation of encoded gene or genes, without vector integration into a host nucleic acid.

One type of vector is a "plasmid," which refers to a circular double stranded DNA loop into which additional DNA segments can be inserted, such as by standard molecular cloning techniques.

Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses).

Overview

This disclosure provides the sweet basil downy mildew (DM) susceptibility gene homoserine kinase (ObHSK). Based on cloning of this gene, methods of manipulating a plant genome, for example using CRISPR-gene editing, to mutate this gene in plants (such as sweet basil, lemon/lime basils, camphor basils, methyl cinnamate basils, eugenol basils, methyl eugenol basils, linalool basils, tree basils, ornamental basil, Thai basil) to provide DM resistance. For example, gene edited downy mildew susceptible sweet basil, 'RUSB22' plants when challenged with P. belbahriil showed significantly reduced susceptibility to DM and increased resistance at the first and second generations, based on phenotypic disease indices and in planta pathogen load. ObHSK plays a role in conditioning DM susceptibility, and gene editing can transform susceptible basil into DM resistant basil. The methods can also be used to increase or enhance the resistance of DM in plants (e.g., basils) that exhibit some level of tolerance to resistance.

All $T_0$ plants generated were phenotypically indistinguishable from WT plants, except for the sterile line 321-12, which contained seven different mutation types, including four types of frameshifting mutations and three types of mutations predicted to alter the protein coding sequence. Most of the $T_1$ plants retained mutations inherited from their parents. A number of $T_1$ ObHSK-edited sweet basil plants were more highly resistant to DM than were WT plants and that partially edited HSK gene may have slowed down disease progression or attenuated pathogen virulence. Furthermore, plants from three $T_2$ lines from each of the 321-5 and 321-13 $T_1$ plants have been shown to be highly resistant to P. belbahrii at the initial infection stage. Even partial disruption of ObHSK alleles may be sufficient to significantly enhance DM resistance in phenotypically normal plants.

Based on the identification of HSK and 2OGO sequences provided herein are gene edited plants that are resistant to DM, such as DM caused by Peronospora belbahrii, or Hyaloperonospora arabidopsidis. DM-resistant plants can require reduced or no fungicide application. The gene-edited plants provided herein, such as those containing a non-native/mutant HSK and/or 2OGO, sequence, in some examples are transgene-free. In one example, the plant is a basil plant, and the DM is caused by Peronospora belbahrii. In one example, the plant is a grape plant, and the DM is Plasmopara viticola. The genomic sequence information for the grape HSK (VvHSK) and the flavanone 3-dioxygenase-like (VvF3DOL, homologous to the At2OGO) genes were identified in grape by genomic bioinformatics analysis. The VvHSK protein is 74% identical to AtHSK, and VvF3DOL is 68% identical to At2OGO, indicating these genes are highly conserved amongst different plant species.

Based on the identification of MYB14 sequences provided herein, provided are gene edited plants that have increased chill tolerance, such as the ability to grow and withstand at temperature of about 0-15° C. The gene-edited plants provided herein, such as those containing a non-native/mutant MYB14 sequence (e.g., a mutated version of SEQ ID NO: 8, 9 or 10), are in some examples are transgene-free.

Provided herein are methods for increasing downy mildew resistance in a plant, a plant part, or a plant cell. The methods can include introducing one or more exogenous nucleic acid molecules that reduce expression of a homoserine kinase (HSK) gene, a 2-oxoglutarate-Fe(II) oxygenase (2OGO) gene or both, into a plant, a plant part, or a plant cell (e.g., by transformation). In one example, an inhibitory nucleic acid, such as RNAi, such as siRNA is used to decrease or reduce expression of HSK and/or 2OGO. In another example, the one or more exogenous nucleic acid molecules (such as a gRNA or gDNA) can mutate a native HSK and/or 2OGO gene in the plant, thereby reducing or inhibiting its expression and/or activity. This generates a gene-edited plant, gene-edited plant part, or gene-edited plant cell, which in some examples includes the exogenous nucleic acid (thereby generating transgenic plants, transgenic plant parts, or transgenic plant cells comprising an exogenous, non-native nucleic acid molecule), but in other examples the exogenous nucleic acid is not retained or is lost is subsequent generations (e.g., through natural chromosomal segregation). The HSK gene (for example prior to its mutation) can encode a protein having at least 80%, at least 85%, at least 90%, at least 95%, at least 96%, at least 97%, at least 98%, at least 99%, or 100% identity to SEQ ID NO: 2. The 2OGO gene (for example prior to its mutation) can encode a protein comprising at least 80%, at least 85%, at least 90%, at least 95%, at least 96%, at least 97%, at least 98%, at least 99%, or 100% identity to SEQ ID NO: 6. In some examples, the HSK gene (for example prior to its mutation) has at least 80%, at least 85%, at least 90%, at least 95%, at least 96%, at least 97%, at least 98%, at least 99%, or 100% sequence identity to SEQ ID NO: 1; the 2OGO gene (for example prior to its mutation) has at least 80%, at least 85%, at least 90%, at least 95%, at least 96%, at least 97%, at least 98%, at least 99%, or 100% sequence identity to SEQ ID NO: 4; the 2OGO gene (for example prior to its mutation) has at least 80%, at least 85%, at least 90%, at least 95%, at least 96%, at least 97%, at least 98%, at least 99%, or 100% sequence identity to SEQ ID NO: 5; or combinations thereof.

In some examples expression of HSK and/or 2OGO in the gene-edited plant, gene-edited plant part, or gene-edited plant cell is reduced by at least 10%, at least 20%, at least 30%, at least 40%, at least 50%, at least 60%, at least 70%, at least 80%, at least 90%, at least 95%, at least 96%, at least 97%, at least 98%, at least 99%, or 100%, for example as compared to a plant, cell, or plant part of the same plant type that is not gene-edited (e.g.,, does not include or express the one or more exogenous nucleic acid molecules that reduce expression of HSK and/or 2OGO). In some examples DM resistance of the HSK and/or 2OGO functionally deleted gene-edited plant, gene-edited plant part, or gene-edited plant cell is increased by at least 10%, at least 20%, at least 30%, at least 40%, at least 50%, at least 60%, at least 70%, at least 80%, at least 90%, at least 95%, at least 100%, at least 200%, at least 300%, at least 400%, or at least 500%, for example as compared to a plant, cell, or plant part of the same plant type that is not gene-edited (e.g., wild type plant, wild type plant part, or wild type plant cell).

The method can further include introducing one or more exogenous nucleic acid molecules that reduce expression of a MYB14 gene into a plant, a plant part, or a plant cell (e.g., by transformation). In one example, an inhibitory nucleic acid, such as RNAi, such as siRNA is used to decrease or reduce expression of MYB14. In another example, the one or more exogenous nucleic acid molecules (such as a gRNA or gDNA) can mutate a native MYB14 gene in the plant, thereby reducing or inhibiting its expression and/or activity. This generates a gene-edited plant, gene-edited plant part, or gene-edited plant cell, which in some examples includes the exogenous nucleic acid (thereby generating transgenic plants, transgenic plant parts, or transgenic plant cells comprising an exogenous, non-native nucleic acid molecule), but in other examples the exogenous nucleic acid is not retained or is lost is subsequent generations (e.g., through natural chromosomal segregation).

Also provided are methods of increasing chill tolerance in a plant, a plant part, or a plant cell. The methods can include introducing one or more exogenous nucleic acid molecules that reduce expression of a MYB14 gene into a plant, a plant part, or a plant cell (e.g., by transfection/transformation). In one example, an inhibitory nucleic acid, such as RNAi, such as siRNA is used to decrease or reduce expression of MYB14. In another example, the one or more exogenous nucleic acid molecules (such as a gRNA or gDNA) can mutate a native MYB14 gene in the plant, thereby reducing or inhibiting its expression and/or activity. This generates a gene-edited plant, gene-edited plant part, or gene-edited plant cell, which in some examples includes the exogenous nucleic acid (thereby generating transgenic plants, transgenic plant parts, or transgenic plant cells comprising an exogenous, non-native nucleic acid molecule), but in other examples the exogenous nucleic acid is not retained or is lost is subsequent generations (e.g., through natural chromosomal segregation).

The MYB14 gene (for example prior to its mutation) encodes a protein comprising at least 80%, at least 85%, at least 90%, at least 95%, at least 96%, at least 97%, at least 98%, at least 99%, or 100% identity to SEQ ID NO: 10. In some examples, the MYB14 gene (for example prior to its mutation) comprises at least 80%, at least 85%, at least 90%, at least 95%, at least 96%, at least 97%, at least 98%, at least 99%, or 100% sequence identity to SEQ ID NO: 8 or 9. In some examples expression of MYB14 in the gene-edited plant, gene-edited plant part, or gene-edited plant cell is reduced by at least 10%, at least 20%, at least 30%, at least 40%, at least 50%, at least 60%, at least 70%, at least 80%, at least 90%, at least 95%, at least 96%, at least 97%, at least 98%, at least 99%, or 100%, for example as compared to a plant, cell, or plant part of the same plant type that is not gene-edited (e.g., does not include or express the one or more exogenous nucleic acid molecules that reduce expression of MYB14). In some examples chill tolerance of the MYB14 functionally deleted gene-edited plant, gene-edited plant part, or gene-edited plant cell is increased by at least 10%, at least 20%, at least 30%, at least 40%, at least 50%, at least 60%, at least 70%, at least 80%, at least 90%, at least 95%, at least 100%, at least 200%, at least 300%, at least 400%, or at least 500%, for example as compared to a plant, cell, or plant part of the same plant type that is not gene-edited (e.g., wild type plant, wild type plant part, or wild type plant cell).

The one or more exogenous nucleic acid molecules can include one or more inhibitory nucleic acids, such as RNA interference (RNAi) molecules, such as antisense molecules, siRNA, microRNA, and the like. In some examples, the one or more exogenous inhibitory nucleic acid molecules include a guide sequence (e.g., gRNA) molecule specific for the HSK, 2OGO and/or MYB14 gene, to introduce or nor more mutations in the target gene to reduce its expression, and the method further includes introducing one or more Cas proteins (e.g., Cas9) or Cas coding sequences into the plant, plant part, or plant cell. In some examples, a RNP complex composed of the Cas protein and one or more gRNAs is introduced into a plant cell.

The method can further include measuring downy mildew infection in the gene-edited plant, gene-edited plant part, or gene-edited plant cell as compared to the wild type plant, wild type plant part, or wild type plant cell. The method can further include measuring chill tolerance in the gene-edited plant, gene-edited plant part, or gene-edited plant cell as compared to the wild type plant, wild type plant part, or wild type plant cell. The method can further include growing the gene-edited plant, gene-edited plant part, or gene-edited plant cell in the presence of a downy mildew, wherein downy mildew infection is reduced, prevented, or delayed in the gene-edited plant, gene-edited plant part, or gene-edited plant cell as compared to a wild type plant, wild type plant part, or wild type plant cell. The method can further include growing the gene-edited plant, gene-edited plant part, or gene-edited plant cell in a cold environment. Exemplary cold environments include a refrigerator, cold storage room for fresh produce, refrigerated truck for storing/distributing fresh produce, and the like. In some examples a cold environments is less than 15° C., less than 15° C., less than 10° C., less than 8° C., or less than 5° C. (but above 0° C.), for example about 4-5° C., such as about 4° C., that is when subject to such temperatures, the plant (e.g., basil) results in chilling injury. Chill tolerance is increased in the gene-edited plant, gene-edited plant part, or gene-edited plant cell as compared to a wild type plant, wild type plant part, or wild type plant cell. In some examples, this reduces or prevent injury to plants, such as sweet basil, during field transplanting or seeding in early spring or still growing in late fall when ambient temperatures are reduced to extend where chilling injury would normally occur and damage the leaves on the whole live plants in the field. In some examples, such gene-edited plants can be field grown or grown in greenhouses and/or tunnels and exposed to chilling temperatures (e.g., about 4-5° C., such as about 4° C.) and the gene-edited plants, in contrast to their non-gene edited controls, will show/exhibit significantly less foliar injury from chilling.

In one example, the disclosed gene-edited plants, gene-edited plant parts, and gene-edited plant cells have/contain one or more exogenous nucleic acids (such as an RNAi) that decrease expression of an HSK gene encoding a protein having at least 80%, at least 85%, at least 90%, at least 95%, at least 96%, at least 97%, at least 98%, at least 99%, or 100% identity to SEQ ID NO: 2, an 2OGO gene encoding a protein having at least 80%, at least 85%, at least 90%, at least 95%, at least 96%, at least 97%, at least 98%, at least 99%, or 100% identity to SEQ ID NO: 6, or both, wherein decreased expression of the HSK protein and/or 2OGO protein increases resistance to downy mildew in comparison to a wild type plant, wild type plant part, or wild type plant cell. In some examples, the HSK gene targeted for reduced expression has at least 80%, at least 85%, at least 90%, at least 95%, at least 96%, at least 97%, at least 98%, at least 99%, or 100% sequence identity to SEQ ID NO: 1; the 2OGO gene targeted for reduced expression has at least 80%, at least 85%, at least 90%, at least 95%, at least 96%, at least 97%, at least 98%, at least 99%, or 100% sequence identity to SEQ ID NO: 4; the 2OGO gene targeted for reduced expression has at least 80%, at least 85%, at least 90%, at least 95%, at least 96%, at least 97%, at least 98%, at least 99%, or 100% sequence identity to SEQ ID NO: 5; or combinations thereof.

In one example, the disclosed gene-edited plants, gene-edited plant parts, and gene-edited plant cells are transgene-free (for example generated using CRISPR/Cas9 non-integrating plasmids or RNPs) but include a mutated HSK gene resulting in decreased or inhibited expression of an HSK protein having at least 80%, at least 85%, at least 90%, at least 95%, at least 96%, at least 97%, at least 98%, at least 99%, or 100% identity to SEQ ID NO: 2, mutated 2OGO gene resulting in decreased or inhibited expression of a protein having at least 80%, at least 85%, at least 90%, at least 95%, at least 96%, at least 97%, at least 98%, at least 99%, or 100% identity to SEQ ID NO: 6, or both, wherein decreased or inhibited expression of the HSK protein and/or 2OGO protein increases resistance to downy mildew in comparison to a wild type plant, wild type plant part, or wild type plant cell. In some examples, the HSK gene (e.g., prior to its mutation) has at least 80%, at least 85%, at least 90%, at least 95%, at least 96%, at least 97%, at least 98%, at least 99%, or 100% sequence identity to SEQ ID NO: 1; the 2OGO gene (e.g., prior to its mutation) has at least 80%, at least 85%, at least 90%, at least 95%, at least 96%, at least 97%, at least 98%, at least 99%, or 100% sequence identity to SEQ ID NO: 4; the 2OGO gene (e.g., prior to its mutation) has at least 80%, at least 85%, at least 90%, at least 95%, at least 96%, at least 97%, at least 98%, at least 99%, or 100% sequence identity to SEQ ID NO: 5; or combinations thereof. In some examples, the gene-edited plants, gene-edited plant parts, and gene-edited plant cells include a mutated HSK gene sequence, such as one or more of the mutations shown in SEQ ID NOS: 34-71. In some examples, the gene-edited plants, gene-edited plant parts, and gene-edited plant cells include a mutated HSK gene sequence, such as one having at least 80%, at least 85%, at least 90%, at least 95%, at least 96%, at least 97%, at least 98%, or at least 99% sequence identity to SEQ ID NO: 1, wherein the sequence retains more of the mutations shown in SEQ ID NOS: 34-71.

In one example, gene-edited plants, gene-edited plant parts, and gene-edited plant cells that have reduced or inhibited HKS and/or 2OGO expression and/or activity, can further include one or more exogenous inhibitory nucleic acid molecules that reduce expression of a MYB14 gene that encodes a protein having at least 80%, at least 85%, at least 90%, at least 95%, at least 96%, at least 97%, at least 98%, at least 99%, or 100% identity to SEQ ID NO: 10; wherein decreased expression of the MYB14 gene increases chilling tolerance in comparison to a wild type plant, wild type plant part, or wild type plant cell. In some examples, the MYB14 gene whose expression is reduced or inhibited has at least 80%, at least 85%, at least 90%, at least 95%, at least 96%, at least 97%, at least 98%, at least 99%, or 100% sequence identity to SEQ ID NO: 8 or 9.

In one example, gene-edited plants, gene-edited plant parts, and gene-edited plant cells having reduced or inhibited HKS and/or 2OGO expression and/or activity, can further include a mutated MYB14 gene and can be transgene-free (for example generated using CRISPR/Cas9 non-integrating plasmids or RNPs), resulting in decreased or inhibited expression of an MYB14 protein having at least 80%, at least 85%, at least 90%, at least 95%, at least 96%, at least 97%, at least 98%, at least 99%, or 100% identity to SEQ ID NO: 10, wherein decreased or inhibited expression of the MYB14 protein increases chill tolerance in comparison to a wild type plant, wild type plant part, or wild type plant cell. In some examples, the MYB14 gene (e.g., prior to its mutation) has at least 80%, at least 85%, at least 90%, at least 95%, at least 96%, at least 97%, at least 98%, at least 99%, or 100% sequence identity to SEQ ID NO: 8 or 9.

In some examples, a vector having at least 80%, at least 85%, at least 90%, at least 95%, at least 96%, at least 97%, at least 98%, at least 99%, or 100% sequence identity to SEQ ID NO: 15 or 20 is used to mutate a HSK gene in a plant, and in some examples the vector includes a guide nucleic acid molecule that can mutate HSK to contain one or more of the mutations shown in SEQ ID NOS: 34-71 (see FIGS. 15A-15B), thereby increasing DM resistance in the plant. In some examples, a vector having at least 80%, at least 85%, at least 90%, at least 95%, at least 96%, at least 97%, at least 98%, at least 99%, or 100% sequence identity to SEQ ID NO: 16 is used to mutate a 2OGO gene in a plant, thereby increasing DM resistance in the plant. In some examples, a vector having at least 80%, at least 85%, at least 90%, at least 95%, at least 96%, at least 97%, at least 98%, at least 99%, or 100% sequence identity to SEQ ID NO: 21 is used to mutate a MYB14 gene in a plant, thereby increasing chill tolerance of the plant.

In one example, a gene-edited plant, gene-edited plant part, or gene-edited plant cell can further include one or more exogenous nucleic acid(s) encoding a protein(s) that confers upon the gene-edited plant, gene-edited plant part, or gene-edited plant cell a desired trait, such as one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance, modified phosphorus characteristics, modified antioxidant characteristics; modified essential seed amino acid characteristics, decreased phytate, modified fatty acid metabolism, and modified carbohydrate metabolism.

Methods of producing a commodity plant product are provided. Such methods can include collecting or producing the commodity plant product from a gene-edited plant, gene-edited plant part, or gene-edited plant cell provided herein (e.g., one that is functionally deleted for HSK, 2OGO, and/or MYB14). For example, such a method can include growing the gene-edited plant, removing the harvestable parts (such as leaves, seeds, or oils) from the gene-edited plant, and producing the product from or by the harvestable parts of the plant. Also provided are commodity plant product produced by such methods, wherein the commodity plant product comprises the at least one exogenous nucleic acid molecule. Exemplary commodity products include a protein concentrate, protein isolate, leaves, extract, or oil.

Methods of producing plant seed are provided herein. Such methods can include crossing a gene-edited plant provided herein (e.g., one that is functionally deleted for HSK, 2OGO, and/or MYB14) with itself or a second plant. In some examples, the second plant is gene-edited. In some examples, the second plant is not gene-edited, but is susceptible to DM or is resistant to DM. Also provided are $F_1$ seed produced by such a method, and a plant or part thereof produced by growing the seed. Such methods can further include (a) crossing a plant grown from said seed with itself or a different plant to produce a seed of a progeny plant of a subsequent generation; (b) growing a progeny plant of a subsequent generation from said seed of a progeny plant of a subsequent generation and crossing the progeny plant of a subsequent generation with itself or a second plant to produce a progeny plant of a further subsequent generation; and (c) repeating steps (a) and (b) using said progeny plant of a further subsequent generation from step (b) in place of the plant grown from said seed in step (a), wherein steps (a) and (b) are repeated with sufficient inbreeding to produce an inbred plant derived from the plant.

The disclosed gene-edited plants, gene-edited plant parts, and gene-edited plant cells (e.g., one that is functionally deleted for HSK, 2OGO, and/or MYB14) can further include a single locus conversion, such as a transgene, for example a single locus that confers a desired trait. Examples of such traits include male sterility, herbicide tolerance, insect resistance, pest resistance, disease resistance, modified fatty acid metabolism, abiotic stress resistance, altered seed amino acid composition, site-specific genetic recombination, and modified carbohydrate metabolism.

Methods for breeding a downy mildew resistant plant, are provided. Such methods can include crossing a gene-edited plant provided herein (e.g., one that is functionally deleted for HSK, 2OGO, or both, and in some examples also MYB14) with a second plant, thereby generating plants resistant to downy mildew. The method can further include obtaining seed from the crossing; planting the seeds and growing the seeds to plants; and selecting from said plants those with reduced downy mildew infection.

Methods for breeding a chill tolerant plant, are provided. Such methods can include crossing a gene-edited plant provided herein (e.g., one that is functionally deleted for MYB14) with a second plant, thereby generating chill tolerant plants. The second plant may or may not be gene-edited. The method can further include obtaining seed from the crossing; planting the seeds and growing the seeds to plants; and selecting from said plants those with increased chill tolerance or using asexual techniques such as from clonally propagating fertile or sterile plants for rapid regeneration of new plants genetically identical to the parent from which they have been propagated.

Also provided are containers (such as a paper, plastic or glass container, such as a bag, envelope, clamshell container, vial, or box), which includes dried, frozen, or fresh leaves (or sprouts or microgreens) of a gene-edited plant provided herein (e.g., one that is functionally deleted for HSK, 2OGO, and/or MYB14); an oil extract of a gene-edited plant provided herein, or combinations thereof. In some examples, the leaves (or sprouts or microgreens) of a gene-edited plant provided herein are provided alone, or in a mixture with other leaves, such as in a salad green mix or a seasoning mix.

In some examples, expression of HSK in the gene-edited plant, gene-edited plant part, or gene-edited plant cell is reduced by at least 10%, at least 20%, at least 30%, at least 40%, at least 50%, at least 60%, at least 70%, at least 80%, at least 90%, at least 95%, at least 96%, at least 97%, at least 98%, at least 99%, or 100%, for example as compared to a plant, cell, or plant part of the same plant type that is not gene-edited (e.g., does not express the one or more exogenous inhibitory nucleic acid molecules that reduce expression of HSK, or has a native non-mutated HSK sequence). In some examples expression of 2OGO in the gene-edited plant, gene-edited plant part, or gene-edited plant cell is reduced by at least 10%, at least 20%, at least 30%, at least 40%, at least 50%, at least 60%, at least 70%, at least 80%, at least 90%, at least 95%, at least 96%, at least 97%, at least 98%, at least 99%, or 100%, for example as compared to a plant, cell, or plant part of the same plant type that is not gene-edited (e.g., does not express the one or more exogenous inhibitory nucleic acid molecules that reduce expression of 2OGO, or has a native non-mutated 2OGO sequence). In some examples downy mildew resistance of the HSK and/or 2OGO functionally deleted gene-edited plant, gene-edited plant part, or gene-edited plant cell is increased by at least 4%, at least 5%, at least 10%, at least 20%, at least 30%, at least 40%, at least 50%, at least 60%, at least 70%, at least 80%, at least 90%, at least 95%, at least 100%, at least 200%, at least 300%, at least 400%, or at least 500%, for example as compared to a plant, cell, or plant part of the same plant type that is not gene-edited (e.g., does not express the one or more exogenous inhibitory nucleic acid molecules that reduce expression of HSK and/or 2OGO). In some examples, increased downy mildew resistance is a reduction, prevention, or delay of downy mildew infection, such as a reduction or delay of at least 4%, at least 10%, at least 20%, at least 30%, at least 40%, at least 50%, at least 60%, at least 70%, at least 80%, at least 90%, at least 95%, at least 96%, at least 97%, at least 98%, at least 99%, or 100%, for example as compared to a plant, cell, or plant part of the same plant type that is not gene-edited (e.g., does not express the one or more exogenous inhibitory nucleic acid molecules that reduce expression of HSK and/or 2OGO, or has a native non-mutated HSK and/or 2OGO sequence) In some examples, combinations of these effects are achieved.

In some examples, the downy mildew is a member of the family Peronosporaceae. In some examples, the gene-edited plant, gene-edited plant part, or gene-edited plant cell is or is from basil, and the downy mildew is basil downy mildew (*Peronospora belbahrii*). In some examples, the gene-edited plant, gene-edited plant part, or gene-edited plant cell is or is from a Cucurbitaceae (e.g., cantaloupe (*Cucumis melo*), cucumber (*Cucumis sativus*), pumpkin, squash, watermelon (*Citrullus lanatus*) and other members of the gourd family) and the downy mildew is *Pseudoperonospora cubensis*. In some examples, the gene-edited plant, gene-edited plant part, or gene-edited plant cell is or is from a grape and the downy mildew is grapevine downy mildew (*Plasmopara viticola*). In some examples, the gene-edited plant, gene-edited plant part, or gene-edited plant cell is or is from a hops (*Humulus lupulus*) and the downy mildew is hop downy mildew (*Pseudoperonospora humuli*). In some examples, the gene-edited plant, gene-edited plant part, or gene-edited plant cell is or is from a soybean and the downy mildew is *Peronospora manshurica*. In some examples, the gene-edited plant, gene-edited plant part, or gene-edited plant cell is or is from a spinach and the downy mildew is *Peronospora effusa*. In some examples, the gene-edited plant, gene-edited plant part, or gene-edited plant cell is or is from a sunflower and the downy mildew is Plasmopara halstedii.

In some examples, the gene-edited plant, gene-edited plant part, or gene-edited plant cell is or is from basil, grape, cantaloupe, cucumber, pumpkin, squash, watermelon, hops, soybean, wheat, rice, corn, barley, spinach, or sunflower. In some examples, the gene-edited plant, gene-edited plant part, or gene-edited plant cell is or is from a monocot. In some examples, the gene-edited plant, gene-edited plant part, or gene-edited plant cell is or is from a dicot.

In some examples, the gene-edited plant, gene-edited plant part, or gene-edited plant cell is or is from basil (e.g., *Ocimum* spp . . . ), such as sweet basil (*Ocimum basilicum*), Thai basil, lemon basil (*O.* ×*citriodorum*), holy basil (*Ocimum tenuiflorum*), cinnamon basil (*O. basilicum* 'Cinnamon'), dark opal basil (*O. basilicum* 'Dark Opal'), Lettuce leaf basil (*O. basilicum* 'Crispum'), purple basil (*Ocimum basilicum* 'Purpurescens'), Rubin basil (*O. basilicum* 'Rubin'), globe basil, dwarf basil, French basil (*O. basilicum* 'Minimum'), African blue basil (*O. basilicum* X *O. kilimandscharicum*), Spice basil (*O. basilicum* X *O. americanum*), African basil (*O. kilimandscharicum*), or clove basil (*Ocimum gratissimum*). Other specific examples are provided below:

| Common name | Species and cultivars |
| --- | --- |
| Sweet basil | *O. basilicum* |
| Lettuce leaf basil | *O. basilicum* 'Lettuce Leaf' |
| Mammoth basil | *O. basilicum* 'Mammoth' |
| Genovese basil | *O. basilicum* 'Genovese Gigante' |
| Nufar basil | *O. basilicum* 'Nufar F1' |
| Spicy globe basil | *O. basilicum* 'Spicy Globe' |
| Greek Yevani basil | *O. basilicum* 'Greek Yevani' |
| Fino verde basil | *O. basilicum piccolo* |
| Boxwood basil | *O. basilicum* 'Boxwood' |
| Purple ruffles basil | *O. basilicum* 'Purple Ruffles' |
| Magical Michael | *O. basilicum* 'Magical Michael' |
| Dark opal basil | *O. basilicum* 'Purpurascens' |
| Red rubin basil | *O. basilicum* 'Red Rubin' |
| Osmin purple basil | *O. basilicum* 'Osmin Purple' |
| Cuban basil | *O. basilicum* |
| Thai basil* | *O. basilicum* var. *thyrsiflorum* |
| 'Siam Queen' | *O. basilicum* var. *thyrsiflorum* 'Siam Queen' |
| Cinnamon basil | *O. basilicum* 'Cinnamon' |
| Licorice basil | *O. basilicum* 'Licorice' |
| Mrs. Burns' Lemon | *O. basilicum* var. *citriodora* 'Mrs. Burns' Lemon' |
| Lemon basil | *O. Africanum* or *O. americanum* |
| Lime basil | *O. Africanum* or *O. americanum* |
| Greek column basil | *O. xcitriodorum* 'Lesbos' |
| Thai lemon basil | *O. xcitriodorum* |
| Holy basil | *O. sanctum* (alt. *O. tenuiflorum*) |
| Clove Basil | *O. gratissimum* |
| Greek basil | *O. minimum* |
| (Greek spicy globe Basil) | (alt. *O. basilicum* var. *minimum*) |
| Dwarf bush basil | *O. minimum* |
| African blue basil | *O. kilimandscharicum* × *basilicum* |
| Spice basil | *O. basilicum* × *americanum* |
| Sweet Dani basil | *O. basilicum* × *americanum* |

*Some may classify some Thai Basils as belonging to *O. tenuiflorum* or form. *O. sanctum*). The botanical taxonomy and nomenclature of the basils are shown above are provided as illustrative examples given there is some taxonomical disagreement with basil (*Ocimum* sp. identification).

In some examples, the plant part is a protoplast, leaf, stem, root, root tips, anther, pistil, stamen, seed, embryo, pollen, ovule, microspore, protoplast, sporophyte, gametophyte, cotyledon, hypocotyl, flower, shoot, tissue, petiole, or meristematic cell.

Exemplary Methods of Gene Editing

In some examples, gene edited plants are generated using CRISPR/Cas9 technologies, for example using a guide nucleic acid molecule specific for HSK, 2OGO, and/or MYB14, that can mutate the target, resulting it its decreased expression and/or activity. The components of the CRISPR/Cas system include the Cas9 nuclease and two small RNAs, crRNA and tracrRNA, which bind the nuclease and guide it to its target through a short (e.g., 20) nucleotide (nt) sequence that hybridizes to the DNA target and an about 80 nt scaffold. Fusion of the two small RNAs into a single guide RNA (gRNA) has further simplified the system and its application in heterologous organisms. The nuclease activity of Cas9 from *Streptococcus pyogenes* results in a double-stranded DNA break (DSB) at a site on the target DNA just upstream of a protospacer adjacent motif (PAM). Genomic DSB can be repaired, either precisely or imperfectly, by the endogenous nonhomologous end joining (NHEJ) repair system. Imperfect repair can generate small insertions and deletions (indels), which may alter or disrupt the ability of the gene to express a functional protein. Homologous sequences present either elsewhere in the genome, on extra-chromosomal elements or on foreign oligonucleotides can invade the Cas9-cut dsDNA and allow the incorporation of foreign sequences at the target site (Frokjaer-Jensen, Genetics, 2013. 195 (3): 635-642).

Unlinked transgenic sequences (comprising the ~100 nucleotide gRNA, the Cas9 cassette and the $Kan^R$ cassette) will naturally segregate away from any gene-edited site in 1/4 of the $T_1$ generation. Thus, it is possible for plants to segregate away from the gRNA/Cas9 transgenes in subsequent generations, thus producing transgene-free, gene-mutated plants. In one example, the use of recombinant DNA in the construction of gene-edited plants is avoided, and instead plant leaf tissues are transformed using pre-assembled gRNAs and Cas9 ribonucleotprotein (RNP) complexes (e.g., wherein the gRNA(s) targets 2OGO, HSK and/or MYB14). In one example, polyethylene glycol (PEG)-transformation of protoplasts (e.g., see Woo et al., Nat. Biotechnol., 2015. 33 (11): 1162-4) or gene gun bombardment of immature embryos with RNPs (e.g., see Zhang et al., Nat Commun, 2016. 7:12617; Liang et al., Nat Commun, 2017. 8:14261) is used.

gRNAs can be produced using commercial kits, such as the Invitrogen GeneArt™ Precision gRNA Synthesis Kit. To produce more gRNAs, a DNA template can be assembled by PCR with forward and reverse overlapping oligonucleotides that contain the target DNA sequence, together with the T7 promoter and universal reverse primers supplied with the kit. In vitro transcripts can be produced by T7 RNA polymerase and purified by phenol/chloroform extraction and ethanol precipitation. The RNP complexes of 1-5 µg gRNA and 1 µg GeneArt™ Platinum™ Cas9 nuclease with nuclear-targeting signal (Invitrogen) can be assembled and incubated for 10 min at room temperature. The RNP complexes can be mixed with 1 mg 0.6 µm gold particles sterilized by 70% ethanol for gene gun bombardment. Seeds can be sterilized by 10% bleach for 15 min and rinsed three times with sterile water. Seeds can then be germinated in Magenta boxes on MS medium. Leaf bases from the first true leaves of 3-week old young plants or callus generated from embryos can be used as explants for bombardment. The bombarded plant tissues can be cultured on MS medium supplemented with Gamborg vitamins, 3% sucrose and 16.8 µM thidiazuron (TDZ) until shoot formation. Regenerated shoots can be transferred onto MS medium without TDZ but containing 1 µg/l indole-3-butyric acid (IBA) to induce root formation. Fully regenerated plantlets can be transferred to soil and allowed to produce seeds under isolated conditions.

Since CRISPR-mediated gene editing occurs in $T_0$ plants, the integration of the gRNA/Cas cassettes into the basil genome can be examined by PCR on $T_0$ plants. Cas9 expression can be validated using a 3X FLAG antibody to detect the epitope-tagged Cas9 protein in Western blot analysis.

In one example, the gene editing method is free of recombinant technology and does not involve T-DNA, Ti-plasmids (or other plasmids), *Agrobacterium* or other pathogenic microbes. Once the gRNA/Cas9 RNP complex is delivered into leaf tissue, it can be rapidly degraded and lost from cells. Gene edited plants without any transgene can be produced immediately from edited plant cells.

Using such methods allows for editing of more than one gene at a time (e.g., both ObHSK and Ob2OGO) by bombarding leaf tissues with two gRNA/Cas9 RNP complexes. Since there is no selectable marker delivered into leaf tissues, regenerated plantlets can be screened for gene-editing individually.

In some examples, gene edited plants are generated using *Agrobacterium*-mediated transformation, which stably integrates a single copy of a transgene into plant genomes (e.g., see Deschamps and Simon, Plant Cell Rep., 2002. 21:359-364; Phippen and Simon, Cell. Dev. Biol., 2000. 36:250-4) to produce gene-edited plants. Seeds can be germinated and the leaf tissues taken as explant for *Agrobacterium* inoculation for 30 min. The EHA105 strain of *Agrobacterium* can be transformed with a CRISPR-editing vector, such as one or more of those provided herein (e.g., SEQ ID NOS: 15, 16, 20, 21). The infected plant tissues can be cultured on MS medium supplemented with Gamborg vitamins, 3% sucrose and 16.8 µM thidiazuron (TDZ) for 3 days, after which plant tissues can be transferred to the same medium containing 300 µg/ml cefotaxime to inhibit the further growth of *Agrobacterium* and 50 µg/ml kanamycin to select transformed tissues and regenerate transgenic shoots. Regenerated transgenic shoots can be transferred onto MS medium without TDZ but containing 25 µg/ml kanamycin and 1 µg/l indole-3-butyric acid (IBA) to induce root formation. Fully regenerated transgenic plantlets can be transferred to soil and allowed to produce seeds. To transgenic plants can be examined for the integration of the transgenes by PCR analysis and the mutation of genes, such as HSK, 2OGFeO, and/or MYB14 genes.

Exemplary Methods of Screening Gene Edited Plants

Gene-edited plants generated using the provided methods, such as those generated to containing a non-native HSK, 2OGFeO, and/or MYB14 gene sequence that provides the resulting plant with resistance to DM, can be screened to identify or confirm the presence of a mutation introduced.

PCR primers can be used to amplify all or a portion of a HSK, 2OGFeO, and/or MYB14 gene sequence, such as ObHSK 321-bp and Ob2OGFeO 396-bp gDNA fragments spanning the selected gene target sites. Restriction enzyme digestion can be carried out on the PCR products. Since restriction enzyme sites can be included at the sites of editing, loss of the ability to digest a PCR product indicates a gene-edited plant. The undigested PCR fragments can be sequenced to confirm the presence and nature of any mutations. RFLP methods can be used to screening large numbers of candidate mutant plants.

A T7E1 assay can be used to screen regenerated mutant plants. This assay allows mutated, edited sites to be detected based on their incomplete hybridization to the WT sequence (due to a mismatch between the WT and edited hybridized DNA strands at the edited site). PCR fragments spanning the mutation sites can be denatured at 95° C. and cooled down to 22° C. slowly using a thermal cycler. Annealed PCR products can be incubated with T7 endonuclease 1 (NEB) at 37° C. for 20 min and analyzed by electrophoresis in 1-2% agarose gel.

A TaqMan probe-based qPCR analysis can be used. TaqMan probes can be designed for each of the WT target sites for HSK, 2OGFeO, and/or MYB14 genes, and synthesized with fluorescence labeling on the 5' end and minor groove binder-nonfluorescent quencher (e.g., MGB-NFQ) on the 3' end. In qPCR analysis, the biallelic mutant will not produce any fluorescent signal, while the WT plant will produce double the signal compared to the monoallelic mutant (e.g., see Li et al., Plant Physiol., 2015. 169 (2): 960-70). This TaqMan-qPCR method in the 96-well format used by the StepOnePlus qPCR System (Applied Biosystems) can be used to screen a large number of regenerated plants, produced by the gene gun bombardment with RNP complexes. This method generates gene edited plants that do not carry selectable marker genes.

Mutations from biallelic To mutants are expected to be inherited in the next generations. For transgenic mutant plants produced by *Agrobacterium*-mediated transformation, gene-specific PCR assays can be used to screen for $T_1$ plants that have segregated out the Cas9 and $Kan^R$ genes. The monoallelic To mutants are expected to segregate according to the Mendelian law with a 1:2:1 ratio.

Exemplary Methods of Testing Gene Edited Plants for Loss of Susceptibility to DM Gene-edited plants can be tested for their resistance to DM, such as that caused by *P. belbahrii* (e.g., using the methods provided in Pyne et al., HortSci., 2014. 49:1041-5). Sporangia can be collected and suspended in sterile water. The inoculum can be adjusted to $5 \times 10^4$ sporangia/ml. Droplets (20 µl) of sporangial suspension can be applied to each cotyledon of 7-day-old (cotyledon growth stage) seedlings. Fourteen-day-old plants (first true leaf pair growth stage) and 21-day-old plants (second true leaf pair growth stage) can be inoculated by saturating leaves with a $1 \times 10^4$ sporangia/ml solution using a handheld sprayer. Inoculated plants can be transferred to a dew chamber for 48 hr. They are then placed in a mist chamber to allow for periods of leaf dryness and sporangiophore emergence from the leaf surface. Control plants can be inoculated with sterile water and maintained in separate chambers. DM resistant cultivars and known susceptible cultivars can be inoculated with *P. belbahrii* as controls. Disease development can be scored 7 and 15 days post inoculation. The disease resistance of the gene edited plants can be compared to known resistant cultivars and known susceptible cultivars.

In some examples, gene-edited, DM resistant plants, such as basil plants, can be further analyzed for their aromatic volatiles and compared to the WT plants. The aroma of individual plants can be analyzed by placing fresh leaves or leaf sections into a Shimadzu headspace (HS) analysis AOC-6000 system with auto sampler coupled to a Shimadzu TQ8040 GCMS Triple Quadrupole MS. This GC/MS with static HS permits high-throughput reproducible volatile capture and analysis. Compound identification can be based upon MS and known standards. Edited mutant plants with the desirable aroma characteristics, along with WT plants, can be further grown-out in greenhouse. Specifically, aroma volatiles will be measured by uniformly sampling 10 leaves from each plant just prior to open bloom. Samples (50 mg) can be heated to 70° C. and agitated for 5 minutes at 150 rpm prior to 1 mL injection. Volatile components for samples can be injected and separated on a Shimadzu AOC-6000 multi-functional autosampler and GC-2010 Plus gas chromatograph, respectively. A TQ8040 mass spectrometer (Shimadzu Scientific Instruments) can be used to generate volatile mass spectra. Alkanes ($C_8$-$C_{20}$) can be co-injected and used to calculate retention indices. A mass spectrum table can be created with Shimadzu Post-Analysis Software by combining all volatile components >1% identified in both parents. This MS table can then be applied to all individuals for volatile identification using total ion content. Peak integration and subsequent quantification can be calculated by relative peak area using Shimadzu Post-Analysis Software. The leaves from promising plants selected for fuller grow-outs and evaluation for DM resistance and aroma, can be harvested and hydrodistilled for essential oil recovery. Essential oil yields can be calculated as percent of dry mass (mg essential oil/100g leaves), and oil composition determined using the same TQ8040 GC/MS. The aroma volatiles can be analyzed using a flame ionization detector and Agilent GC/mass spectrometry (Sims et al.,. J. Medicinally Active Plants, 2013. 2 (3): 33-41).

Gene edited plants can also be evaluated for their *Fusarium oxysporum* f. sp. *basilici* (FOB) resistance and chilling tolerance.

Breeding New Varieties with DM and Chill Tolerance

Methods for crossing one or more of the disclosed gene-edited plants, such as a plant (e.g., basil plant) having reduced expression and/or activity of its HSK gene, 2OGO gene, and/or MYB14 gene, with itself or a second plant are provided, as are the seeds and plants produced by such methods. Such methods can be used for propagation of a new plant variety, or can be used to produce hybrid seeds and the plants grown therefrom. Hybrid plants can be used, for example, in the commercial production of commodity products (including leaves, biomass and extracts) or in breeding programs for the production of novel varieties. A hybrid plant can also be used as a recurrent parent at any given stage in a backcrossing protocol during the production of a single locus conversion (for example introduction of one or more desirable traits) of a gene-edited plant provided herein.

Methods of producing plants and/or seed are provided. Such methods can include crossing one or more of the disclosed gene-edited plants, such as a plant (e.g., basil plant) having reduced expression and/or activity of its HSK gene, 2OGO gene, and/or MYB14, with itself or a second plant and harvesting a resulting seed, such as an $F_1$ hybrid seed. The resulting plant can be grown, resulting in a plant or part thereof (such as an $F_1$ plant).

In one example methods of producing an inbred plant derived from a gene-edited plant provided herein, such as a plant (e.g., basil plant) having reduced expression and/or activity of its HSK gene, 2OGO gene, and/or MYB14 gene. In one example such methods include (a) generating a progeny plant derived from gene-edited plant provided herein, such as a plant (e.g., basil plant) having reduced expression and/or activity of its HSK gene, 2OGO gene, and/or MYB14 gene, by crossing such a gene-edited plant with a second variety; (b) crossing the progeny plant with itself or a second plant to produce a seed of a progeny plant of a subsequent generation; (c) growing a progeny plant of a subsequent generation from said seed and crossing the progeny plant of a subsequent generation with itself or a second plant; and (d) repeating steps (b) and (c) for an additional at least 2 generations (such as at least 3, at least 4, at least 5, at least 6, at least 7, at least 8 at least 9, at least 10, at least 15 or at least 20, such as 2 to 10, 3 to 10, or 3 to 15 generations) with sufficient inbreeding to produce an inbred plant derived from a gene-edited variety provided herein.

The second plant crossed with a gene-edited plant provided herein, such as a plant (e.g., basil plant) having reduced expression and/or activity of its HSK gene, 2OGO gene, and/or MYB14 gene, for the purpose of developing novel varieties, is typically a plant which either itself exhibits one or more desirable characteristics or which exhibits one or more desired characteristic(s) when in hybrid combination. In one example, the second plant is gene-edited. Exemplary desired characteristics can include, but are not limited to: increased seed yield, increased seedling vigor, modified maturity date, desired plant height, high biomass yield, reduced time from sowing to harvest, high anthocyanin content, high phenolic content, herbicide tolerance or resistance, drought tolerance or resistance, heat tolerance or resistance, low or high soil pH level tolerance, salt tolerance or resistance, resistance to an insect, resistance to a bacterial disease, resistance to a viral disease, resistance to a fungal disease, resistance to a nematode, resistance to a pest, male sterility, site-specific recombination, abiotic stress tolerance, and increased DM (such as BDM) tolerance and/or resistance, increased chilling tolerance or resistance to chilling and cold temperatures, improved aroma, improved taste, absence of bitterness or off-flavors . . .

When a gene-edited plant provided herein, such as a plant (e.g., basil plant) having reduced expression and/or activity of its HSK gene, 2OGO gene, and/or MYB14, is crossed with another different variety, first generation ($F_1$) progeny are produced. The hybrid progeny are produced regardless of characteristics of the two varieties produced. As such, an $F_1$ hybrid sweet basil plant can be produced by crossing a gene-edited plant provided herein, such as a plant (e.g., basil plant) having reduced expression and/or activity of its HSK gene, 2OGO gene, and/or MYB14 gene, with any second plant. The second plant can be genetically homogeneous (e.g., inbred) or can itself be a hybrid. Therefore, the disclosure provides any $F_1$ hybrid plant produced by crossing a gene-edited plant provided herein, such as a plant (e.g., basil plant) having reduced expression and/or activity of its HSK gene, 2OGO gene, and/or MYB14 gene, with a second plant (such as a gene-edited plant having one or more genes that confer to the plant one or more desired characteristics).

Plants can be crossed by either natural or mechanical techniques. Natural pollination occurs by self-pollination or natural cross pollination, which typically is aided by pollinating organisms. In either natural or artificial crosses, flowering and flowering time can be a consideration.

Sensitivity to day-length can be a consideration when genotypes are grown outside of their area of adaptation. When genotypes adapted to tropical latitudes are grown in the field at higher latitudes, they may not mature before frost occurs. Plants can be induced to flower and mature earlier by creating artificially short days or by grafting. Plants can be grown in winter nurseries located at sea level in tropical latitudes where day lengths are shorter than their critical photoperiod. The short day lengths and warm temperatures encourage early flowering and seed maturation. Early flowering can be useful for generation advance when only a few self-pollinated seeds per plant are desired, but usually not for artificial hybridization because the flowers self-pollinate before they are large enough to manipulate for hybridization. Yet, often for commercial growers, the delay in flowering (or slowness to bolt) is an advantage in commercial production systems. Artificial lighting can be used to extend the natural day length to about 14.5 hours to obtain flowers suitable for hybridization and to increase yields of self-pollinated seed and to accelerate time to flowering and seed-set. The effect of a short photoperiod on flowering and seed yield can be partly offset by altitude. At tropical latitudes, varieties adapted to the northern U.S. perform more like those adapted to the southern U.S. at high altitudes than they do at sea level. The light level for delay of flowering can be dependent on the quality of light emitted from the source and the genotype being grown. For example, blue light with a wavelength of about 480 nm typically needs more than about 30 times the energy to inhibit flowering as red light with a wavelength of about 640 nm (Parker et al. 1946. *Bot. Gaz.* 108:1-26).

Temperature can also affect the flowering and development of plants. It can influence the time of flowering and suitability of flowers for hybridization. Artificial hybridization is typically successful between about 26° C. and about 32° C.

Self-pollination can occur naturally with no manipulation of the flowers. In some examples, the crossing of two plants is accomplished using artificial hybridization. In artificial hybridization, the flower used as a female in a cross is manually cross pollinated prior to maturation of pollen from the flower, thereby preventing self-fertilization, or alternatively, the male parts of the flower are emasculated using known methods. Exemplary methods for emasculating the male parts of a flower include physical removal of the male parts, use of a cytoplasmic or genetic factor conferring male sterility, and application of a chemical gametocide to the male parts.

For artificial hybridization employing emasculation, flowers that are expected to open the following day are selected on the female parent. The buds are swollen and the corolla is just visible through the calyx or has begun to emerge. Usually no more than two buds on a parent plant are prepared, and all self-pollinated flowers or immature buds are removed, for example with forceps. Immature buds, such as those hidden under the stipules at the leaf axil, are removed. The calyx is removed, for example by grasping a sepal with the forceps, pulling it down and around the flower, and repeating the procedure until the five sepals are removed. The exposed corolla is removed, for example by grasping it just above the calyx scar, then lifting and wiggling the forceps simultaneously. The ring of anthers is visible after the corolla is removed, unless the anthers were removed with the petals. Cross-pollination can then be performed using, for example, petri dishes or envelopes in which male flowers have been collected. Desiccators containing calcium chloride crystals are used in some environments to dry male flowers to obtain adequate pollen shed.

Emasculation is not necessary to prevent self-pollination (Walker et al. 1979. *Crop Sci.* 19:285-286). When emasculation is not used, the anthers near the stigma can be removed to make the stigma visible for pollination. The female flower is usually hand-pollinated immediately after it is prepared; although a delay of several hours does not reduce seed set. Pollen shed typically begins in the morning and can end when temperatures are above about 30° C. Pollen shed can also begin later and continue throughout much of the day with more moderate temperatures.

Pollen is available from a flower with a recently opened corolla, but the degree of corolla opening associated with pollen shed can vary during the day. In many environments, collection and use of male flowers immediately without storage can be conducted. In the southern U.S. and other humid climates, pollen shed occurs in the morning when female flowers are more immature and difficult to manipulate than in the afternoon, and the flowers can be damp from heavy dew. In those circumstances, male flowers are collected into envelopes or petri dishes in the morning, and the open container is typically placed in a desiccator for about 4 hours at a temperature of about 25° C. The desiccator can be taken to the field in the afternoon and kept in the shade to prevent excessive temperatures from developing within it. Pollen viability can be maintained in flowers for up to about 2 days when stored at about 5° C. In a desiccator at about 3° C., flowers can be stored successfully for several weeks; however, varieties can differ in the percentage of pollen that germinates after long-term storage.

Either with or without emasculation of the female flower, hand pollination can be carried out by removing the stamens and pistil from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and high percentages of successful crosses are typically obtained when pollen is clearly visible on the stigma. Pollen shed can be checked by tapping the anthers before brushing the stigma. Several male flowers can be used to obtain suitable pollen shed when conditions are unfavorable, or the same male can be used to pollinate several flowers with good pollen shed.

When male flowers are not collected and dried in a desiccator, the parents of a cross can be planted adjacent to each other. Plants are typically grown in rows about 65 cm to about 100 cm apart, but plant densities for seed production fields can be significantly higher in density without compromising fertilization and seed quality. Yield of self-pollinated seed from an individual plant can range from a few seeds to more than about 1,000 as a function of plant density. A density of about 30 plants/m of row can be used when about 30 or fewer seeds per plant is adequate, about 10 plants/m can be used to obtain about 100 seeds/plant, and about 3 plants/m usually results in a high seed production per plant. Densities of about 12 plants/m or less are commonly used for artificial hybridization.

Multiple planting dates about 7 days to about 14 days apart can typically be used to match parents of different flowering dates. When differences in flowering dates are extreme between parents, flowering of the later parent can be hastened by creating an artificially short day. Alternatively, flowering of the earlier parent can be delayed by use of artificially long days or delayed planting. For example, crosses with genotypes adapted to the southern U.S. are made in northern U.S. locations by covering the late genotype with a box, large can, or similar container to create an artificially short photoperiod of about 12 hours for about 15 days beginning when there are three nodes with trifoliate leaves on the main stem. Plants induced to flower early tend to have flowers that self-pollinate when they are small and can be difficult to prepare for hybridization. Grafting can be used to hasten the flowering of late flowering genotypes.

Plants Having One or More Desired Heritable Traits

The disclosure provides gene-edited plants, such as a plant (e.g., basil plant) having reduced expression and/or activity of its HSK gene, 2OGO gene, and/or MYB14 gene, which can be further modified to include one or more additional desired heritable traits. In some examples, such plants can be developed using backcrossing or genetic engineering (for example by introducing one or more transgenes into a gene-edited plant provided herein, such as a plant (e.g., basil plant) having reduced expression and/or activity of its HSK gene, 2OGO gene, and/or MYB14 gene, wherein the transgenes encode one or more desired traits), wherein essentially all of the desired morphological and physiological characteristics of a disclosed gene-edited plant are recovered (such as DM resistance/tolerance) in addition to a genetic locus transferred into the plant via the backcrossing technique. Plants developed using such methods can be referred to as a single locus converted plant.

In one example, the method of introducing one or more desired traits into one or more of the gene-edited plants provided herein, such as a plant (e.g., basil plant) having reduced expression and/or activity of its HSK gene, 2OGO gene, and/or MYB14 gene, with a second plant having one or more desired traits to produce $F_1$ progeny plants; (b) selecting $F_1$ progeny plants that have the one or more desired traits to produce selected $F_1$ progeny plants; (c) crossing the selected progeny plants with at least a first plant of the gene-edited variety to produce backcross progeny plants; (d) selecting backcross progeny plants that have the one or more desired traits and physiological and morphological characteristics of a gene-edited variety to produce selected backcross progeny plants; and (e) repeating steps (c) and (d) one or more times in succession to produce selected second or higher backcross progeny plants that have the one or more desired traits and the physiological and morphological characteristics of a gene-edited plant provided herein, such as a plant (e.g., basil plant) having reduced expression and/or activity of its HSK gene, 2OGO gene, and/or MYB14 gene, when grown in the same environmental conditions.

Backcrossing methods can be used to improve or introduce a characteristic into a gene-edited plant provided herein, such as a plant (e.g., basil plant) having reduced expression and/or activity of its HSK gene, 2OGO gene, and/or MYB14 gene. The parental plant, which contributes the locus for the desired characteristic, is termed the "nonrecurring" or "donor" parent. This terminology refers to the fact that the nonrecurring parent is used one time in the backcross protocol and therefore does not recur. The parental plant to which the locus or loci from the nonrecurring parent are transferred is known as the recurrent parent as it is used for several rounds in the backcrossing protocol (Poehlman and Sleper. 1995. "Breeding Field Crops" Ames, Iowa: Iowa State University Press; Sprague and Dudley, eds. 1988. Corn and Improvement, 3rd edition). In a typical backcross protocol, the original variety of interest (e.g., gene-edited plant provided herein, such as a plant (e.g., basil plant) having reduced expression and/or activity of its HSK gene, 2OGO gene, and/or MYB14 gene is crossed to a second variety (nonrecurring parent) that carries the single locus of interest (such as a desirable trait) to be transferred. The resulting progeny from this cross are then crossed again to the recurrent parent and the process is repeated until a plant is obtained wherein essentially all of the desired morphological and physiological characteristics of the recurrent parent (e.g., the gene-edited plant provided herein, such as a plant (e.g., basil plant) having reduced expression and/or activity of its HSK gene, 2OGO gene, and/or MYB14 gene) are recovered (such as increased tolerance and/or resistance to downy mildew) in the converted plant, in addition to the single transferred locus from the nonrecurring parent.

A backcross protocol alters or substitutes a single trait or characteristic in the original variety, such as a gene-edited plant provided herein, such as a plant (e.g., basil plant) having reduced expression and/or activity of its HSK gene, 2OGO gene, and/or MYB14 gene. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent can depend on the purpose of the backcross; for example, to add a commercially desirable, agronomically important trait to the plant. The exact backcrossing protocol can depend on the characteristic or trait being altered to determine an appropriate testing protocol. Although backcrossing methods are simplified when the characteristic being transferred is a dominant allele, a recessive allele can also be transferred. In this instance, it can be useful to introduce a test of the progeny to determine if the desired characteristic has been successfully transferred.

In a backcross where the desired characteristic being transferred to the recurrent parent is controlled by a major gene which can be readily evaluated during the backcrossing, it is common to conduct enough backcrosses to avoid testing individual progeny for specific traits such as yield in extensive replicated tests. In general, four or more backcrosses are used when there is no evaluation of the progeny for specific traits, such as yield. As in this example, lines with the phenotype of the recurrent parent can be composited without the usual replicated tests for traits such as yield, in the individual lines.

Varieties can also be developed from more than two parents, for example using modified backcrossing, which uses different recurrent parents during the backcrossing. Modified backcrossing can be used to replace the original recurrent parent with a variety having certain more desirable characteristics, or multiple parents can be used to obtain different desirable characteristics from each.

Many single locus traits are known that are not regularly selected for in the development of a new inbred but that can be improved by backcrossing techniques. Single locus traits can be, but are not necessarily, gene-edited. Examples of these traits include, but are not limited to, male sterility, herbicide resistance, abiotic stress tolerance (such as tolerance or resistance to drought, heat, cold, low or high soil pH level, and/or salt), resistance to bacterial, fungal, or viral disease (such as DM, such as BDM), insect resistance, restoration of male fertility, enhanced nutritional quality, modified phosphorus characteristics, modified antioxidant characteristics, yield stability, and yield enhancement. These comprise genes generally inherited through the nucleus. Thus, plants of a gene-edited plant provided herein, such as a plant (e.g., basil plant) having reduced expression and/or activity of its HSK gene, 2OGO gene, and/or MYB14 gene, or progeny thereof, which include a single locus conversion (such as one that confers a desired trait, such as to DM resistance/tolerance).

Direct selection can be applied where the single locus acts as a dominant trait. An example of a dominant trait is the herbicide resistance trait (such as glyphosate resistance). For the selection process, the progeny of the initial cross are sprayed with a herbicide (such as RoundUp® herbicide) prior to the backcrossing. The spraying eliminates any plants which do not have the desired herbicide resistance characteristic; only those plants which have the herbicide resistance gene are used in the subsequent backcross. This process is then repeated for all additional backcross generations.

Selection of plants for breeding may not be dependent on the phenotype of a plant and instead can be based on genetic investigations. For example, a suitable genetic marker can be used which is genetically-linked to a desired trait. One of these markers can therefore be used to identify the presence or absence of a trait in the offspring of a particular cross, and hence can be used in selection of progeny for continued breeding. This technique is referred to as marker assisted selection. Any other type of genetic marker or other assay which is able to identify the relative presence or absence of a trait of interest in a plant can also be useful for breeding. Procedures for marker assisted selection applicable to plant breeding are well known. Such methods can be useful in the case of recessive traits and variable phenotypes, or where conventional assays are more expensive, time consuming, or otherwise disadvantageous. Types of genetic markers which can be used, but are not limited to, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, which is incorporated herein by reference in its entirety), and Single Nucleotide Polymorphisms (SNPs).

Qualitative characteristics can also be useful as phenotype-based genetic markers in plants; however, some or many may not differ among varieties commonly used as parents. Exemplary genetic markers include flower color, differences in maturity, height, and pest resistance.

Useful or desirable traits can be introduced by backcrossing, as well as directly into a plant by genetic transformation methods. Genetic transformation can therefore be used to insert a selected transgene into a gene-edited plant provided herein, such as a plant (e.g., basil plant) having reduced expression and/or activity of its HSK gene, 2OGO gene, and/or MYB14 gene, or progeny thereof, or can, alternatively, be used for the preparation of transgenes which can be introduced by backcrossing. Thus, the disclosure provides methods of producing a plant of a gene-edited plant provided herein, such as a plant (e.g., basil plant) having reduced expression and/or activity of its HSK gene, 2OGO gene, and/or MYB14 gene, or progeny thereof, that includes one or more added desired traits, for example that include introducing a transgene(s) conferring the one or more desired traits into a gene-edited plant provided herein, such as a plant (e.g., basil plant) having reduced expression and/or activity of its HSK gene, 2OGO gene, and/or MYB14 gene, or progeny thereof (for example by transformation with a transgene that confers upon the sweet basil plant the desired trait), thereby producing a gene-edited plant provided herein, such as a plant (e.g., basil plant) having reduced expression and/or activity of its HSK gene, 2OGO gene, and/or MYB14 gene, or progeny thereof that includes the one or more added desired traits.

Methods for the transformation of plants, including sweet basil, are known. Methods for introducing a desired nucleic acid molecule (e.g., transgene), such as DNA, RNA, or inhibitory RNAs, which can be employed for the genetic transformation of sweet basil include, but are not limited to, electroporation, microprojectile bombardment, *Agrobacterium*-mediated transformation and direct DNA uptake by protoplasts.

To effect transformation by electroporation, friable tissues, such as a suspension culture of cells or embryogenic callus, can be used. Alternatively, immature embryos or other organized tissue can be transformed directly. In this technique, the cell walls of target cells can be partially degraded by exposing them to pectin-degrading enzymes (pectolyases) or mechanically wound tissues in a controlled manner. Protoplasts can also be employed for electroporation transformation of plants (Bates. 1994. *Mol. Biotechnol.* 2 (2): 135-145; Lazzeri. 1995. *Methods Mol. Biol.* 49:95-106).

In microprojectile bombardment, particles (such as those comprised of tungsten, platinum, or gold) are coated with nucleic acids and delivered into cells by a propelling force. For the bombardment, cells in suspension are concentrated on filters or solid culture medium. Alternatively, immature embryos or other target cells can be arranged on solid culture medium. The cells to be bombarded are positioned at an appropriate distance below the macroprojectile stopping plate. An exemplary method for delivering DNA into plant cells by acceleration is the Biolistics Particle Delivery System, which can be used to propel particles coated with DNA or cells through a screen, such as a stainless steel or Nytex screen, onto a surface covered with target plant cells. The screen disperses the particles so that they are not delivered to the recipient cells in large aggregates. A screen intervening between the projectile apparatus and the cells to be bombarded can reduce the size of projectiles aggregate and contribute to a higher frequency of transformation by reducing the damage inflicted on the recipient cells by projectiles that are too large.

*Agrobacterium*-mediated transfer is a method for introducing gene loci into plant cells. DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations (Klee et al. 1985. Bio. Tech. 3 (7): 637-342). Moreover, vectors for *Agrobacterium*-mediated gene transfer have improved the arrangement of genes and restriction sites in the vectors to facilitate the construction of vectors capable of expressing various polypeptide coding genes. Such vectors have convenient multi-linker regions flanked by a promoter and a polyadenylation site for direct expression of inserted polypeptide coding genes. Additionally, *Agrobacterium* containing both armed and disarmed Ti genes can be used for transformation. The use of *Agrobacterium*-mediated plant integrating vectors to introduce DNA into plant cells is known (e.g., Fraley et al. 1985. Bio. Tech. 3 (7): 629-635; U.S. Pat. No. 5,563,055). Briefly, plant tissue (often leaves) is cut into small pieces, e.g. 10 mm×10 mm, and soaked for 10 minutes in a fluid containing suspended

*Agrobacterium*. Some cells along the cut will be transformed by the bacterium, which inserts its DNA into the cell, which is placed on selectable rooting and shooting media, allowing the plants to regrow. Some plants can be transformed just by dipping the flowers into suspension of *Agrobacterium* and then planting the seeds in a selective medium. Sweet basil has been transformed using *Agrobacterium* (Dechamps and Simon. 2002. *Plant Cell Reports* 21:359-364).

Transformation of plant protoplasts can also be achieved using methods based on calcium phosphate precipitation, polyethylene glycol treatment, electroporation, and combinations of these treatments (e.g., Potrykus et al. 1985. *Mol. Gen. Genet.* 199 (2): 169-177; Omirulleh et al. 1993. *Plant Mol. Biol.* 21 (3): 415-428; Fromm et al. 1986. *Nature.* 319 (6056): 791-739; Uchimiya et al. 1986. *Mol. Gen. Genet.* 204 (2): 207-207; Marcotte et al. 1988. *Nature* 335 (6189): 454-457).

In one example, such methods can also be used to introduce transgenes for the production of proteins in gene-edited plant cells. The resulting produced protein can be harvested from the gene-edited plant. The transgene can be harvested from the gene-edited plants that are originated or are descended from a gene-edited plant provided herein, such as a plant (e.g., basil plant) having reduced expression and/or activity of its HSK gene, 2OGO gene, and/or MYB14 gene, a seed of such a plant, or a hybrid progeny of such a plant.

Numerous different genes are known and can be introduced into a gene-edited plant provided herein, such as a plant (e.g., basil plant) having reduced expression and/or activity of its HSK gene, 2OGO gene, and/or MYB14 gene, or progeny thereof. Non-limiting examples of particular genes and corresponding phenotypes that can be chosen for introduction into a plant are provided herein.

Herbicide Resistance

One or more herbicide resistance genes can be used with the methods and plants provided herein. In particular examples, a herbicide resistance gene confers tolerance to an herbicide comprising glyphosate, sulfonylurea, imidazalinone, dicamba, glufosinate, phenoxy proprionic acid, cyclohexone, triazine, benzonitrile, broxynil, L-phosphinothricin, cyclohexanedione, chlorophenoxy acetic acid, or combinations thereof.

In one example the herbicide resistance gene is a gene that confers resistance to an herbicide that inhibits the growing point or meristem, such as an imidazalinone or a sulfonylurea. Exemplary genes in this category code for mutant ALS and AHAS enzyme as described, for example, by Lee et al. (1988. *Embryo J.* 7:1241-8) and Miki et al. (1990. *Theoret. Appl. Genet.* 80:449-458).

Resistance genes for glyphosate (resistance conferred by mutant 5-enolpyruvl-3 phosphikimate synthase (EPSP) and aroA genes, respectively) and other phosphono compounds such as glufosinate (phosphinothricin acetyl transferase (PAT) and *Streptomyces hygroscopicus* phosphinothricin-acetyl transferase (bar) genes) can be used (e.g., see U.S. Pat. No. 4,940,835). Examples of specific EPSPS transformation events conferring glyphosate resistance are described, for example, in U.S. Pat. No. 6,040,497.

DNA molecules encoding a mutant aroA gene are known (e.g., ATCC accession number 39256 and U.S. Pat. No. 4,769,061), as are sequences for glutamine synthetase genes, which confer resistance to herbicides such as L-phosphinothricin (e.g., U.S. Pat. No. 4,975,374), phosphinothricin-acetyltransferase (e.g., U.S. Pat. No. 5,879,903).DeGree F. et al. (1989. *Bio/Technology* 61-64) describe the production of gene-edited plants that express chimeric bar genes coding for phosphinothricin acetyl transferase activity. Exemplary genes conferring resistance to phenoxy propionic acids and cyclohexones, such as sethoxydim and haloxyfop are the Acct-S1, Accl-S2 and Acct-S3 genes described by Marshall et al. (1992. *Theor Appl Genet.* 83:435-442).

Exemplary genes conferring resistance to an herbicide that inhibits photosynthesis include triazine (psbA and gs+ genes) and benzonitrile (nitrilase gene) (see Przibilla et al., 1991. *Plant Cell.* 3:169-174). Nucleotide sequences for nitrilase genes are disclosed in U.S. Pat. No. 4,810,648, and DNA molecules containing these genes are available under ATCC Accession Nos. 53435, 67441, and 67442. Cloning and expression of DNA coding for a glutathione S-transferase is described by Hayes et al. (1992. *Biochem. J.* 285:173).

U.S. Patent Publication No: 20030135879 describes dicamba monooxygenase (DMO) from *Pseuodmonas maltophilia*, which is involved in the conversion of a herbicidal form of the herbicide dicamba to a non-toxic 3,6-dichlorosalicylic acid and thus can be used for producing plants tolerant to this herbicide.

The metabolism of chlorophenoxyacetic acids, such as, for example 2,4-D herbicide, is well known. Genes or plasmids that contribute to the metabolism of such compounds are described, for example, by Muller et al. (2006. *Appl. Environ. Microbiol.* 72 (7): 4853-4861), Don and Pemberton (1981. *J Bacteriol* 145 (2): 681-686), Don et al. (1985. *J Bacteriol* 161 (1): 85-90) and Evans et al. (1971. *Biochem J* 122 (4): 543-551).

Disease Resistance

Plant defenses are often activated by specific interaction between the product of a disease resistance gene (R) in the plant and the product of a corresponding avirulence (Avr) gene in the pathogen. A plant, such as a gene-edited plant provided herein, such as a plant (e.g., basil plant) having reduced expression and/or activity of its HSK gene, 2OGO gene, and/or MYB14 gene, or progeny thereof, can be transformed with cloned resistance gene to engineer plants that are resistant to specific pathogen strains. See, for example Jones et al. (1994. *Science* 266:789) (tomato Cf-9 gene for resistance to *Cladosporium fulvum*); Martin et al. (1993. *Science* 262 (5138): 1432-1436) (tomato Pto gene for resistance to *Pseudomonas syringae* pv.); and Mindrinos et al. (1994. *Cell* 78:1089-1099) (*Arabidopsis* RSP2 gene for resistance to *Pseudomonas syringae*).

A viral-invasive protein or a complex toxin derived therefrom can also be used for viral disease resistance. For example, the accumulation of viral coat proteins in transformed plant cells imparts resistance to viral infection and/or disease development effected by the virus from which the coat protein gene is derived, as well as by related viruses. See Beachy et al. (1990. *Annu Rev Phytopathol* 28:451-474). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody can also be used. See, for example, Tavladoraki et al. (1993. *Nature* 366:469-472), which shows that transgenic plants expressing recombinant antibody genes are protected from virus attack.

Logemann et al. (1992. *Bio/Technology* 10:305-308) disclosed that transgenic plants expressing a barley ribosome-inactivating gene have an increased resistance to fungal disease.

Insect Resistance

One example of an insect resistance gene includes a *Bacillus thuringiensis* (Bt) protein, a derivative thereof or a synthetic polypeptide modeled thereon (e.g., see Geiser et al., 1986. Gene 48:109, discloses a Bt Δ-endotoxin gene). Moreover, DNA molecules encoding Δ-endotoxin genes can be obtained from the ATCC (Manassas, VA), for example under ATCC Accession Nos. 40098, 67136, 31995 and 31998. Another example is a lectin. See, for example, Van Damme et al. (1994. *Plant Mol Biol* 24 (5): 825-830), which discloses several *Clivia miniata* mannose-binding lectin genes. A vitamin-binding protein can also be used, such as avidin. See WIPO Publication No. WO 1994/000992, which discloses the use of avidin and avidin homologues as larvicides against insect pests.

In one example the insect resistance gene is an enzyme inhibitor, for example, a protease, proteinase inhibitor, or an α-amylase inhibitor. See, for example, Abe et al. (1987. *J. Biol. Chem.* 262:16793-7; discloses a rice cysteine proteinase inhibitor), Genbank Accession Nos. Z99173.1 and DQ009797.1 which disclose proteinase inhibitor coding sequences, and Sumitani et al. (1993. *Plant Mol. Biol.* 21:985; discloses *Streptomyces nitrosporeus* α-amylase inhibitor). An insect-specific hormone or pheromone can also be used. See, for example, Hammock et al. (1990. Nature 344:458-461; discloses juvenile hormone esterase, an inactivator of juvenile hormone).

Still other examples include an insect-specific antibody or an immunotoxin derived therefrom and a developmental-arrestive protein. See Taylor et al. (1994. Seventh Intl. Symposium on Molecular Plant-Microbe Interactions (Edinburgh Scotland), Abstract #497), who described enzymatic inactivation in transgenic tobacco via production of single-chain antibody fragments.

Male Sterility

Genetic male sterility can increase the efficiency with which hybrids are made, in that it can eliminate the need to physically emasculate the plant used as a female in a given cross (Brim and Stuber. 1973. *Crop Sci.* 13:528-530). Herbicide-inducible male sterility systems are known (e.g., U.S. Pat. No. 6,762,344).

Where use of male-sterility systems is desired, it can be beneficial to also utilize one or more male-fertility restorer genes. For example, where cytoplasmic male sterility (CMS) is used, hybrid seed production involves three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the plant is utilized. However, in many cases, the seeds are considered to be a valuable portion of the crop, thus, it is desirable to restore the fertility of the hybrids in these crops. Therefore, the disclosure provides a gene-edited plant provided herein, such as a plant (e.g., basil plant) having reduced expression and/or activity of its HSK gene, 2OGO gene, and/or MYB14 gene, comprising a genetic locus capable of restoring male fertility in an otherwise male-sterile plant. Examples of male-sterility genes and corresponding restorers which can be employed are well known (see, e.g., U.S. Pat. No. 5,530,191 and U.S. Pat. No. 5,684,242).

Tissue Cultures and In Vitro Regeneration of Plants

Tissue cultures of one or more of the gene-edited plants provided herein, such as a plant (e.g., basil plant) having reduced expression and/or activity of its HSK gene, 2OGO gene, and/or MYB14 gene, are provided. A tissue culture includes isolated cells of the same or a different type or a collection of such cells organized into parts of a plant. Exemplary types of tissue cultures include protoplasts, calli and plant cells that are intact in plants or parts of plants, such as embryos, pollen, flowers, leaves, roots, root tips, anthers, meristematic cells, pistil, seed, petiole, stein, ovule, cotyledon, hypocotyl, shoot or stem, and the like. In a particular example, the tissue culture includes embryos, protoplasts, meristematic cells, pollen, leaves or anthers of the gene-edited plants provided herein, such as a plant (e.g., basil plant) having reduced expression and/or activity of its HSK gene, 2OGO gene, and/or MYB14 gene. Also provided are plants regenerated from such tissue cultures, wherein the regenerated plant expresses the physiological and morphological characteristics of a new gene-edited plant disclosed herein.

Methods for preparing tissue cultures of regenerable plant cells and regenerating plants therefrom, are known, such as those disclosed in U.S. Pat. Nos. 4,992,375; 5,015,580; 5,024,944, and 5,416,011. Tissue culture provides the capability to regenerate fertile plants. This can allow, for example, transformation of the tissue culture cells followed by regeneration of gene-edited plants. For transformation to be efficient and successful, DNA can be introduced into cells that give rise to plants or germ-line tissue.

Plants can be regenerated using organogenesis, embryo rescue, or somatic embryogenesis. Organogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Organogenesis and somatic embryogenesis are different processes and the specific route of regeneration is primarily dependent on the explant source and media used for tissue culture manipulations. While the systems are different, both systems show variety-specific responses where some lines are more responsive to tissue culture manipulations than others. A line that is highly responsive in organogenesis may not generate many somatic embryos, while lines that produce large numbers of embryos during an "induction" step (typically, exposure of the plant material to a specific regimen of plant growth regulators) may not give rise to rapidly-growing proliferative cultures. In addition to line-specific responses, proliferative cultures can be observed with both shoot morphogenesis and somatic embryogenesis. Proliferation allows a single, transformed cell to multiply to the point that it can contribute to germ-line tissue.

Organogenesis is a system whereby shoots are obtained de novo from cotyledonary nodes of seedlings (Wright et al., 1986. *Plant Cell Reports* 5:150-154). The shoot meristems form subepidermally and morphogenic tissue can proliferate on a medium containing benzyl adenine (BA). This system can be used for transformation if the subepidermal, multicellular origin of the shoots is recognized and proliferative cultures are utilized. Tissue that can give rise to new shoots are targeted and proliferated within the meristematic tissue to lessen problems associated with chimerism.

Somatic embryogenesis is a system in which embryogenic tissue is obtained from the zygotic embryo axis (Christianson et al., 1983. *Science* 222:632-634). The embryogenic cultures are proliferative and the proliferative embryos are of apical or surface origin with a small number of cells contributing to embryo formation. The origin of primary embryos (the first embryos derived from the initial explant) is dependent on the explant tissue and the auxin levels in the induction medium (Hartweck et al., 1988. *In Vitro Cell. Develop. Bio.* 24:821-828). With proliferative embryonic cultures, single cells or small groups of surface cells of the "older" somatic embryos form the "newer", more recently developed somatic embryos.

Embryogenic cultures can also be used for regeneration, including regeneration of gene-edited plants.

Methods of Making Plant Extracts

Extracts can be generated from the gene-edited plants provided herein, such as a plant (e.g., basil plant) having reduced expression and/or activity of its HSK gene, 2OGO gene, and/or MYB14 gene, or progeny thereof. Such extracts can be used in aroma and flavoring and medicinal or health-oriented plant based extracts. In some examples, the extract includes genetic material from the gene-edited plants provided herein, such as a plant (e.g., basil plant) having reduced expression and/or activity of its HSK gene, 2OGO gene, and/or MYB14 gene.

In one example, plants of the gene-edited plants provided herein, such as a plant (e.g., basil plant) having reduced expression and/or activity of its HSK gene, 2OGO gene, and/or MYB14 gene, or any above-ground part of the plant, are harvested, for example, after at least 20 days, at least 30 days, at least 45 days, at least 60 days, at least 70 days, at least 90 days, at least 100 days, or at least 120 days of growth (such as after 45 to 100 days, 60 to 100 days, or 50 to 90 days, such as after 60 days or 90 days of growth). The plant can be dried, for example by leaving it in the field to partially dry, or brought indoors to be flash frozen, frozen, boiled, heated, or dried, for example at 37° C. (e.g., by air drying, forced air heat, solar drying, microwaving, lyophilization, or combinations thereof, such as by using a Powell walk-in forced air dryer) or other drying system until no further moisture loss is noted under the temperature and pressure and relative humidity of the drying system. The leaves and flowers of the plant can be separated from the stems, for example manually or by machine. Essential oils can be extracted from the dried leaves and flowers using steam or hydro-distillation or hot water. In some examples, solvent extraction and super critical fluids are used. The plant from which an extract is generated can be field-grown, greenhouse grown or grown in pots, sacs and containers, and cut at any height above the soil, and the plant distilled fresh or partially dried to obtain the aromatic essential oil. Sweet basil plants are typically cut once per growing season, but the gene-edited plants provided herein, such as a plant (e.g., basil plant) having reduced expression and/or activity of its HSK gene, 2OGO gene, and/or MYB14, can be harvested (or cut) once or twice or more per growing season, provided it is grown with ample water, nutrients and under environmental conditions that result in plant growth and development. Once harvested, the plant can be distilled immediately, allowed to be partially dried in full sun, partial sun in the field and then placed into a container for steam or hydro-distillation or allowed to further dried and processed at future time. Other processes can also be used, including but not limited to, solvent extraction. For an extract or dry product, the plant may be sun dried, dried in shade, with or without artificial heat introduced by different sources, and then allowed to dry before extraction.

Products

The disclosure provides products obtained from one or more of the gene-edited plants provided herein, such as a plant (e.g., basil plant) having reduced expression and/or activity of its HSK gene, 2OGO gene, and/or MYB14 gene, or progeny thereof. Exemplary products include a biomass or part thereof, such as an extract, oil, protein isolate, protein concentrate, oil extract, flour, milk, or leaves. For example, a dried biomass and/or leaves of one or more of the gene-edited plant provided herein, such as a plant (e.g., basil plant) having reduced expression and/or activity of its HSK gene, 2OGO gene, and/or MYB14, or progeny thereof can be used as part of food, beverage, or aroma-based product. In some examples, the product includes at least one cell, DNA, and/or protein of a gene-edited plant provided herein, such as a plant (e.g., basil plant) having reduced expression and/or activity of its HSK gene, 2OGO gene, and/or MYB14 gene. In some examples, the products include a mutant (e.g., non-native), HSK, 2OGO, and/or MYB14 molecule, such as a mutant nucleic acid (e.g., DNA or RNA) or protein.

The disclosure provides containers, such as a glass, paper, or plastic container, which includes leaves of a gene-edited plant provided herein, such as a plant (e.g., basil plant) having reduced expression and/or activity of its HSK gene, 2OGO gene, and/or MYB14 gene. The leaves can be dried, frozen, or fresh. In some examples, the container includes leaves (or other parts) from other plants, such as oregano, parsley, marjoram, thyme, rosemary, or non sweet basils, or combinations thereof. In some examples, the container includes garlic, such as dried or fresh garlic.

Provided herein is a dried tea, food and flavor or fragrance product which includes leaves or comes from an oil extract, and/or biomass of one or more of the gene-edited plants provided herein, such as a plant (e.g., basil plant) having reduced expression and/or activity of its HSK gene, 2OGO gene, and/or MYB14 gene, or progeny thereof. Also provided is a liquid tea, produced from leaves, oil extract, and/or biomass of one or more of the gene-edited plants provided herein, such as a plant (e.g., basil plant) having reduced expression and/or activity of its HSK gene, 2OGO gene, and/or MYB14 gene, or progeny thereof.

Provided herein are pet toys or aromatic toys/balls/ornamentals/aromatic wreaths/other personal consumer items, which include leaves, oil extract, and/or biomass of one or more of the gene-edited plants provided herein, such as a plant (e.g., basil plant) having reduced expression and/or activity of its HSK gene, 2OGO gene, and/or MYB14, or progeny thereof.

Oil extracts of one or more of the gene-edited plants provided herein, such as a plant (e.g., basil plant) having reduced expression and/or activity of its HSK gene, 2OGO gene, and/or MYB14 gene, or progeny thereof are provided, and in one example are formulated into a spray.

Example 1

Identification of Basil Genes Responsible for

Downy Mildew (DM) Disease Resistance

Currently, there are no reports on basil genes that confer susceptibility to DM. RNAseq analysis was performed on basil breeding line 'RUSB22-1', which is highly susceptible to DM and highly tolerant to *Fusarium oxysporum* f. sp. *basilicum* (FOB) and has the desirable flavor and aroma characteristics. Using the *Arabidopsis* genome as a reference for query using the NCBI tblastn program the cDNA sequences of sweet basil 2-oxoglutarate-Fe(II) oxygenase (2OGO) (Ob2OGO) and sweet basil homoserine kinase (HSK) (ObHSK) and were identified in the RUSB22 transcriptome. Bioinformatic analysis and comparison to *Arabidopsis* AtHSK (accession #NM_127281) and At2OGO (accession #NM_122361.3) indicated that ObHSK and Ob2OGO mRNA sequences represent likely homologs of the *Arabidopsis* AtHSK and At2OGO genes, respectively.

PCR primers were used to clone the cDNAs and the genomic DNAs (gDNAs) of ObHSK and Ob2OGO. ObHSK (SEQ ID NO: 2) is 79.2% similar to AtHSK (SEQ ID NO: 3) at the amino acid sequence level (FIG. 1) (this comparison excludes N-terminal amino acids 1-51 which diverge between *Arabidopsis* and basil), and like AtHSK, ObHSK does not contain an intron. The ObHSK gDNA sequence is shown in SEQ ID NO: 1. Alignment of ObHSK between cultivars 'RUSB22' and 'Genoveser' showed 98.94% similarity with only three amino acids different.

Ob2OGO (SEQ ID NO: 6) is 68% identical at the amino acid level compared to At2OGO (SEQ ID NO: 7) (FIG. 2). Two Ob2OGO gDNA sequences were identified (SEQ ID NOS: 4 and 5; FIGS. 3 and 4), each with an intron of different sizes in the middle of the gene. This indicates that there are at least two Ob2OGO genes present in the 'RUSB22-1' genome.

A 23-nt target sequence within ObHSK suitable for gene editing was identified. This sequence contains an ApaI restriction site (italicized) immediately upstream of the AGG PAM site (GCCACCGTCGCCAACTTGGGCCCAGG; SEQ ID NO: 12), representing the target site for Cas9 DNA cleavage. Similarly, a 19-nt Ob2OGO-ApaI target sequence (GCAAAGAAGTTCGGGCCCTGGG; SEQ ID NO: 13) contains an ApaI site 1-nt upstream of the GGG PAM site.

Using this sequence information from 'RUSB22-1', the cDNA, gDNA and protein sequences of HSK and 2OGO were identified in other sweet basil cultivars ('Rutgers Obsession DMR', and 'Rutgers Devotion DMR' (see U.S. Pat. No. 10,159,212). The target sequences of ObHSK and Ob2OGO from 'Rutgers Devotion DMR' and 'Rutgers Obsession DMR' are the same as those from 'RUSB22', indicating the CRISPR-editing vectors provided herein can be used to edit the ObHSK and Ob2OGO genes in basil plants, such as 'RUSB22', 'Rutgers Devotion DMR' and 'Rutgers Obsession DMR'.

Similar methods can be used to identify the cDNA, gDNA and protein sequences of HSK and 2OGO in other sweet basil cultivars (such as 'Rutgers Passion DMR' and 'Rutgers Thunderstuck DMR') and other plants, such as a crop plant (e.g., wheat, corn, grapes).

Reducing or knocking out expression of HSK, 2OGO, or both in plants can be used to improve downy mildew tolerance in plants, such as basil or other plants.

Example 2

Identification of Basil Genes Responsible for Chilling Tolerance

Basil genes that confer susceptibility to chilling have not been reported. Using the NCBI tblastn program with AtMYB14 (NP_180676.1) as the reference, a cDNA sequence from 'RUSB22-1' was identified that encodes the ObMYB14 (SEQ ID NO: 8). The alignment of amino acid sequences show that ObMYB14 (SEQ ID NO: 10) shares 53% identity with AtMYB14 (SEQ ID NO: 11) (FIG. 5). ObMYB14 cDNA (SEQ ID NO: 8) and ObMYB14 gDNA (SEQ ID NO:9) were identified in 'RUSB22'. RT-PCR and 5'-RACE were used with 'RUSB22' mRNA as the template, to clone the ObMYB14 cDNA from nt #70 to the stop codon.

A 23-nt target sequence in the (−) sense strand was identified at the 3' end of the ObMYB14 gDNA (453 nt) for gene editing. This sequence contains a PvuI restriction site (italicized) 1-nt upstream of the CGG PAM site (GACCAGTAACTCTCGTCGATCGTCGG; SEQ ID NO: 14, FIG. 14B). The CRISPR-gene editing vector pRD488 (SEQ ID NO: 21) can edit ObMYB14 at this target site.

Using the sequence information provided herein for 'RUSB22-1', the 3' end of the ObMYB14 gDNAs were identified in other sweet basil cultivars, such as 'Rutgers Obsession DMR' and 'Rutgers Devotion DMR'. These other varieties contain ObMYB14 alleles with target sequences that are identical to the one present in 'RUSB22'. This conservation of gene sequences makes it possible to use the CRISPR-gene editing vector pRD488 to edit ObMYB14 in basil and other plants, such as 'RUSB22', 'Rutgers Obsession DMR' and 'Rutgers Devotion DMR'.

Similar methods can be used to identify the cDNA, gDNA and protein sequences of MYB14 in other sweet basil cultivars (such as 'Rutgers Passion DMR' and 'Rutgers Thunderstuck DMR') and other plants.

Reducing or knocking out expression of MYB14 in plants (e.g., basil) can be used to improve chilling tolerance in plants (e.g., basil).

These results demonstrate the utility of CRISPR-gene editing in enhancing chilling tolerance and resistance can be applied to any plant, including basils and sweet basils (with or without DMR), ornamental basils, Thai basils and also to increase or enhance the resistance of plants that already exhibit some level of chill tolerance or resistance.

Example 3

Basil CRISPR-Gene Editing Vectors

CRISPR-gene editing vector pRD317 for dicotyledonous plants, containing the *Arabidopsis* U6 promoter (SEQ ID NO: 19) to drive the expression of gRNAs ($P_{AtU6}$: gRNA), and vector pRD216, containing the $2XP_{35S}$::hCas9::$T_{NOS}$ cassette, in which expression of humanized Cas9 is under the control of the 2X CaMV 35S promoter and nopaline synthase terminator, were altered.

Figure 14A:
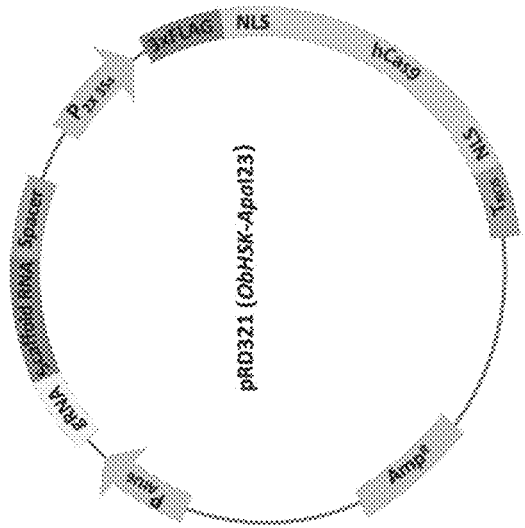
FIGS. 14A-14B: A schematic overview of ObHSK CRISPR-editing vector pRD321 (SEQ ID NO: 15). ObHSK gRNA target SEQ ID NO: 17). (A) Expression of ObHSK-ApaI23 gRNA and the scaffold RNA is driven by the Arabidopsis U6 promoter. The codon-optimized humanized Cas9 (hCas9) gene with 3× FLAG and nuclear localization signal (NLS) is under the control of the 2× CaMV 35S promoter and the nopaline synthase terminator (TNOS). (B) The location of the ObHSK-ApaI23 gRNA target within the 5' region of the ObHSK gDNA is indicated, together with the PCR primer (SEQ ID NO: 12) set used to amplify the region containing and flanking the target site for mutant analysis.
Figure 14B:
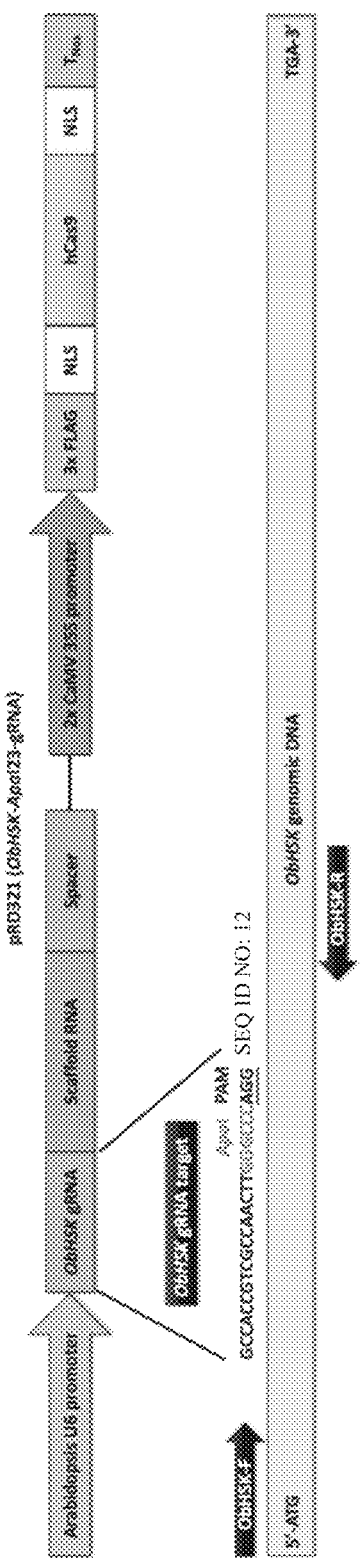

The *Arabidopsis* AtMLO2 gene target sequence in pRD317 was mutated into the ObHSK and Ob2OGO target sequences (SEQ ID NOS: 1 and 4, respectively) as above, resulting in pRD319 ($P_{AtU6}$::ObHSK-ApaI gRNA) and pRD320 ($P_{AtU6}$::Ob2OGO-ApaI gRNA). The vector pRD321 was produced by ligating the $P_{Atu6}$::ObHSK-ApaI gRNA cassette into pRD216 with the Cas9 cassette. Since pRD321 does not have the antibiotic selectable marker and the *Agrobacterium* integrating borders, it can be used for transient (opposed to the use of a stable integrating vector in which the gRNA and Cas9 cassettes are integrated and maintained in the plant host genome) ObHSK gene editing. The pRD321 sequence is provided (SEQ ID NO: 15). A schematic of pRD321 is shown in FIGS. 14A and 14B. The pRD321 transient CRISPR-editing vector was constructed to transiently express the fused ObHSK gRNA and the scaffold RNA from the *Arabidopsis* U6 promoter and the codon-optimized humanized *Streptococcus pyogenes* Cas9 gene driven by the CaMV 2x 35S promoter (FIG. 14A).

Subsequently, the $P_{AtU6}$::ObHSK-ApaI gRNA//2XP$_{35S}$::hCas9::$T_{NOS}$ cassettes were cloned into the plant expression vector pCAMBIA2300, resulting in the integrating vector pRD322 (SEQ ID NO: 20) for ObHSK gene editing. The $P_{AtU6}$: Ob2OGO-ApaI gRNA//2XP$_{35S}$::hCas9::TNOS cassettes were directly cloned into pCAMBIA2300, resulting in the integrating vector pRD327 (SEQ ID NO: 16) for Ob2OGO gene editing.

Example 4

Basil Transformation Methods

Gene-edited basil plants can be generated using the basal leaf section as the explant (Deschamps and Simon, *Plant Cell Rep.*, 21:359-364, 2002; Phippen and Simon, *Cell. Dev. Biol.*, 36:250-254, 2000). To improve the sweet basil transformation efficiency, different sweet basil ('RUSB22') explants including cotyledons, first true leaves, internodes and embryos from mature seeds, were tested for their ability to produce callus and undergo plant regeneration. Different hormonal combinations were also tested. Based on these results, the following transformation and regeneration system for 'RUSB22' was used. Such methods can be used for any basil of interest.

Mature seeds of *O. basilicum* breeding line 'RUSB22' were surface sterilized with a solution of 30% bleach for 30 minutes followed by three 5 minute rinses in sterile distilled water. Embryos were excised from seeds under a dissecting microscope and were sterilized with 10% bleach for 10 min and rinsed with sterile water. These surface sterilized embryos were then used directly for the biolistic transformation. The PDS-1000/He® Particle Delivery System (Bio-Rad Laboratories, 88 Hercules, CA, USA) was used to deliver pRD321 into freshly dissected basil embryos. Approximately 5 µg of pRD321 plasmid DNA was mixed with 2 mg of sterile gold particles suspension in 15 µL of 10 mM Tris (pH 8.0), 150 mM NaCl and vortexed for 10 s. Sixty microliters of DNA binding buffer [0.1 M spermidine, 25% PEG (1300-1600 MW) and 2.5 M CaCl2)] were added to the gold particle/plasmid DNA mixture and vortexed for 10 s, followed by a 10 min incubation at room temperature. DNA/gold particles were pelleted, resuspended in 70% ethanol and distributed onto four microcarrier membranes. Basil embryos were bombarded at 1100 psi and then transferred to sweet basil callus induction medium [Murashige and Skoog (MS) salts, 3% 96 (w/v) sucrose, 0.3% (w/v) Gelzan® gelling agent, 0.4 mg/L 6-benzylami-nopurine (BAP), 0.4 mg/L naphthalene acetic acid (NAA), pH 5.8] and cultured for 4-6 weeks in the dark. Induced somatic embryogenic calli were then transferred to sweet basil regeneration medium [MS salts, 3% (w/v) sucrose, 0.3% (w/v) Gelzan® gelling agent, 2 mg/L BAP, pH 5.8] for shoot induction. Since pRD321 is a transient vector and lacks an antibiotic resistance gene for selection of transformants in plants, antibiotics were omitted from the media. Shoot induction plates were placed under 16h/8h light/dark photoperiod at 22° C. for 4 to 6 weeks. Each regenerated shoot was transferred to rooting medium [MS salts, 3% (w/v) sucrose, 0.3% (w/v)-Gelzan™ Gelzan® gelling agent, 1 mg/L IBA, pH 5.8] for root regeneration, prior to transfer to soil.

Genetic transformation of 'RUSB22' sweet basil with pRD321 was performed by biolistic bombardment on embryo explants derived from mature seeds. One hundred bombarded mature embryos were placed on callus induction medium for two weeks to induce somatic embryogenic calli (FIG. 7A). A total of 88 calli were induced from this transformation event and were transferred to shoot regeneration medium (FIG. 7B). Regenerated shoots were cultured and maintained for about 4-6 weeks (FIG. 7C) before being separated and transferred to root induction medium (FIG. 7D). Twenty-two TO plantlets were regenerated, representing a 5% regeneration rate. All TO plantlets were transferred to soil for further analysis. Eight $T_0$ plantlets, labeled as lines 321-4, 5, 7, 8, 10, 12, 13, 14 established roots in soil and were transferred to the greenhouse.

When pRD327 (SEQ ID NO: 16) was used to target Ob2OGO, 18 plants were regenerated from both gene gun and *Agrobacterium* transformations using approximately 200 embryos and kanamycin in the selective media (FIGS. 8A-8D).

Example 5

Recombinant Basil Mutants

ObHSK and Ob2OGO basil mutants were identified by RFLP (restriction fragment length polymorphism), sequencing, and ICE (Inference of CRISPR Edits) analysis.

It has been shown previously that 43.8% of the regenerated, gene-edited wheat plants generated using a transient vector did not contain the transgene (Zhang et al., *Nature communications* 2016, 7:12617). However, since opportunistic integration of transient CRISPR-gene editing vectors into the plant genome can lead to additional editing in subsequent generations, the genomes of To regenerated plantlets from pRD321 transformation were first verified by PCR using pRD321-specific primers (SEQ ID NOS: 25 and 26) for the presence of plasmid sequences. The $T_0$ lines 321-4, 7, 8 were confirmed to have transgenes integrated into the genome while the remaining lines (321-5, 10, 12, 13, 14) were transgene-free. Vector pRD321, expressing the ObHSK gRNA and Cas9 nuclease, integrated into about 37.5% of the $T_0$ lines constructed via biolistic transformation.

To identify mutants among the regenerated RD321 $T_0$ plants, the 321 bp gDNA fragments spanning the ObHSK target sites were PCR-amplified from RD321 and wild type (WT, untransformed) plant gDNAs. The PCR fragments were digested by ApaI. As shown in FIG. 9A, the ObHSK 321 bp PCR fragment from the WT plant was digested into the 97 bp and 224 bp fragments, as were the PCR fragments amplified from lines RD321-8, 12, 14. A fraction of the ObHSK 321 bp PCR fragments amplified from lines RD321-5, 7, 10, 13 were undigested by ApaI, indicating possible mutations around the gene editing target site in these plants. The PCR amplified fragments were ligated into pGEMT-easy cloning vector, introduced into *E. coli* and the resulting plasmid clones sequenced by Sanger sequencing. The sequencing data of clone RD321-5 indicates that one nucleotide was deleted at the target site, resulting in disruption of the open reading frame (ORF) of the ObHSK gene (FIG. 9B). Sequencing of one clone derived from amplified 'RD321-13' PCR fragments also contained a nucleotide deletion 5' of the target site, leading to premature termination of the encoded ObHSK open reading frame.

Sequencing of one clone from each potential mutant plant's PCR products revealed only a single type of mutation in the potentially mutated allele. Since sweet basil is a tetraploid, gene editing could potentially cause multiple independent mutations at different ObHSK alleles within the same plant cell or cloned lined derived thereof. To elucidate the complete suite of mutations present in RD321-edited plants, the sequencing chromatograms of amplified PCR fragments spanning the ObHSK-ApaI site were analyzed by the Synthego ICE online analysis tool using the chromatogram of the WT PCR fragments as a reference. FIGS. 15A-15B show the inferred CRISPR editing data for lines from the $T_0$ and $T_1$ generations. $T_0$ lines RD321-5, 7, 8, 10, 13, 14 have four different types of editing patterns with respective cumulative Indel frequencies at 21%, 22%, 19%, 21%, 19%, 22% and 20%. The inferred Indel types include two deletion events (−1 nt and −13 nt) which result in frameshifting mutations and two insertion events (+6 nt and +15 nt) which result in amino acid additions. Line RD321-12 was predicted to also carry the −1 nt, −13 nt, +6 nt and +15 nt edited types, as well as three additional deletion types at −2 nt, −10 nt and −24 nt, representing 22% of all Indels. Deletions of 2 nt and 10 nt are frameshifting mutations while deletion of 24 nt results in the net loss of 8 amino acids. Lines 321-5 and 321-13 were chosen for propagation to the $T_1$ generation, due to their having the highest frequency (22%) of Indels and the absence of pRD321 sequences from the genome. Line RD321-12 also has 22% Indels and displays a more diverse editing pattern but was not chosen for $T_1$ segregation because of growth retardation and sterility observed in the To generation.

Figure 10:
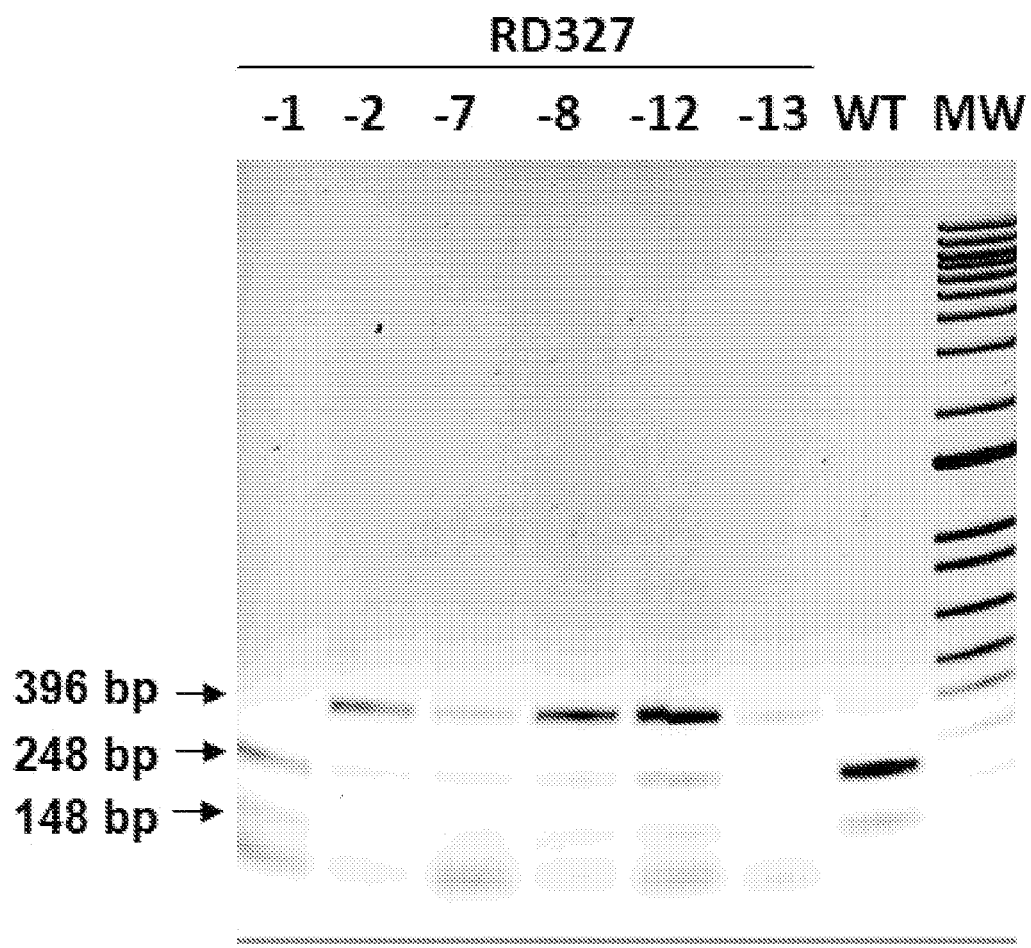
FIG. 10: Identification of RD327 mutants. RFLP analysis of the 396 bp PCR fragments spanning the target site by ApaI. MW, molecular weight marker. WT, wild type plant.

Thirty seeds derived from each of the $T_0$ lines RD321-5 and RD321-13 were germinated and propagated and the resulting $T_1$ plants were inoculated with P. belbahrii to assess their DM resistance. Thirty WT plants were also inoculated as controls. Symptoms on some RD321-5 and RD321-13 lines were similar to those seen for WT plants, possibly reflecting the segregation of edited alleles in the $T_1$ generation. $T_1$ plants that exhibited reduced DM symptoms were genotyped and analyzed as above. These plants included RD321-5-1, 2, 5, 7, 8, 9 and RD321-13-1, 2, 3, 4, 5, 9. These $T_1$ plants were confirmed by PCR to be transgene-free, as were the To parental plants. PCR-sequencing and ICE analysis revealed that 7 out of 12 $T_1$ ObHSK-edited plants, RD321-5-2, 5, 7, 8 and RD321-13-3, 4, 5, retained the same ObHSK editing patterns as their parental $T_0$ plants, with Indel frequencies ranging between 20-22%. The remaining 5 $T_1$ lines RD321-5-1, 9 and RD321-13-1, 2, 9 exhibited diverse editing patterns. Line RD321-5-1 has 33% Indels with three distinct editing patterns (−15 nt, −18 nt, +1 nt) which result in the loss of 5 and 6 amino acids as well as other frameshifting mutations. Line RD321-5-9, which has 20% Indels, retained the same editing patterns as RD321-5 but with an additional 16 nt deletion that would cause a frameshifting mutation. Lines RD321-13-1, 2, 9 with 19, 17, 18% Indel frequencies respectively, shared some similar editing patterns. These three lines respectively contain −1 nt, −10 nt and −13 nt deletions, all of which result in frameshifting mutations. Lines RD321-13-1 and RD321-13-9 also retained the same insertion patterns (+6 nt and +15 nt) as the RD321-13 To parental plant. There was an additional editing pattern of −24 nt for lines RD321-13-1 and RD321-13-2, resulting in the net loss of 6 amino acids. RFLP analysis (FIG. 10) by ApaI on the pRD327-regenerated $T_0$ plants showed that the WT 396 bp PCR product was digested into the 148 bp and 248 bp fragments. However, the 396 bp products from 'RD327'-2, 7, 8, 12, and 13 were partially digested, indicating that these plants are mutated in the Ob2OGO gene.

The mutation patterns and the Indel frequencies observed in RD321 $T_0$ and $T_1$ plants indicate that they are heterozygous, as expected for a polyploid plant such as sweet basil. To $T_1$ plants retained 60-70% of the WT ObHSK sequence in their genomes, as inferred by ICE analysis. Since SB22 sweet basil is tetraploid, the ObHSK-ApaI gRNA target was expected to produce multiple mutation patterns in the To generation. These results revealed, respectively, that there were two types of insertion and deletion events in the $T_0$ plants, with the exception of line 321-12. Both types of deletion (−1 nt and −13 nt) within the ObHSK gene led to frameshifting mutations and the presumed disruption of the functional domain of ObHSK. In contrast, the insertional mutations observed (+6 nt and +15 nt) would have added extra amino acids while preserving the reading frame and may or may not have disrupted the function of the encoded ObHSK protein.

Most of the $T_1$ plants retained mutations inherited from their parents (FIGS. 15A-15B). $T_1$ plants displayed more frameshifting mutations and larger polypeptide deletions (>=5 amino acids), compared to their respective parental plants.

Example 6

Recombinant Basil Mutants Resistant to DM

The ObHSK mutants were tested for DM resistance. Briefly, 'RD321-5' and 'RD321-13' Ti plants were germinated and grown in the greenhouse. When the third set of true leaves emerged, P. belbahrii spore inoculum collected from the field was sprayed onto the plants which were then cultured in the greenhouse and scored as previously published (Pyne et al., HortSci. 49:1041-5, 2014). 15-20 plants each from 'RD321-5', 'RD321-13' and WT were inoculated in each batch. Levels of pathogen DNA present inside leaves, representing colonization of host tissues, were quantitated by qPCR at 5 days post-inoculation.

P. belbahrii sporangia spores were prepared by agitating freshly sporulating leaves of infected plants in distilled water for 30 min, filtered through a 40 µm nylon mesh cell using 50 mL of distilled water, counted in a hemocytometer and adjusted to 5×104 spores mL-1. The spore solution was spray-inoculated onto plants using a Preval pressure sprayer. Inoculated plants were incubated in a dew chamber for two days, which was maintained at 100% relative humidity and leaf wetness using Trion 707U series atomizing humidifiers (Trion, Sanford, NC, USA). Leaf samples were collected 5 days after inoculation. Qualitative assessment of disease progression was performed visually using an established disease severity index to compare symptoms of WT, TO and $T_1$ ObHSK-edited plants. Pictures were taken 15 days post-inoculation (dpi). Quantitative analysis of P. belbahrii levels in planta was performed by qPCR using β-tubulin as the plant endogenous gene and the ITS2 gene sequence for the pathogen. Primers for each gene were designed using the Primer Express® oligonucleotide design software (Applied Biosystems, Foster City, CA, USA). All samples were analyzed by SYBR green qPCR which was run on the default setting at 95° C. for 3 minutes for the initial denaturation and 40 cycles at 95° C. for 30 s followed by 60° C. for 30 s with the StepOne® real-time PCR instrument (Applied Biosystems, Foster City, CA, USA). The fold-change of gene expression was calculated by the 2-ΔΔCt method and the qPCR analysis was performed in triplicate for each sample using three different leaf samples.

gDNAs of all samples were extracted using the GenElute™ Plant Genomic DNA Miniprep Kit (Sigma-Aldrich, St. Louis, MO, USA). The DNA concentration for each sample was measured with a NanoDrop/2000® spectrophotometer (Thermo Fisher, Waltham, MA, USA). All T0 and T$_1$ plants were verified for the presence of the transgene (plasmid sequence of pRD321) using the primers RD321-F and RD321-R (SEQ ID NOS: 25 and 26) that flank the sequence between the AtU6 promoter and the 35S promoter. The 321 bp gDNA fragment flanking the gRNA target site was amplified using the primer pair ObHSK-F and ObHSK-R. PCR products were purified using the GeneJET® Gel Extraction Kit (Thermo Fisher, Waltham, MA, USA), prior to Sanger sequencing by Genewiz, Inc. The DNA sequencing chromatogram data for each T0 and T$_1$ sample was analyzed using the Inference of CRISPR Editing (ICE) software tool (Synthego Performance Analysis, ICE Analysis. 2019. v2.0. Synthego) to predict the nature and efficiency of gene editing events.

Figure 11:
FIG. 11: Greenhouse testing of RD321-5 and RD321-13 $T_1$ plants for DM resistance. Symptoms were recorded 15 days post P. belbahrii inoculation (dpi).

FIG. 11 shows the phenotype of representative RD321-5 and RD321-13 T$_1$ plants in comparison to the *P. belbahrii*-inoculated WT plants at 15 days post inoculation. The T$_1$ ObHSK-edited plants from both lines appeared greener than the *P. belbahrii*-inoculated WT plants and lacked the visual DM disease symptoms of leaf chlorosis apparent in *P. belbahrii*-inoculated WT plants 15 days post inoculation. RD321-13 T$_1$ plants performed better than did RD321-5 plants with a higher proportion of RD321-13 plants exhibiting healthier growth appearance than RD321-5 plants.

Figure 12:
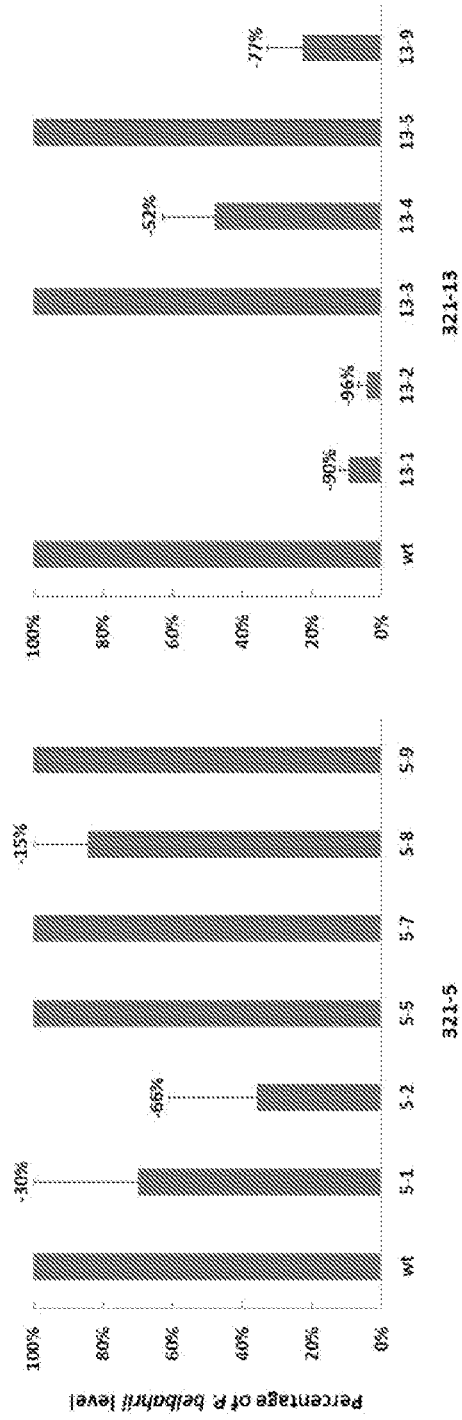
FIG. 12: qPCR analysis to assess the Peronospora belbahrii pathogen levels in individual $T_1$ plants 5 dpi. P. belbahrii ITS2-specific primers as well as basil β-tubulin gene-specific primers were used to determine $2^{-\Delta\Delta Ct}$ relative levels of the pathogen. Pathogen reduction in $T_1$ plants was calculated as a percentage compared to WT plants (assessed as 100% each time) and averaged from three separate qPCR assays, with standard deviations indicated.

Quantitative PCR (FIG. 12) was performed on six phenotypically more resistant T$_1$ ObHSK-edited plants from each of the RD321-5 and RD321-13 lines. The T$_1$ plants from RD321-5-1, 2, 8 lines showed 30, 66, 15% reductions of *P. belbahrii*, respectively, within the inoculated leaves, compared to *P. belbahrii*-inoculated WT plants. In contrast, T$_1$ plants from RD321-5-5, 7, 9 lines contained levels of *P. belbahrii* DNA that were comparable to those observed in *P. belbahrii*-inoculated WT plants. T$_1$ plants from RD321-13-1, 2, 4, 9 lines showed 90, 96, 52, 77% reductions, respectively, in their in planta *P. belbahrii* levels, while T$_1$ plants from RD321-13-3 and RD321-13-5 lines had similar pathogen levels as *P. belbahrii*-inoculated WT plants. All twelve T$_1$ plants first developed disease symptoms 25 days post inoculation while *P. belbahrii*-inoculated WT plants first displayed disease symptoms at 10 days post-inoculation.

Figure 13A:
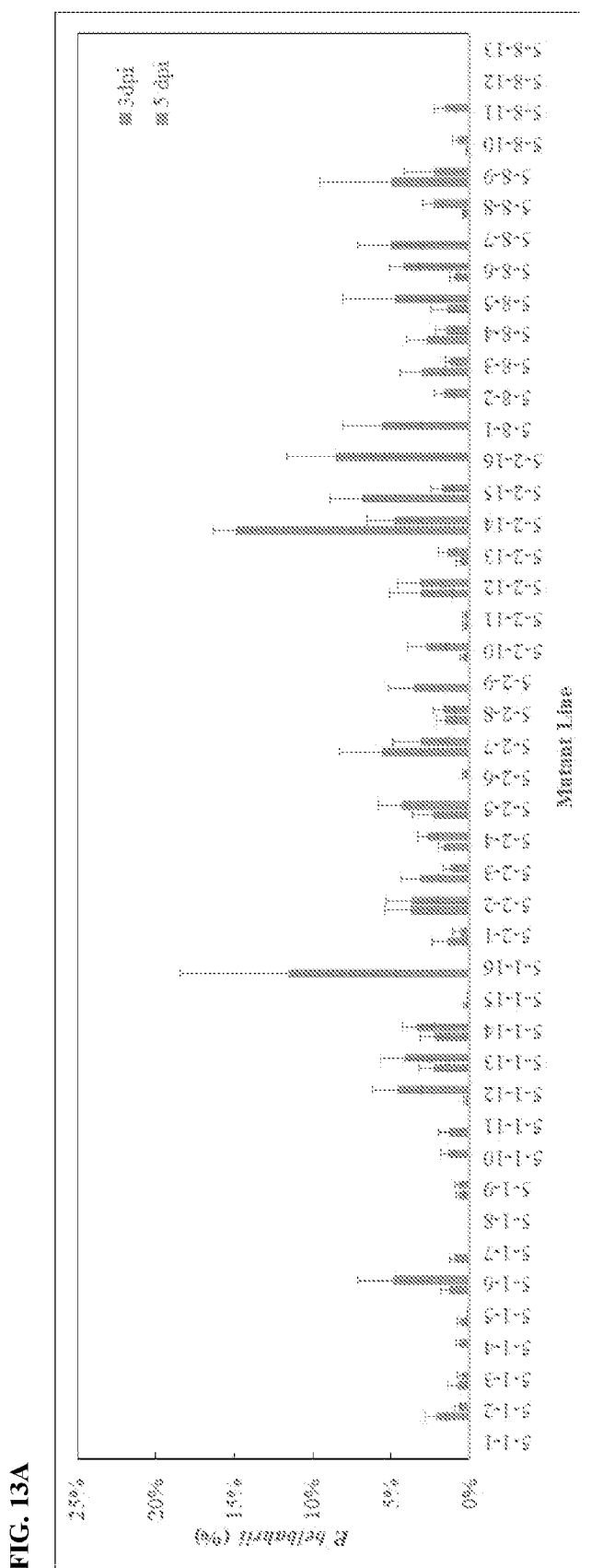
FIGS. 13A-13B: qPCR analysis to assess the Peronospora belbahrii pathogen levels in inoculated $T_2$ plants from RD321-5-1, 2, 8 and RD321-13-1, 2, 9 lines. Plants were assayed 3 and 5 days post inoculation (dpi). The P. belbahrii levels in inoculated plants were assessed by comparing to the averaged levels in sixteen inoculated WT plants which were set to 100%.
Figure 13B:
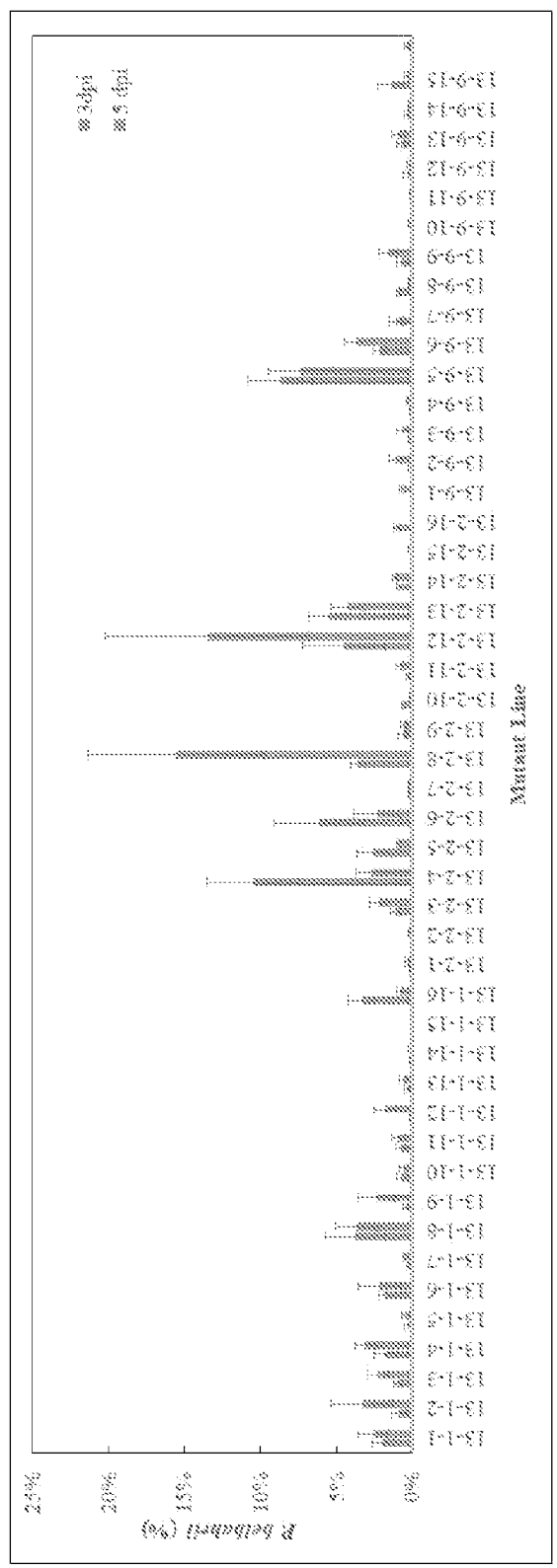

Seeds from RD321-5-1, 2, 8, and RD321-13-1, 2, 9 T$_2$ lines were germinated. Sixteen plants from each line and the WT were inoculated with *P. belbahrii* in the greenhouse. The pathogen levels were assayed by qPCR at 3, 5 days post inoculation (dpi). Our results (FIGS. 13A-13B) show that all the inoculated RD321 T$_2$ plants had substantially reduced levels of *P. belbahrii*, compared to *P. belbahrii*-inoculated WT plants within 5 days of the initial infection, with the RD321 T$_2$ plants displaying between 0 and 15% of the pathogen load, compared to similarly inoculated WT plants.

Thus, it is shown that a number of T$_1$ ObHSK-edited sweet basil plants were more highly resistant to DM than were WT plants. Visual assessment of ObHSK-edited 321-5 and 321-13 T$_1$ plants showed that the resistant plants were greener in appearance compared to WT plants at 15 days post-inoculation (FIG. 11). This indicates that the partially edited HSK gene may have slowed down disease progression or attenuated pathogen virulence. qPCR analysis revealed a marked reduction of the pathogen load in 321-5-1, 2, 8 and 321-13-1, 2, 4, 9 T$_1$ plants, particularly in lines 321-13-1 and 321-13-2, which showed up to 90% 293 and 96% reductions, respectively. No such reduction was observed in any of the WT plants.

The tetraploid nature of sweet basil was reflected in the multiple Indel patterns observed within ObHSK gene in both T$_0$ and T$_1$ plants. The stunted and sterile phenotype displayed in the 321-12 T$_0$, indicates that ObHSK may play a role in normal growth and development.

Figure 16A:
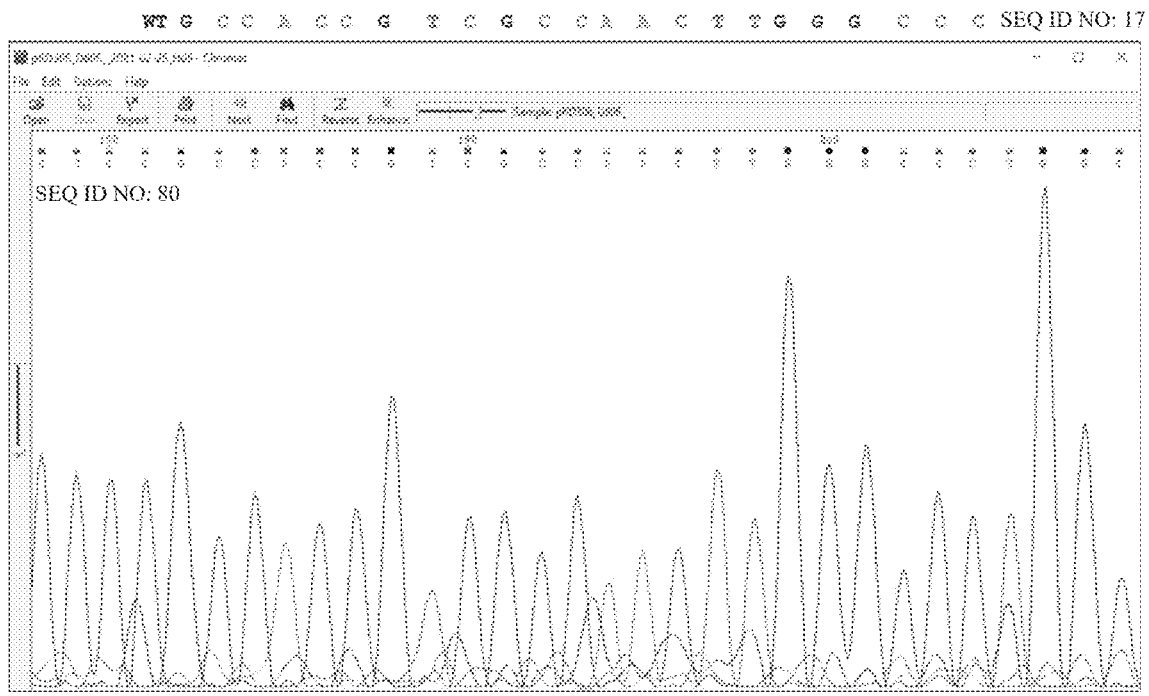
FIGS. 16A-16C: Sequencing chromatograms of ObHSK gDNA PCR fragments (321 bp) from (A) WT (SEQ ID NO: 17), (B) 321-5-2-12 $T_2$ (SEQ ID NO: 78) and (C) 321-5-8-1 $T_2$ (SEQ ID NO: 79) plants that span the ApaI target site. WT and the possible sequences from the mutants are shown above the chromatograms. The mutated sequences do not necessarily represent a single mutated allele of ObHSK from the mutant plants.
Figure 16B:
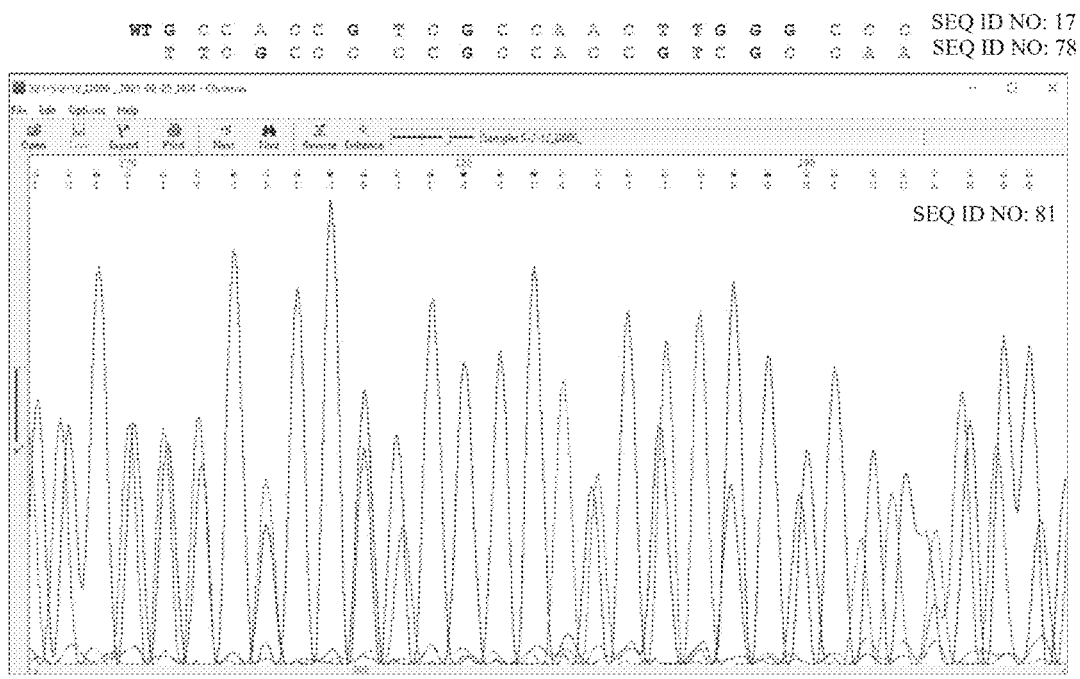
Figure 16C:
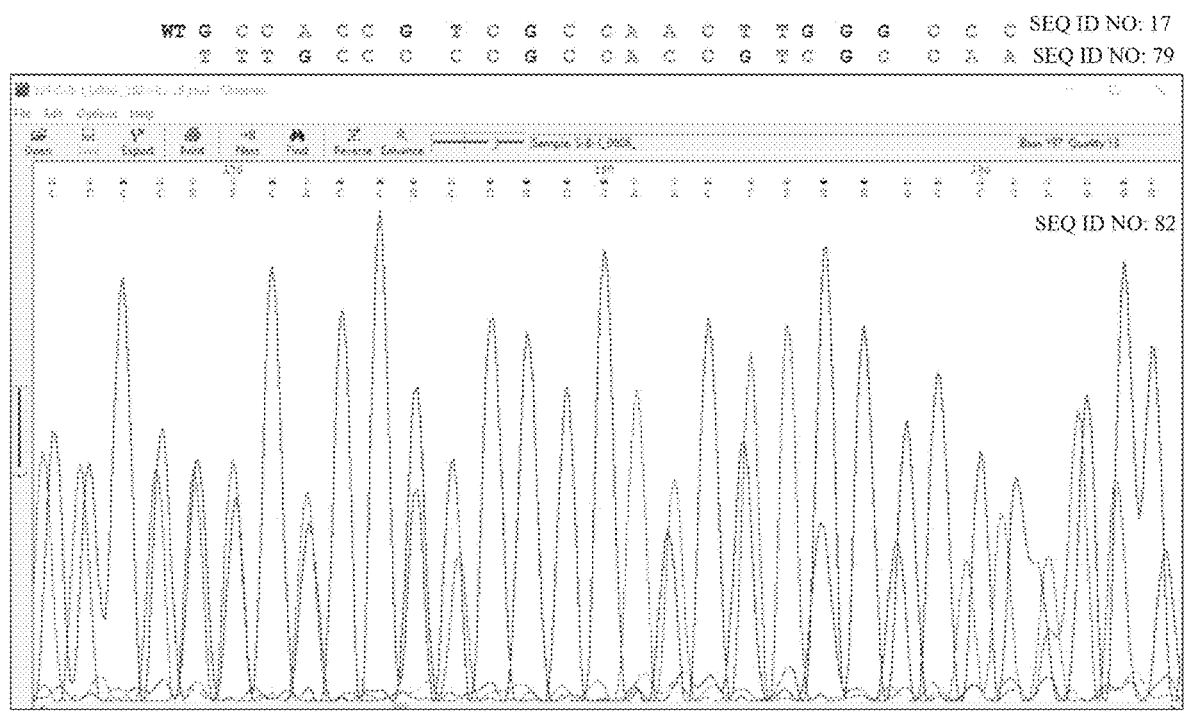

Two T$_2$ plants, 321-5-2-12 and 321-5-8-1, displayed the highest resistance in the inoculation assay, with the lowest disease rating even after 5 dpi. gDNAs from these two plants and the WT plant were extracted, the 321 bp gDNA fragments were PCR-amplified. The PCR fragments were sequenced with the forward primer. The sequencing scores of WT, 321-5-2-12 and 321-5-8-1 were not high enough to be analyzed by the Synthego online ICE tool. However, the sequencing chromatograms clearly indicate that some of the ObHSK alleles are mutated. As the WT chromatogram shows in FIG. 16A, the WT target sequence GCCACCGTCGCCAACTTGGGCCC (SEQ ID NO: 17) has distinct peaks at every nucleotide. The 321-5-2-12 and 321-5-8-1 chromatograms in FIGS. 16B-16C show, however, besides the clear WT sequence, both mutants also have distinct second peaks in most of the nucleotides, which most likely resulted from the amplified mutated alleles with Indels, transitions or transversions.

The data provided in the Examples demonstrate the utility of CRISPR-gene editing in enhancing DM resistance. Thus, such methods can be applied to DM susceptible plants (e.g., sweet basil varieties, ornamental basils, Thai basils) and to increase or enhance the resistance of DM in plants that already exhibit some level of tolerance to resistance.

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

We claim:

1. A method for increasing *Peronospora belbahrii* resistance in an *Ocimum* spp. basil plant, plant part, or cell, comprising:
   introducing (i) a gRNA comprising SEQ ID NO: 17, and (ii) a Cas9 protein or gene into the *Ocimum* spp. basil plant, plant part, or cell, thereby generating a gene-edited plant, plant part, or cell;
   wherein the *Ocimum* spp. basil plant, plant part, or cell comprises a HSK gene comprising at least 95% identity to SEQ ID NO: 1, and the HSK gene comprises SEQ ID NO: 17 adjacent to a PAM site; and
   the gene-edited plant, plant part, or cell has increased resistance to *Peronospora* belbahrii in comparison to a wild type plant, plant part, or cell.

2. The method of claim 1, wherein the gene-edited plant, plant part, or cell is morphologically indistinguishable from the wild-type plant, plant part, or cell.

3. The method of claim 1, wherein the gRNA consists of SEQ ID NO: 17.

4. The method of claim 1, wherein the *Ocimum* spp. is *O. basilicum, O. ×citriodorum, O. basilicum ×O. kilimandscharicum, O. basilicum ×O. americanum, O. kilimandscharicum, O. africanum, O. americanum, O. tenuiflorum, O. gratissimum,* or *O. minimum.*

5. The method of claim 1, wherein the *Ocimum* spp. is *O. basilicum, O. ×citriodorum, O. basilicum ×O. kilimandscharicum,* or *O. basilicum× O. americanum.*

6. The method of claim 1, wherein the *Ocimum* spp. is *O. basilicum* or *O. ×citriodorum.*

7. The method of claim 6, wherein the *O. basilicum* is *O. basilicum* L. or *O. basilicum* var. *thyrsiflora.*

8. The method of claim 1, wherein the HSK gene comprises at least 98% identity to SEQ ID NO: 1.

9. The method of claim 1, wherein the HSK gene comprises SEQ ID NO: 1.

10. The method of claim 1, wherein the gRNA, the Cas9, or both the gRNA and the Cas9, are comprised on a vector.

11. The method of claim 10, wherein the vector is a plasmid.

12. The method of claim 11, wherein the plasmid is a non-integrating plasmid.

13. The method of claim 12, wherein the non-integrating plasmid is a transient expression vector.

14. The method of claim 10, wherein both the gRNA and the Cas9 are comprised on a vector, and the vector comprises SEQ ID NO: 15.

15. The method of claim 1, wherein the gRNA and the Cas9 are comprised in a ribonucleoprotein complex.

16. The method of claim 1, wherein the plant part or cell comprises a protoplast, leaf, stem, root, anther, pistil, stamen, seed, embryo, pollen, ovule, microspore, sporophyte, gametophyte, cotyledon, hypocotyl, flower, shoot, tissue, petiole, or meristematic cell.

17. A gene-edited plant, plant part, or cell produced by the method of claim 1, wherein the gene-edited plant, plant part, or cell comprises the gRNA comprising SEQ ID NO: 17.

* * * * *

SEQUENCE LISTING

<160> NUMBER OF SEQ ID NOS: 82

<210> SEQ ID NO 1
<211> LENGTH: 1137
<212> TYPE: DNA
<213> ORGANISM: Ocimum basilicum

<400> SEQUENCE: 1
atggccgccg tctgcctgaa gctcaacttc gccgccgccg ccgccgcctc cgcctccgca      60
accaccgtcg ccaacctatc atcaccaaag ccccaaaccc acttaagatt caacccatcc     120

```
gcatccgcac tatcaacatc cgcttattcc aaatccactg agcctctacc cgtcttctcc    180
tccgtcaaat ctttcgcccc cgccaccgtc gccaacttgg ccctggctt cgactttctg    240
ggatgcgccg tagacggaat cggcgactac gtcagcctcc gagtcgatcc agacgtgcac    300
cccggcgaag tttccatttc caacatcacc gggcggacaa cgtggcgccg tcgatcttgg    360
gaggtttcgt tttgatacgc agctacgacc ctttggaact gatgcaacta aagtttcccc    420
atgagaaaag cttgtatttc gtgctggtga atccggaatt cgaagcccca acgaagaaga    480
tgagagcggc gttgccgcag gaaatcacga tgtcgcacca catatggaat ccagccaag    540
ctggggcttt ggttgcgtct gttttgcaag gcgatctcgt tgggttagga aaggcgctgt    600
catcggataa gattgtggag ccgaagaggg ctccctttgat tccgggcatg gaagctgtga    660
agaaagctgc catcgcagca ggggcgtttg gttgcacgat aagtggagct ggaccaactg    720
cggtggcggt gacagacagt gaggaaaaag gtagagaaat tggggagaaa atggtggagg    780
cttttgagaa agaagggaac ttgaaggctt tggcaatggt gaggcagctt gatagagttg    840
gagctaggct tgtcagcagt gttcccagat gacgccggcc ccaagctcag caagaacccc    900
ctttggaatt cgccggcat cgccgccatc gccgtcatga aaatgctcag catccgctcc    960
gtgggtctct cgctctctct cgaaaagggc ctccctctgg gcagcggcct cggctccagc   1020
gcggccagcg ccgccgcagc tgctgtcgct gtaaacgagt tgttcggggg tcctctgtcg   1080
ccgtcagaac tcgtgttcgc cggtctggag tctgaggcga aggtctccgg ctaccac      1137
```

<210> SEQ ID NO 2
<211> LENGTH: 378
<212> TYPE: PRT
<213> ORGANISM: Ocimum basilicum

<400> SEQUENCE: 2

```
Met Ala Ala Val Cys Leu Lys Leu Asn Phe Ala Ala Ala Ala Ala
1               5                   10                  15

Ser Ala Ser Ala Thr Thr Val Ala Asn Leu Ser Ser Pro Lys Pro Gln
            20                  25                  30

Thr His Leu Arg Phe Asn Pro Ser Ala Ser Ala Leu Ser Thr Ser Ala
        35                  40                  45

Tyr Ser Lys Ser Thr Glu Pro Leu Pro Val Phe Ser Ser Val Lys Ser
    50                  55                  60

Phe Ala Pro Ala Thr Val Ala Asn Leu Gly Pro Gly Phe Asp Phe Leu
65                  70                  75                  80

Gly Cys Ala Val Asp Gly Ile Gly Asp Tyr Val Ser Leu Arg Val Asp
                85                  90                  95

Pro Asp Val His Pro Gly Glu Val Ser Ile Ser Asn Ile Thr Gly Ala
            100                 105                 110

Gly Ser Lys Leu Ser Lys Asn Pro Leu Trp Asn Cys Ala Gly Ile Ala
        115                 120                 125

Ala Ile Ala Val Met Lys Met Leu Ser Ile Arg Ser Val Gly Leu Ser
    130                 135                 140

Leu Ser Leu Glu Lys Gly Leu Pro Leu Gly Ser Gly Leu Gly Ser Ser
145                 150                 155                 160

Ala Ala Ser Ala Ala Ala Ala Val Ala Val Asn Glu Leu Phe Gly
                165                 170                 175

Gly Pro Leu Ser Pro Ser Glu Leu Val Phe Ala Gly Leu Glu Ser Glu
            180                 185                 190

Ala Lys Val Ser Gly Tyr His Ala Asp Asn Val Ala Pro Ser Ile Leu
```

```
                195                 200                 205
Gly Gly Phe Val Leu Ile Arg Ser Tyr Asp Pro Leu Glu Leu Met Gln
    210                 215                 220

Leu Lys Phe Pro His Glu Lys Ser Leu Tyr Phe Val Leu Val Asn Pro
225                 230                 235                 240

Glu Phe Glu Ala Pro Thr Lys Lys Met Arg Ala Ala Leu Pro Gln Glu
                245                 250                 255

Ile Thr Met Ser His His Ile Trp Asn Ser Ser Gln Ala Gly Ala Leu
                260                 265                 270

Val Ala Ser Val Leu Gln Gly Asp Leu Val Gly Leu Gly Lys Ala Leu
            275                 280                 285

Ser Ser Asp Lys Ile Val Glu Pro Lys Arg Ala Pro Leu Ile Pro Gly
        290                 295                 300

Met Glu Ala Val Lys Lys Ala Ala Ile Ala Ala Gly Ala Phe Gly Cys
305                 310                 315                 320

Thr Ile Ser Gly Ala Gly Pro Thr Ala Val Ala Val Thr Asp Ser Glu
                325                 330                 335

Glu Lys Gly Arg Glu Ile Gly Glu Lys Met Val Glu Ala Phe Glu Lys
                340                 345                 350

Glu Gly Asn Leu Lys Ala Leu Ala Met Val Arg Gln Leu Asp Arg Val
            355                 360                 365

Gly Ala Arg Leu Val Ser Ser Val Pro Arg
        370                 375

<210> SEQ ID NO 3
<211> LENGTH: 370
<212> TYPE: PRT
<213> ORGANISM: Arabidopsis thaliana

<400> SEQUENCE: 3

Met Ala Ser Leu Cys Phe Gln Ser Pro Ser Lys Pro Ile Ser Tyr Phe
1               5                   10                  15

Gln Pro Lys Ser Asn Pro Ser Pro Leu Phe Ala Lys Val Ser Val
            20                  25                  30

Phe Arg Cys Arg Ala Ser Val Gln Thr Leu Val Ala Val Glu Pro Glu
        35                  40                  45

Pro Val Phe Val Ser Val Lys Thr Phe Ala Pro Ala Thr Val Ala Asn
    50                  55                  60

Leu Gly Pro Gly Phe Asp Phe Leu Gly Cys Ala Val Asp Gly Leu Gly
65                  70                  75                  80

Asp His Val Thr Leu Arg Val Asp Pro Ser Val Arg Ala Gly Glu Val
                85                  90                  95

Ser Ile Ser Glu Ile Thr Gly Thr Thr Lys Leu Ser Thr Asn Pro
            100                 105                 110

Leu Arg Asn Cys Ala Gly Ile Ala Ala Ile Thr Met Lys Met Leu
        115                 120                 125

Gly Ile Arg Ser Val Gly Leu Ser Leu Asp Leu His Lys Gly Leu Pro
    130                 135                 140

Leu Gly Ser Gly Leu Gly Ser Ser Ala Ala Ser Ala Ala Ala Ala
145                 150                 155                 160

Val Ala Val Asn Glu Ile Phe Gly Arg Lys Leu Gly Ser Asp Gln Leu
                165                 170                 175

Val Leu Ala Gly Leu Glu Ser Glu Ala Lys Val Ser Gly Tyr His Ala
            180                 185                 190
```

```
Asp Asn Ile Ala Pro Ala Ile Met Gly Gly Phe Val Leu Ile Arg Asn
            195                 200                 205

Tyr Glu Pro Leu Asp Leu Lys Pro Leu Arg Phe Pro Ser Asp Lys Asp
    210                 215                 220

Leu Phe Phe Val Leu Val Ser Pro Asp Phe Glu Ala Pro Thr Lys Lys
225                 230                 235                 240

Met Arg Ala Ala Leu Pro Thr Glu Ile Pro Met Val His His Val Trp
                245                 250                 255

Asn Ser Ser Gln Ala Ala Ala Leu Val Ala Ala Val Leu Glu Gly Asp
            260                 265                 270

Ala Val Met Leu Gly Lys Ala Leu Ser Ser Asp Lys Ile Val Glu Pro
        275                 280                 285

Thr Arg Ala Pro Leu Ile Pro Gly Met Glu Ala Val Lys Lys Ala Ala
    290                 295                 300

Leu Glu Ala Gly Ala Phe Gly Cys Thr Ile Ser Gly Ala Gly Pro Thr
305                 310                 315                 320

Ala Val Ala Val Ile Asp Ser Glu Glu Lys Gly Gln Val Ile Gly Glu
                325                 330                 335

Lys Met Val Glu Ala Phe Trp Lys Val Gly His Leu Lys Ser Val Ala
            340                 345                 350

Ser Val Lys Lys Leu Asp Asn Val Gly Ala Arg Leu Val Asn Ser Val
        355                 360                 365

Ser Arg
    370

<210> SEQ ID NO 4
<211> LENGTH: 1847
<212> TYPE: DNA
<213> ORGANISM: Ocimum basilicum
<220> FEATURE:
<221> NAME/KEY: misc_feature
<222> LOCATION: (848)..(848)
<223> OTHER INFORMATION: n is a, c, g, or t
<220> FEATURE:
<221> NAME/KEY: misc_feature
<222> LOCATION: (916)..(916)
<223> OTHER INFORMATION: n is a, c, g, or t
<220> FEATURE:
<221> NAME/KEY: misc_feature
<222> LOCATION: (956)..(956)
<223> OTHER INFORMATION: n is a, c, g, or t

<400> SEQUENCE: 4
atggaaacga aggtcattag tggaacacag ttcgcaagcc tgccgagttg ctatgtccgt    60
ccagaatccg agaggcctaa gttatctgaa gttgctgatt gcgaagatgt tcccgtcatt   120
gatttgggct gcggagatcg tagcctgata gtcaaacaga tcggtgatgc ttgtcgagaa   180
tatggatttt tccaggttac ttaatgtttg aacgtacctc agctactcgt tgaaccacta   240
gtccaagtgc tgatttcgtt tcctcttttg gatgtattct gtcaggtgat caatcatgcc   300
gtgccgaaag acatagtgga taaatggtg ggggtggcgc atgaattctt cagtctatct   360
gtggaggaga agatgaaatt atactctgat gaccccttcaa aaacgatgcg actctctacg   420
agtttcaacg ttagaaagga gaccgttcac aactggagag actatctcag gcttcattgc   480
taccccttgg agaaatacgc gcctgaatgg ccgtctaatc cctcttcttt caagtaagcc   540
aacctgtttt cttagtagtg ccagcaaaag attgttgata tgaatcgcat tttcatttgt   600
agggatatcg taagcacata ctgcaaagaa gttcgggccc tgggattctg gttgcaagag   660
gccatatcgg agaacctcgg tttacacaaa gactgcctca gaatgtatt gggagagcaa   720
```

```
gggcaacaca tggccatcaa cttctatcct gcatgcccag aaccagatct gactttcgga    780
ttacccgctc atacagatcc gaatgcgctc accattctcc ttcaagattt actggtttcg    840
ggtcttcngg ttctcaaggg atgggaaatg gttagcaata agccccagc cagatgcttt     900 tgtcatcaac attggngatc aaatccaggt gaacactatg gaaaatgcat tgtgnccct     960 ttgcccacaa aaactgcgat tcgggtaaga tttaggggaa agaggatgaa tcatcatctt   1020
actgtttcac gaattagggg attttatccc accatttgaa gttggggtaa attatcctat   1080
agtttatttc cattagagta ttttaccctc cgtgaataac gatgtcaact gttttgtcac   1140
gtcacacctt taattcccgc gtggaaaaaa ataattcttt tttccagggt attggacgaa   1200
aataaaatcg ttttgtttaa cgtcgtccct aatatcgatt tatgggaaat tcaggaaaat   1260
tatccgttct cacaagtcat gttccaacgt ttccattaat atgggttgaa ctgcgtcgtt   1320
ttcgttcaat gcccttaaaa taaagaactt aatatttttt ccacgctggc atttaacgtg   1380
tgaagtaacg aatgtttgac atagtcatac atggaggata gaatacccta aaaatcccct   1440
gagaagtgaa acagtaagat aacttaccct tcacgattcg tcgtgtgttt tcagatcgga   1500
ggagcattgc tctttatatc tactgaacaa acttatcagt tcagatgcat aagaaaaaca   1560
gttttagcat ctccttactg aactatctgt gcaactcact tccggcattc agtaatggga   1620
agtacagaag cgtgtggcat cgagctgtcg taaattcgaa caaagccaga ctctcggtcg   1680
cttcattcct ctgcccgtgc gatgcagcaa atatcagcgc tccaaatgaa cttacaaccg   1740
gcgatgatcg agcaatatac agaggtttta catatgccga gtactacaaa aagttctgga   1800
gccggaacct ggatcaggag cactgcctgg aactattcaa gaattag                 1847

<210> SEQ ID NO 5
<211> LENGTH: 1557
<212> TYPE: DNA
<213> ORGANISM: Ocimum basilicum

<400> SEQUENCE: 5
atggaaacga aggtcattag tggaacacag ttcgcaagcc tgccgagttg ctatgtccgt     60
ccagaatccg agaggcctaa gttatctgaa gttgctgatt gcgaagatgt tcccgtcatt    120
gatttgggct gcggagatcg tagcctgata gtcaaacaga tcggtgatgc ttgtcgagaa    180
tatggatttt tccaggttac ttaatgtttg aacgtacctc agctactcgt tgaaccacta    240
gtccaagtgc tgatttcgtt tcctcttttg gatgtattct gtcaggtgat caatcatgcc    300
gtgccgaaag acatagtgga taaaatggtg ggggtggcgc atgaattctc cagtctatcc    360
gtggaggaga agatgaaatt atactctgat gacccttcca aaactatgcg actctccacg    420
agtttcaacg ttagaaagga gaccgtacac aactggagag actatctcag gcttcactgt    480
taccccttgg agaaatacgc gcctgaatgg ccatctaatc cctcttcttt caagtaagcc    540 aacctgttt cttagtagtg ccagcaagag atttttgaga tgaatcgtat ttcatttgt     600 agggatatcg taagcacata ctgcaaagaa gttcgggccc tgggattctg gttgcaagag    660
gccatatcgg agagcctcgg tttacacaaa gactgcctca agaatgtatt gggagagcaa    720
gggcaacata tggccatcaa ctttttatcct gcatgcccag aaccagatct gactttcgga    780
ttacccgctc atacagatcc gaatgcactc gccattctcc ttcaagattt actggtttcg    840
ggtcttcagg ttctcaagga tgggaaatgg ttagcaataa agcccggcc agatgctttt     900 gtcatcaaca ttggtgatca aatccaggtg accactattt gtacaattgt tatgtaagaa   960
```

-continued

```
tgcccttat ggaaaactgc gattcgggta agatctaggg gaaagaggat gaatccttgt    1020
cttactgttt cacgaattag gggattttat cccacaattt cgttcaatgc cctaaaaata    1080
aagaaattaa tattttttcca cgctggaatt taatgtgtga agtaaaaaat atttgacatc   1140
gtcattcatg gggtgaaaca gtaagataac ttacccttca tgattcgtcg tgttttttca    1200
gatcggagga gcatggctct ttttatctac tgaacaaact tatcagttca gatgcataag    1260
aaaaactatt ttagcatctc cttaccgaac tctctctgca actcacttct gcaggcattc    1320
agtaatggga agtacagaag cgtgtggcat cgagccgtcg taaattcaaa caaagctaga    1380
ctctcggttg cttcgttcct ctgcccgtgt gatgcagcga atatcagcgt tccaaatgaa    1440
cttacaaccg gcgatgatcg agcaatatac agaggtttta catatgccga gtactacaaa    1500
aagttctgga gccggaacct ggaccaggag cactgcctgg aactattcaa gaattag      1557
```

```
<210> SEQ ID NO 6
<211> LENGTH: 336
<212> TYPE: PRT
<213> ORGANISM: Ocimum basilicum

<400> SEQUENCE: 6

Met Glu Thr Lys Val Ile Ser Gly Thr Gln Phe Thr Ser Leu Pro Ser
1               5                   10                  15

Cys Tyr Val Arg Pro Glu Ser Glu Arg Pro Lys Leu Ser Glu Val Ala
            20                  25                  30

Asp Cys Glu Asp Val Pro Val Ile Asp Leu Gly Cys Gly Asp Arg Gly
        35                  40                  45

Leu Ile Val Lys Gln Ile Gly Asp Ala Cys Arg Glu Tyr Gly Phe Phe
    50                  55                  60

Gln Val Ile Asn His Ala Val Pro Lys Asp Ile Val Asp Lys Met Val
65                  70                  75                  80

Gly Val Ala His Glu Phe Phe Ser Leu Ser Val Glu Glu Lys Met Lys
                85                  90                  95

Leu Tyr Ser Asp Asp Pro Ser Lys Thr Met Arg Leu Ser Thr Ser Phe
            100                 105                 110

Asn Val Arg Lys Glu Thr Val His Asn Trp Arg Asp Tyr Leu Arg Leu
        115                 120                 125

His Cys Tyr Pro Leu Glu Lys Tyr Ala Pro Glu Trp Pro Ser Asn Pro
    130                 135                 140

Ser Ser Phe Lys Asp Ile Val Ser Thr Tyr Cys Lys Glu Val Arg Ala
145                 150                 155                 160

Leu Gly Phe Trp Leu Gln Glu Ala Ile Ser Glu Ser Leu Gly Leu His
                165                 170                 175

Lys Asp Cys Leu Lys Asn Val Leu Gly Glu Gln Gly Gln His Met Ala
            180                 185                 190

Ile Asn Phe Tyr Pro Ala Cys Pro Glu Pro Asp Leu Thr Phe Gly Leu
        195                 200                 205

Pro Ala His Thr Asp Pro Asn Ala Leu Thr Ile Leu Leu Gln Asp Leu
    210                 215                 220

Leu Val Ser Gly Leu Gln Val Leu Lys Asp Gly Lys Trp Leu Ala Ile
225                 230                 235                 240

Lys Pro Gln Pro Asp Ala Phe Val Ile Asn Ile Gly Asp Gln Ile Gln
                245                 250                 255

Ala Phe Ser Asn Gly Lys Tyr Arg Ser Val Trp His Arg Ala Val Val
            260                 265                 270
```

```
Asn Ser Asn Lys Ala Arg Leu Ser Val Ala Ser Phe Leu Cys Pro Cys
            275                 280                 285

Asp Ala Ala Asn Ile Ser Ala Pro Asn Glu Leu Thr Thr Gly Asp Asp
290                 295                 300

Arg Ala Ile Tyr Arg Gly Phe Thr Tyr Ala Glu Tyr Tyr Lys Lys Phe
305                 310                 315                 320

Trp Ser Arg Asn Leu Asp Gln Glu His Cys Leu Glu Leu Phe Lys Asn
            325                 330                 335

<210> SEQ ID NO 7
<211> LENGTH: 340
<212> TYPE: PRT
<213> ORGANISM: Arabidopsis thaliana

<400> SEQUENCE: 7

Met Ala Ala Lys Leu Ile Ser Thr Gly Phe Arg His Thr Thr Leu Pro
1               5                   10                  15

Glu Asn Tyr Val Arg Pro Ile Ser Asp Arg Pro Arg Leu Ser Glu Val
            20                  25                  30

Ser Gln Leu Glu Asp Phe Pro Leu Ile Asp Leu Ser Ser Thr Asp Arg
        35                  40                  45

Ser Phe Leu Ile Gln Gln Ile His Gln Ala Cys Ala Arg Phe Gly Phe
50                  55                  60

Phe Gln Val Ile Asn His Gly Val Asn Lys Gln Ile Ile Asp Glu Met
65                  70                  75                  80

Val Ser Val Ala Arg Glu Phe Phe Ser Met Ser Met Glu Glu Lys Met
                85                  90                  95

Lys Leu Tyr Ser Asp Asp Pro Thr Lys Thr Thr Arg Leu Ser Thr Ser
            100                 105                 110

Phe Asn Val Lys Lys Glu Val Asn Asn Trp Arg Asp Tyr Leu Arg
        115                 120                 125

Leu His Cys Tyr Pro Ile His Lys Tyr Val Asn Glu Trp Pro Ser Asn
130                 135                 140

Pro Pro Ser Phe Lys Glu Ile Val Ser Lys Tyr Ser Arg Glu Val Arg
145                 150                 155                 160

Glu Val Gly Phe Lys Ile Glu Glu Leu Ile Ser Glu Ser Leu Gly Leu
                165                 170                 175

Glu Lys Asp Tyr Met Lys Lys Val Leu Gly Glu Gln Gly Gln His Met
            180                 185                 190

Ala Val Asn Tyr Tyr Pro Pro Cys Pro Glu Pro Glu Leu Thr Tyr Gly
        195                 200                 205

Leu Pro Ala His Thr Asp Pro Asn Ala Leu Thr Ile Leu Leu Gln Asp
210                 215                 220

Thr Thr Val Cys Gly Leu Gln Ile Leu Ile Asp Gly Gln Trp Phe Ala
225                 230                 235                 240

Val Asn Pro His Pro Asp Ala Phe Val Ile Asn Ile Gly Asp Gln Leu
                245                 250                 255

Gln Ala Leu Ser Asn Gly Val Tyr Lys Ser Val Trp His Arg Ala Val
            260                 265                 270

Thr Asn Thr Glu Asn Pro Arg Leu Ser Val Ala Ser Phe Leu Cys Pro
        275                 280                 285

Ala Asp Cys Ala Val Met Ser Pro Ala Lys Pro Leu Trp Glu Ala Glu
290                 295                 300

Asp Asp Glu Thr Lys Pro Val Tyr Lys Asp Phe Thr Tyr Ala Glu Tyr
305                 310                 315                 320
```

Tyr Lys Lys Phe Trp Ser Arg Asn Leu Asp Gln Glu His Cys Leu Glu
            325                 330                 335

Asn Phe Leu Asn
            340

<210> SEQ ID NO 8
<211> LENGTH: 723
<212> TYPE: DNA
<213> ORGANISM: Ocimum basilicum

<400> SEQUENCE: 8

| | | |
|---|---|---|
| atggtgagag cggcttgctg tgagaagatg ggagtgaaga aaggggcatg gagcccccaa | 60 |
| gaagacgaga ttctaatcaa ttacattcac aaatatgggc atggaaattg gagagctctc | 120 |
| ccaaaacaag ctgggctgtt gagatgcggg aagagttgca gactgcgatg gataaactat | 180 |
| ttgaagccag atattaaaag gggaaatttt actcaacaag gaacaaac cattatcaac | 240 |
| ttgcatcaaa tgcttggaaa caggtggtct acgatcgcag cacgattacc tggacgaaca | 300 |
| gacaatgaga taaaaaatgt ttggcacaca catttgaaga aaaacttaa agataataag | 360 |
| tattgtcaag atcccaagag actttcaatt tcagaatgtg acaacaatat tgaaaatgtg | 420 |
| gacattatta ttgctaatag tccacaagga tgttctagtg aaatatcatc agtgaccgat | 480 |
| tcatcgctcg agaaaatagt tgtgaagaag gaagaagtgg attattcatc ggagtatttt | 540 |
| ccgacgatcg acgagagtta ctggtcggaa gatttgttca aggggatgc taaggaaata | 600 |
| agtgaagatg ttgatgccaa gatagaatgt gtgaaggatt caaaagttga ggatggcagc | 660 |
| atggactttt ggtacaacct ttttactaga gctggtgaca tgcctgattt gccagaattt | 720 |
| tag | 723 |

<210> SEQ ID NO 9
<211> LENGTH: 1737
<212> TYPE: DNA
<213> ORGANISM: Ocimum basilicum

<400> SEQUENCE: 9

| | | |
|---|---|---|
| atggtgagag cggcttgctg tgagaagatg ggagtgaaga aaggggcatg gagcccccaa | 60 |
| gaagacgaga ttctaatcaa ttacattcac aaatatgggc atggaaattg gagagctctc | 120 |
| ccaaaacaag ctggtaccca cttaattaat ttcttctgaa ttttatttat gtctttcaga | 180 |
| aaatgcaatc ataatcataa tttgcagggc tgttgagatg cgggaagagt gcagactgc | 240 |
| gatggataaa ctatttgaag ccagatatta aaagggaaa ttttactcaa caagaggaac | 300 |
| aaaccattat caacttgcat caaatgcttg gaaacaggtc agtctgtcaa tttttttttt | 360 |
| gggtacaatg ttctagtttg atttccttat aaaattatta agtttattgt tcttcagttc | 420 |
| cattttatta tacgcagttt aatttttataa ttattaacta gggtttaatt atatcaatga | 480 |
| ctgttaatat ttaatccgta aaaacacgat ttcaatttca atttaagtgt taatgtatat | 540 |
| tgaaataatg aatttatgtt ttgtgagttg tagtgttatg tttctttta ggaaaagttt | 600 |
| tctgtgttag ggaattttac gtcttactgg ttaaaatgtg cgatacacat attttaatat | 660 |
| gaaaatgtag aatagcggtt gtttaaaata cgttgagtat gtgattggtt ggtcgctatt | 720 |
| tgatttgatt gattactaga gaatcataga tgcaagctgc gtattaacga acaaaagtct | 780 |
| tgcaattaat cgcttttaac aaatactgaa ttattcgtaa cacgacaaaa taacaattgt | 840 |
| ctttaagaag aagaaaaaaa ggagtcgatc ccttctcttt aaacgtgcgt cttggaaaca | 900 |

```
aaaatcaaga attgctgcta taattaatca cataatgaat attgctctta ttttaaatgc    960
cttttagatc tacacagtcc ttaatatata tatatatata tatatatata tatatatata   1020
tatattgtca cagacaacta tgcaagcaag catcgttctg catatatctc cttaggattt   1080
tgtgtctcaa cagctaatta attaaatcaa ggcacaagat ttaatgtttc ttcattataa   1140
tttacctata cctcgttatg ctgctaatcg ccattatttt actgctaaaa atctaaatct   1200
aattgcccca actcacgcaa atatcttatg tattacattt tttttttatt tacagattat   1260
ttttttttgga tttataggtg gtctacgatc gcagcacgat tacctggacg aacagacaat   1320
gagataaaaa atgtttggca cacacatttg aagaaaaaac ttaaagataa taagtattgt   1380
caagatccca agagactttc aatttcagaa tgtgacaaca atattgaaaa tgtggacatt   1440
attattgcta atagtccaca aggatgttct agtgaaatat catcagtgac cgattcatcg   1500
ctcgagaaaa tagttgtgaa gaaggaagaa gtggattatt catcggagta ttttccgacg   1560
atcgacgaga gttactggtc ggaagatttg ttcaaggggg atgctaagga aataagtgaa   1620
gatgttgatg ccaagataga atgtgtgaag gattcaaaag ttgaggatgg cagcatggac   1680
ttttggtaca accttttttac tagagctggt gacatgcctg atttgccaga attttag     1737
```

```
<210> SEQ ID NO 10
<211> LENGTH: 240
<212> TYPE: PRT
<213> ORGANISM: Ocimum basilicum

<400> SEQUENCE: 10

Met Val Arg Ala Ala Cys Cys Glu Lys Met Gly Val Lys Lys Gly Ala
1               5                   10                  15

Trp Ser Pro Gln Glu Asp Glu Ile Leu Ile Asn Tyr Ile His Lys Tyr
                20                  25                  30

Gly His Gly Asn Trp Arg Ala Leu Pro Lys Gln Ala Gly Leu Leu Arg
            35                  40                  45

Cys Gly Lys Ser Cys Arg Leu Arg Trp Ile Asn Tyr Leu Lys Pro Asp
        50                  55                  60

Ile Lys Arg Gly Asn Phe Thr Gln Gln Glu Glu Gln Thr Ile Ile Asn
65                  70                  75                  80

Leu His Gln Met Leu Gly Asn Arg Trp Ser Thr Ile Ala Ala Arg Leu
                85                  90                  95

Pro Gly Arg Thr Asp Asn Glu Ile Lys Asn Val Trp His Thr His Leu
            100                 105                 110

Lys Lys Lys Leu Lys Asp Asn Lys Tyr Cys Gln Asp Pro Lys Arg Leu
        115                 120                 125

Ser Ile Ser Glu Cys Asp Asn Asn Ile Glu Asn Val Asp Ile Ile Ile
    130                 135                 140

Ala Asn Ser Pro Gln Gly Cys Ser Ser Glu Ile Ser Ser Val Thr Asp
145                 150                 155                 160

Ser Ser Leu Glu Lys Ile Val Val Lys Lys Glu Val Asp Tyr Ser
                165                 170                 175

Ser Glu Tyr Phe Pro Thr Ile Asp Glu Ser Tyr Trp Ser Glu Asp Leu
            180                 185                 190

Phe Lys Gly Asp Ala Lys Glu Ile Ser Glu Asp Val Asp Ala Lys Ile
        195                 200                 205

Glu Cys Val Lys Asp Ser Lys Val Glu Asp Gly Ser Met Asp Phe Trp
    210                 215                 220

Tyr Asn Leu Phe Thr Arg Ala Gly Asp Met Pro Asp Leu Pro Glu Phe
```

<210> SEQ ID NO 11
<211> LENGTH: 249
<212> TYPE: PRT
<213> ORGANISM: Arabidopsis thaliana

<400> SEQUENCE: 11

Met Gly Arg Ala Pro Cys Cys Glu Lys Met Gly Val Lys Arg Gly Pro
1               5                   10                  15

Trp Thr Pro Glu Glu Asp Gln Ile Leu Ile Asn Tyr Ile His Leu Tyr
            20                  25                  30

Gly His Ser Asn Trp Arg Ala Leu Pro Lys His Ala Gly Leu Leu Arg
        35                  40                  45

Cys Gly Lys Ser Cys Arg Leu Arg Trp Ile Asn Tyr Leu Arg Pro Asp
    50                  55                  60

Ile Lys Arg Gly Asn Phe Thr Pro Gln Glu Glu Gln Thr Ile Ile Asn
65                  70                  75                  80

Leu His Glu Ser Leu Gly Asn Arg Trp Ser Ala Ile Ala Ala Lys Leu
                85                  90                  95

Pro Gly Arg Thr Asp Asn Glu Ile Lys Asn Val Trp His Thr His Leu
            100                 105                 110

Lys Lys Arg Leu Ser Lys Asn Leu Asn Asn Gly Gly Asp Thr Lys Asp
        115                 120                 125

Val Asn Gly Ile Asn Glu Thr Thr Asn Glu Asp Lys Gly Ser Val Ile
    130                 135                 140

Val Asp Thr Ala Ser Leu Gln Gln Phe Ser Asn Ser Ile Thr Thr Phe
145                 150                 155                 160

Asp Ile Ser Asn Asp Asn Lys Asp Ile Met Ser Tyr Glu Asp Ile
                165                 170                 175

Ser Ala Leu Ile Asp Asp Ser Phe Trp Ser Asp Val Ile Ser Val Asp
            180                 185                 190

Asn Ser Asn Lys Asn Glu Lys Lys Ile Glu Asp Trp Glu Gly Leu Ile
        195                 200                 205

Asp Arg Asn Ser Lys Lys Cys Ser Tyr Ser Asn Ser Lys Leu Tyr Asn
    210                 215                 220

Asp Asp Met Glu Phe Trp Phe Asp Val Phe Thr Ser Asn Arg Arg Ile
225                 230                 235                 240

Glu Glu Phe Ser Asp Ile Pro Glu Phe
                245

<210> SEQ ID NO 12
<211> LENGTH: 26
<212> TYPE: DNA
<213> ORGANISM: Ocimum basilicum

<400> SEQUENCE: 12
gccaccgtcg ccaacttggg cccagg                                    26

<210> SEQ ID NO 13
<211> LENGTH: 22
<212> TYPE: DNA
<213> ORGANISM: Ocimum basilicum

<400> SEQUENCE: 13
gcaaagaagt tcgggccctg gg                                        22

```
<210> SEQ ID NO 14
<211> LENGTH: 26
<212> TYPE: DNA
<213> ORGANISM: Ocimum basilicum

<400> SEQUENCE: 14
gaccagtaac tctcgtcgat cgtcgg                                              26

<210> SEQ ID NO 15
<211> LENGTH: 9106
<212> TYPE: DNA
<213> ORGANISM: Artificial Sequence
<220> FEATURE:
<223> OTHER INFORMATION: vector pRD321

<400> SEQUENCE: 15
tatagtgagt cgtattacaa ttcactggcc gtcgttttac aacgtcgtga ctgggaaaac         60
cctggcgtta cccaacttaa tcgccttgca gcacatcccc ctttcgccag ctggcgtaat        120
agcgaagagg cccgcaccga tcgcccttcc caacagttgc gcagcctgaa tggcgaatgg        180
acgcgccctg tagcggcgca ttaagcgcgg cgggtgtggt ggttacgcgc agcgtgaccg        240
ctacacttgc cagcgcccta gcgcccgctc ctttcgcttt cttcccttcc tttctcgcca        300
cgttcgccgg ctttccccgt caagctctaa atcgggggct ccctttaggg ttccgattta        360
gtgctttacg gcacctcgac cccaaaaaac ttgattaggg tgatggttca cgtagtgggc        420
catcgccctg atagacggtt tttcgccctt gacgttgga gtccacgttc tttaatagtg         480
gactcttgtt ccaaactgga acaacactca accctatctc ggtctattct tttgatttat        540
aagggatttt gccgatttcg gcctattggt taaaaaatga gctgatttaa caaaaattta        600
acgcgaattt taacaaaata ttaacgctta caatttcctg atgcggtatt ttctccttac        660
gcatctgtgc ggtatttcac accgcatatg gtgcactctc agtacaatct gctctgatgc        720
cgcatagtta agccagcccc gacacccgcc aacacccgct gacgcgccct gacgggcttg        780
tctgctcccg gcatccgctt acagacaagc tgtgaccgtc tccgggagct gcatgtgtca        840
gaggttttca ccgtcatcac cgaaacgcgc gagacgaaag gcctcgtga tacgcctatt         900
tttataggtt aatgtcatga taataatggt ttcttagacg tcaggtggca cttttcgggg        960
aaatgtgcgc ggaaccccta tttgtttatt tttctaaata cattcaaata tgtatccgct       1020
catgagacaa taaccctgat aaatgcttca ataatattga aaaggaaga gtatgagtat        1080
tcaacatttc cgtgtcgccc ttattccctt ttttgcggca ttttgccttc ctgttttgc         1140
tcacccagaa acgctggtga agtaaaaga tgctgaagat cagttgggtg cacgagtggg        1200
ttacatcgaa ctggatctca acagcggtaa gatccttgag agttttcgcc ccgaagaacg       1260
ttttccaatg atgagcactt ttaaagttct gctatgtggc gcggtattat cccgtattga       1320
cgccgggcaa gagcaactcg gtcgccgcat acactattct cagaatgact tggttgagta       1380
ctcaccagtc acagaaaagc atcttacgga tggcatgaca gtaagagaat tatgcagtgc       1440
tgccataacc atgagtgata acactgcggc caacttactt ctgacaacga tcggaggacc       1500
gaaggagcta accgcttttt tgcacaacat ggggatcat gtaactcgcc ttgatcgttg        1560
ggaaccggag ctgaatgaag ccataccaaa cgacgagcgt gacaccacga tgcctgtagc       1620
aatggcaaca acgttgcgca aactattaac tggcgaacta cttactctag cttcccggca       1680
acaattaata gactgatgg aggcggataa agttgcagga ccacttctgc gctcggccct        1740
tccggctggc tggtttattg ctgataaatc tggagccggt gagcgtgggt ctcgcggtat       1800
```

```
cattgcagca ctggggccag atggtaagcc ctcccgtatc gtagttatct acacgacggg    1860
gagtcaggca actatggatg aacgaaatag acagatcgct gagataggtg cctcactgat    1920
taagcattgg taactgtcag accaagttta ctcatatata ctttagattg atttaaaact    1980
tcatttttaa tttaaaagga tctaggtgaa gatccttttt gataatctca tgaccaaaat    2040
cccttaacgt gagttttcgt tccactgagc gtcagacccc gtagaaaaga tcaaaggatc    2100
ttcttgagat cctttttttc tgcgcgtaat ctgctgcttg caaacaaaaa aaccaccgct    2160
accagcggtg gtttgtttgc cggatcaaga gctaccaact cttttccga aggtaactgg     2220 cttcagcaga gcgcagatac caaatactgt tcttctagtg tagccgtagt taggccacca    2280
cttcaagaac tctgtagcac cgcctacata cctcgctctg ctaatcctgt taccagtggc    2340
tgctgccagt ggcgataagt cgtgtcttac cgggttggac tcaagacgat agttaccgga    2400
taaggcgcag cggtcgggct gaacggggggg ttcgtgcaca cagcccagct tggagcgaac   2460
gacctacacc gaactgagat acctacagcg tgagctatga gaaagcgcca cgcttcccga    2520
agggagaaag gcggacaggt atccggtaag cggcagggtc ggaacaggag agcgcacgag    2580
ggagcttcca gggggaaacg cctggtatct ttatagtcct gtcgggtttc gccacctctg    2640
acttgagcgt cgatttttgt gatgctcgtc aggggggcgg agcctatgga aaaacgccag    2700
caacgcggcc ttttacggt tcctggcctt ttgctggcct tttgctcaca tgttctttcc     2760
tgcgttatcc cctgattctg tggataaccg tattaccgcc tttgagtgag ctgataccgc    2820
tcgccgcagc cgaacgaccg agcgcagcga gtcagtgagc gaggaagcgg aagagcgccc    2880
aatacgcaaa ccgcctctcc ccgcgcgttg gccgattcat taatgcagct ggcacgacag    2940
gtttcccgac tggaaagcgg gcagtgagcg caacgcaatt aatgtgagtt agctcactca    3000
ttaggcaccc caggctttac actttatgct tccggctcgt atgttgtgtg gaattgtgag    3060
cggataacaa tttcacacag gaaacagcta tgaccatgat tacgccaagc tatttaggtg    3120
acactataga atactcaagc ttgcatgcct gcaggtcgac tctagaggat ccccgggtac    3180
cgagctcgaa ttcgcccaag cttcattcgg agttttgta tcttgtttca tagtttgtcc     3240
caggattaga atgattaggc atcgaacctt caagaatttg attgaataaa acatcttcat    3300
tcttaagata tgaagataat cttcaaaagg cccctgggaa tctgaaagaa gagaagcagg    3360
cccatttata tgggaaagaa caatagtatt tcttatatag gcccatttaa gttgaaaaca    3420
atcttcaaaa gtcccacatc gcttagataa gaaaacgaag ctgagtttat atacagctag    3480
agtcgaagta gtgccaccgt cgccaacttg ggcccgtttt agagctagaa atagcaagtt    3540
aaaataaggc tagtccgtta tcaacttgaa aaagtggcac cgagtcggtg ctttttttg     3600 cgcacgaggt acgcctgagc gtctagattt gcatgcctgc aggtcaacat ggtggagcac    3660
gacacacttg tctactccaa aaatatcaaa gatacagtct cagaagacca agggcaatt     3720 gagacttttc aacaaggggt aatatccgga aacctcctcg gattccattg cccagctatc    3780
tgtcacttta ttgtgaagat agtggaaaag gaaggtggct cctacaaatg ccatcattgc    3840
gataaaggaa aggccatcgt tgaagatgcc tctgccgaca gtggtcccaa agatggaccc    3900
ccacccacga ggagcatcgt ggaaaaagaa gacgttccaa ccacgtcttc aaagcaagtg    3960
gattgatgtg ataacatggt ggagcacgac acacttgtct actccaaaaa tatcaaagat    4020
acagtctcag aagaccaaag ggcaattgag acttttcaac aaagggtgat atccggaaac    4080
ctcctcggat tccattgccc agctatctgt cactttattg tgaagatagt ggaaaggaa     4140 ggtggctcct acaaatgcca tcattgcgat aaaggaaagg ccatcgttga agatgcctct    4200
```

```
gccgacagtg gtcccaaaga tggacccca cccacgagga gcatcgtgga aaaagaagac    4260
gttccaacca cgtcttcaaa gcaagtggat tgatgtgata tctccactga cgtaagggat    4320
gacgcacaat cccactatcc ttcgcaagac ccttcctcta tataaggaag ttcatttcat    4380
ttggagagga cctcgacctc aacacaacat atacaaaaca aacgaatctc aagcaatcaa    4440
gcattctact tctattgcag caatttaaat catttctttt aaagcaaaag caattttctg    4500
aaaattttca ccatttacga acgatactcg agatggacta caaggaccac gacgagatt     4560 acaaagacca cgacattgat tacaaggatg atgacgacaa gatggctccc aagaagaagc    4620
gaaaggtggg catccacggc gtgcccgctg ccgacaaaaa gtatagtatc ggactggata    4680
ttggcactaa cagcgtggga tgggccgtca tcaccgacga gtacaaagtg ccaagcaaga    4740
agttcaaggt cctgggaaac accgatagac acagtatcaa gaaaaatctg attggagccc    4800
tgctgttcga ctcaggggag acagctgaag caactaggct gaaaagaaca gctaggagac    4860
ggtatactcg ccgaaagaat cggatctgct acctccagga gattttctcc aacgaaatgg    4920
ccaaggtgga cgatagtttc tttcatcgcc tggaggaatc attcctggtc gaggaagata    4980
agaaacacga gaggcatccc atctttggca acattgtgga cgaggtcgct tatcacgaaa    5040
agtaccctac aatctatcat ctgcggaaga aactggtgga cagcactgat aaggcagacc    5100
tgcgcctgat ctatctggcc ctggctcaca tgattaagtt cagggggcat tttctgatcg    5160
agggcgatct gaacccagac aattccgatg tggacaagct gttcatccag ctggtccaga    5220
catacaatca gctgtttgag gaaaaccca ttaatgcatc tggggtggac gcaaaagcca     5280
tcctgagtgc cagactgtct aagagtagga gactggagaa cctgatcgct cagctgccag    5340
gcgaaaagaa aaacggcctg tttgaaaatc tgattgcact gtcactggga ctgaccccca    5400
acttcaagag caatttttgat ctggccgagg acgctaagct ccagctgagc aaggacacct   5460
acgacgatga cctggataac ctgctggctc agatcggcga tcagtacgca gacctgttcc    5520
tggccgctaa gaatctgtct gacgccatcc tgctgagtga tattctgaga gtgaacaccg    5580
agattacaaa agcccccctg tcagctagca tgatcaagag atatgacgag caccatcagg    5640
atctgaccct gctgaaggct ctggtgcggc agcagctgcc tgagaagtac aaagaaatct    5700
tctttgatca gagcaagaat gggtacgccg gctatattga cggcggagct tcccaggagg    5760
agttctacaa gtttatcaaa cctattctgg agaaagatga cggcactgag gaactgctgg    5820
tgaaactgaa tcgggaagac ctgctgcgga agcagcgcac cttcgataac ggcagcatcc    5880
ctcaccagat tcatctggga gagctgcacg caatcctgcg gcgccaggaa gacttctacc    5940
catttctgaa ggataaccgg gagaagatcg aaaaaattct gactttccgc atccccctact   6000 atgtggggcc tctggcaaga ggcaattccc ggtttgcctg atgacccgc aagtctgagg     6060 aaacaatcac tccctggaac ttcgaggaag tggtcgataa gggcgcttcc gcacagtctt    6120
tcattgagag gatgacaaat tttgacaaga acctgccaaa tgaaaaagtg ctgcccaagc    6180
acagcctgct gtacgagtat ttcaccgtct ataacgaact gacaaaggtg aaatacgtca    6240
ctgagggcat gagaaagcct gccttcctgt ccggagaaca gaagaaagct atcgtggacc    6300
tgctgtttaa aaccaatcgg aaggtgacag tcaagcagct gaaagaggac tacttcaaga    6360
aaattgaatg tttcgattct gtggagatca gtgggggtcga agacaggttt aacgcctctc    6420
tgggcaccta ccacgatctg ctgaagatca ttaaggataa agacttcctg gacaacgagg    6480
aaaatgagga catcctggag gacattgtgc tgaccctgac actgtttgag gatcgggaaa    6540
```

```
tgatcgagga acgcctgaag acctacgccc atctgttcga tgacaaagtg atgaaacagc    6600
tgaagcgaag gagatacact gggtggggcc gactgagcag gaagctgatc aatggcattc    6660
gcgacaaaca gagtggaaag acaatcctgg actttctgaa gtcagatggc ttcgctaaca    6720
ggaacttcat gcagctgatt cacgatgact ctctgacttt caaagaggac atccagaagg    6780
cacaggtgtc cggacagggg gactctctgc acgagcatat cgcaaacctg gccgggagcc    6840
ctgccatcaa gaaaggcatc ctccagaccg tgaaggtggt ggacgagctg gtgaaagtca    6900
tgggaagaca taagccagaa aacatcgtga ttgagatggc cagggagaat cagaccacac    6960
agaaagggca gaagaactct cgggagcgca tgaaacgcat cgaggaagga attaaggaac    7020
tggggagtca gatcctgaaa gagcaccccg tggaaaacac acagctccag aatgagaagc    7080
tgtatctgta ctacctccag aatggccgcg atatgtacgt ggaccaggag ctggatatta    7140
accgactgtc agattatgac gtggatcata tcgtcccaca gtcattcctg aaagatgaca    7200
gcattgacaa taaggtgctg acccgcagcg acaaaaaccg aggaaagagt gataatgtcc    7260
cctcagagga agtggtcaag aaaatgaaga actactggag gcagctgctg aatgccaaac    7320
tgatcaccca gcgaaagttt gataacctga caaaagctga gagggggggc ctgtccgaac    7380
tggacaaagc aggcttcatc aagcgacagc tggtggagac aaggcagatc acaaagcacg    7440
tcgctcagat cctggacagc aggatgaaca ccaagtacga tgagaatgac aaactgatcc    7500
gggaagtgaa ggtcattaca ctgaagtcaa aactggtgag cgactttagg aaagatttcc    7560
agttctacaa ggtcagagag atcaacaact accaccatgc tcatgacgca tacctgaacg    7620
cagtggtcgg gactgccctg attaagaaat accctaaact ggagtctgag ttcgtgtacg    7680
gcgactataa ggtgtacgat gtcagaaaaa tgatcgccaa gagcgagcag gaaattggca    7740
aagccaccgc taagtatttc ttttactcca acatcatgaa tttctttaag actgagatca    7800
ccctggcaaa tggcgaaatc cgaaagaggc cactgattga gactaacgga gagacagggg    7860 aaaatcgtgtg ggacaaagga agagattttg ctaccgtgcg gaaggtcctg agtatgcccc    7920
aagtgaatat tgtcaagaaa acagaggtgc agactggagg gttcagtaag gaatcaattc    7980
tgcctaaacg caacagcgat aagctgatcg cccgaaagaa agactgggac cccaagaagt    8040
atggcggatt cgactcccca accgtggctt actctgtcct ggtggtcgca aaggtggaga    8100
agggaaaaag caagaaactg aaatccgtca aggaactgct ggggatcaca attatgagga    8160
ggagcagctt cgaaaagaat cctatcgatt ttctggaggc caaagggtat aaggaagtga    8220
agaaagacct gatcatcaag ctgccaaagt actctctgtt tgagctggaa aacggcagaa    8280
agcggatgct ggcaagtgcc ggcgagctgc aaaaaggaaa tgaactggcc ctgccctcaa    8340
agtacgtgaa cttcctgtat ctggctagcc actacgagaa gctgaaaggc tcccctgagg    8400
ataacgaaca gaaacagctg tttgtggagc agcacaagca ttatctggac gagatcattg    8460
aacagattag cgagttctcc aaaacgcgtga tcctggctga cgcaaatctg gataaggtcc    8520
tgtctgcata caacaaacac agggacagcc aatcagaga gcaggccgaa aatatcattc    8580
atctgttcac tctgaccaac ctgggagccc ccgcagcctt caagtatttt gacactacca    8640
tcgatcgcaa acgatacaca agcactaagg aggtgctgga tgctaccctg atccaccaga    8700
gcattactgg gctgtacgag acaaggatcg acctgtccca gctgggggga gacaaacgcc    8760
cagccgccac caagaaagca ggacaggcaa agaagaagaa gtgagagctc tgattgatcg    8820
atagagctca aatttccccg atcgttcaaa catttggcaa taaagtttct taagattgaa    8880
tcctgttgcc ggtcttgcga tgattatcat ataatttctg ttgaattacg ttaagcatgt    8940
```

```
aataattaac atgtaatgca tgacgttatt tatgagatgg ttttttatga ttagagtccc    9000
gcaattatac atttaatacg cgatagaaaa caaaatatag cgcgcaaact aggataaatt    9060
atcgcgcgcg gtgtcatcta tgttactaga tcggggatcc gaattc                   9106
```

<210> SEQ ID NO 16
<211> LENGTH: 14591
<212> TYPE: DNA
<213> ORGANISM: Artificial Sequence
<220> FEATURE:
<223> OTHER INFORMATION: vector pRD327

<400> SEQUENCE: 16

```
gtaatcatgg tcatagctgt ttcctgtgtg aaattgttat ccgctcacaa ttccacacaa      60
catacgagcc ggaagcataa agtgtaaagc ctggggtgcc taatgagtga gctaactcac     120
attaattgcg ttgcgctcac tgcccgcttt ccagtcggga aacctgtcgt gccagctgca     180
ttaatgaatc ggccaacgcg cggggagagg cggtttgcgt attggctaga gcagcttgcc     240
aacatggtgg agcacgacac tctcgtctac tccaagaata tcaaagatac agtctcagaa     300
gaccaaaggg ctattgagac ttttcaacaa agggtaatat cgggaaacct cctcggattc     360
cattgcccag ctatctgtca cttcatcaaa aggacagtag aaaaggaagg tggcacctac     420
aaatgccatc attgcgataa aggaaaggct atcgttcaag atgcctctgc cgacagtggt     480
cccaaagatg gacccccacc cacgaggagc atcgtggaaa aagaagacgt tccaaccacg     540
tcttcaaagc aagtggattg atgtgataac atggtggagc acgacactct cgtctactcc     600
aagaatatca agatacagt ctcagaagac caaagggcta ttgactttt caacaaagg       660 gtaatatcgg gaaacctcct cggattccat tgcccagcta tctgtcactt catcaaaagg    720
acagtagaaa aggaaggtgg cacctacaaa tgccatcatt gcgataaagg aaaggctatc    780
gttcaagatg cctctgccga cagtggtccc aaagatggac ccccacccac gaggagcatc    840
gtggaaaaag aagacgttcc aaccacgtct tcaaagcaag tggattgatg tgatatctcc    900
actgacgtaa gggatgacgc acaatcccac tatccttcgc aagaccttcc tctatataag    960
gaagttcatt tcatttggag aggacacgct gaaatcacca gtctctctct acaaatctat   1020
ctctctcgag cttttcgaga tctgtcgatc gaccatgggg attgaacaag atggattgca   1080
cgcaggttct ccggccgctt gggtggagag gctattcggc tatgactggg cacaacagac   1140
aatcggctgc tctgatgccg ccgtgttccg gctgtcagcg caggggcgcc cggttctttt   1200
tgtcaagacc gacctgtccg gtgccctgaa tgaactccag gacgaggcag cgcggctatc   1260
gtggctggcc acgacgggcg ttccttgcgc agctgtgctc gacgttgtca ctgaagcggg   1320
aagggactgg ctgctattgg gcgaagtgcc ggggcaggat ctcctgtcat ctcaccttgc   1380
tcctgccgag aaagtatcca tcatggctga tgcaatgcgg cggctgcata cgcttgatcc   1440
ggctacctgc ccattcgacc accaagcgaa acatcgcatc gagcgagcac gtactcggat   1500
ggaagccggt cttgtcgatc aggatgatct ggacgaagag catcaggggc tcgcgccagc   1560
cgaactgttc gccaggctca aggcgcgcat gcccgacggc gaggatctcg tcgtgacaca   1620
tggcgatgcc tgcttgccga atatcatggt ggaaaatggc cgcttttctg gattcatcga   1680
ctgtggccgg ctgggtgtgg cggaccgcta tcaggacata gcgttggcta cccgtgatat   1740
tgctgaagag cttggcggcg aatgggctga ccgcttcctc gtgctttacg gtatcgccgc   1800
tcccgattcg cagcgcatcg ccttctatcg ccttcttgac gagttcttct gagcgggact   1860
```

-continued

| | | | | |
|---|---|---|---|---|
| ctggggttcg | gatcgatcct | ctagctagag | tcgatcgaca | agctcgagtt tctccataat | 1920 |
| aatgtgtgag | tagttcccag | ataagggaat | tagggttcct | ataggtttc gctcatgtgt | 1980 |
| tgagcatata | agaaacccctt | agtatgtatt | tgtatttgta | aaatacttct atcaataaaa | 2040 |
| tttctaattc | ctaaaaccaa | aatccagtac | taaaatccag | atcccccgaa ttaattcggc | 2100 |
| gttaattcag | tacattaaaa | acgtccgcaa | tgtgttatta | agttgtctaa gcgtcaattt | 2160 |
| gtttacacca | caatatatcc | tgccaccagc | cagccaacag | ctccccgacc ggcagctcgg | 2220 |
| cacaaaatca | ccactcgata | caggcagccc | atcagtccgg | gacggcgtca gcgggagagc | 2280 |
| cgttgtaagg | cggcagactt | tgctcatgtt | accgatgcta | ttcggaagaa cggcaactaa | 2340 |
| gctgccgggt | ttgaaacacg | gatgatctcg | cggagggtag | catgttgatt gtaacgatga | 2400 |
| cagagcgttg | ctgcctgtga | tcaccgcggt | ttcaaaatcg | gctccgtcga tactatgtta | 2460 |
| tacgccaact | ttgaaaacaa | cttttgaaaaa | gctgttttct | ggtatttaag gttttagaat | 2520 |
| gcaaggaaca | gtgaattgga | gttcgtcttg | ttataattag | cttcttgggg tatctttaaa | 2580 |
| tactgtagaa | aagaggaagg | aaataataaa | tggctaaaat | gagaatatca ccggaattga | 2640 |
| aaaaactgat | cgaaaaatac | cgctgcgtaa | aagatacgga | aggaatgtct cctgctaagg | 2700 |
| tatataagct | ggtgggagaa | aatgaaaacc | tatatttaaa | aatgacggac agccggtata | 2760 |
| aagggaccac | ctatgatgtg | aacgggaaa | aggacatgat | gctatggctg aaggaaagc | 2820 |
| tgcctgttcc | aaaggtcctg | cactttgaac | ggcatgatgg | ctggagcaat ctgctcatga | 2880 |
| gtgaggccga | tggcgtcctt | tgctcggaag | agtatgaaga | tgaacaaagc cctgaaaaga | 2940 |
| ttatcgagct | gtatgcggag | tgcatcaggc | tctttcactc | catcgacata tcggattgtc | 3000 |
| cctatacgaa | tagcttagac | agccgcttag | ccgaattgga | ttacttactg aataacgatc | 3060 |
| tggccgatgt | ggattgcgaa | aactgggaag | aagacactcc | atttaaagat ccgcgcgagc | 3120 |
| tgtatgattt | tttaaagacg | gaaaagcccg | aagaggaact | tgtcttttcc cacggcgacc | 3180 |
| tgggagacag | caacatcttt | gtgaaagatg | gcaaagtaag | tggctttatt gatcttggga | 3240 |
| gaagcggcag | ggcggacaag | tggtatgaca | ttgccttctg | cgtccggtcg atcagggagg | 3300 |
| atatcgggga | agaacagtat | gtcgagctat | tttttgactt | actggggatc aagcctgatt | 3360 |
| gggagaaaat | aaaatattat | attttactgg | atgaattgtt | ttagtaccta gaatgcatga | 3420 |
| ccaaaatccc | ttaacgtgag | ttttcgttcc | actgagcgtc | agaccccgta gaaaagatca | 3480 |
| aaggatcttc | ttgagatcct | ttttttctgc | gcgtaatctg | ctgcttgcaa acaaaaaaac | 3540 |
| caccgctacc | agcggtggtt | tgtttgccgg | atcaagagct | accaactctt tttccgaagg | 3600 |
| taactggctt | cagcagagcg | cagataccaa | atactgtcct | tctagtgtag ccgtagttag | 3660 |
| gccaccactt | caagaactct | gtagcaccgc | ctacatacct | cgctctgcta atcctgttac | 3720 |
| cagtggctgc | tgccagtggc | gataagtcgt | gtcttaccgg | gttggactca agacgatagt | 3780 |
| taccggataa | ggcgcagcgg | tcgggctgaa | cggggggttc | gtgcacacag cccagcttgg | 3840 |
| agcgaacgac | ctacaccgaa | ctgagatacc | tacagcgtga | gctatgagaa agcgccacgc | 3900 |
| ttcccgaagg | gagaaaggcg | gacaggtatc | cggtaagcgg | cagggtcgga acaggagagc | 3960 |
| gcacgaggga | gcttccaggg | ggaaacgcct | ggtatcttta | tagtcctgtc gggtttcgcc | 4020 |
| acctctgact | tgagcgtcga | tttttgtgat | gctcgtcagg | gggcggagc ctatggaaaa | 4080 |
| acgccagcaa | cgcggccttt | ttacggttcc | tggccttttg | ctggccttttt gctcacatgt | 4140 |
| tctttcctgc | gttatcccct | gattctgtgg | ataaccgtat | taccgccttt gagtgagctg | 4200 |
| ataccgctcg | ccgcagccga | acgaccgagc | gcagcgagtc | agtgagcgag gaagcggaag | 4260 |

```
agcgcctgat gcggtatttt ctccttacgc atctgtgcgg tatttcacac cgcatatggt   4320
gcactctcag tacaatctgc tctgatgccg catagttaag ccagtataca ctccgctatc   4380
gctacgtgac tgggtcatgg ctgcgccccg acacccgcca acacccgctg acgcgccctg   4440
acgggcttgt ctgctcccgg catccgctta cagacaagct gtgaccgtct ccgggagctg   4500
catgtgtcag aggttttcac cgtcatcacc gaaacgcgcg aggcagggtg ccttgatgtg   4560
ggcgccggcg gtcgagtggc gacgcgcgg cttgtccgcg ccctggtaga ttgcctggcc   4620
gtaggccagc cattttttgag cggccagcgg ccgcgatagg ccgacgcgaa cggcggggc   4680 gtagggagcg cagcgaccga agggtaggcg cttttttgcag ctcttcggct gtgcgctggc   4740
cagacagtta tgcacaggcc aggcgggttt taagagtttt aataagtttt aaagagtttt   4800
aggcggaaaa atcgcctttt ttctcttta tatcagtcac ttacatgtgt gaccggttcc   4860
caatgtacgg ctttgggttc ccaatgtacg ggttccggtt cccaatgtac ggctttgggt   4920
tcccaatgta cgtgctatcc acaggaaaga gaccttttcg accttttttcc cctgctaggg   4980 caatttgccc tagcatctgc tccgtacatt aggaaccggc ggatgcttcg ccctcgatca   5040
ggttgcggta gcgcatgact aggatcgggc cagcctgccc cgcctcctcc ttcaaatcgt   5100
actccggcag gtcatttgac ccgatcagct tgcgcacggt gaaacagaac ttcttgaact   5160
ctccggcgct gccactgcgt tcgtagatcg tcttgaacaa ccatctggct tctgccttgc   5220
ctgcggcgcg gcgtgccagg cggtagagaa acggccgat gccgggatcg atcaaaaagt   5280
aatcggggtg aaccgtcagc acgtccgggt tcttgccttc tgtgatctcg cggtacatcc   5340
aatcagctag ctcgatctcg atgtactccg gccgcccggt ttcgctcttt acgatcttgt   5400
agcggctaat caaggcttca ccctcggata ccgtcaccag gcggccgttc ttggccttct   5460
tcgtacgctg catggcaacg tgcgtggtgt ttaaccgaat gcaggtttct accaggtcgt   5520
ctttctgctt tccgccatcg gctcgccggc agaacttgag tacgtccgca acgtgtggac   5580
ggaacacgcg gccgggcttg tctcccttcc cttcccggta tcggttcatg gattcggtta   5640
gatgggaaac cgccatcagt accaggtcgt aatcccacac actggccatg ccggccggcc   5700
ctgcggaaac ctctacgtgc ccgtctggaa gctcgtagcg gatcacctcg ccagctcgtc   5760
ggtcacgctt cgacagacgg aaaacggcca cgtccatgat gctgcgacta tcgcgggtgc   5820
ccacgtcata gagcatcgga acgaaaaaat ctggttgctc gtcgcccttg ggcggcttcc   5880
taatcgacgg cgcaccggct gccggcggtt gccgggattc tttgcggatt cgatcagcgg   5940
ccgcttgcca cgattcaccg gggcgtgctt ctgcctcgat gcgttgccgc tgggcggcct   6000
gcgcggcctt caacttctcc accaggtcat cacccagcgc cgcgccgatt tgtaccgggc   6060
cggatggttt gcgaccgctc acgccgattc ctcgggcttg ggggttccag tgccattgca   6120
gggccggcag acaacccagc cgcttacgcc tggccaaccg cccgttcctc cacacatggg   6180
gcattccacg gcgtcggtgc ctggttgttc ttgattttcc atgccgcctc ctttagccgc   6240
taaaattcat ctactcattt attcatttgc tcatttactc tggtagctgc gcgatgtatt   6300
cagatagcag ctcggtaatg gtcttgcctt ggcgtaccgc gtacatcttc agcttggtgt   6360
gatcctccgc cggcaactga aagttgaccc gcttcatgcc tggcgtgtct gccaggctgg   6420
ccaacgttgc agccttgctg ctgcgtgcgc tcggacggcc ggcacttagc gtgtttgtgc   6480
ttttgctcat tttctcttta cctcattaac tcaaatgagt tttgatttaa tttcagcggc   6540
cagcgcctgg acctcgcggg cagcgtcgcc ctcgggttct gattcaagaa cggttgtgcc   6600
```

```
ggcggcggca gtgcctgggt agctcacgcg ctgcgtgata cgggactcaa gaatgggcag    6660
ctcgtacccg gccagcgcct cggcaacctc accgccgatg cgcgtgcctt tgatcgcccg    6720
cgacacgaca aaggccgctt gtagccttcc atccgtgacc tcaatgcgct gcttaaccag    6780
ctccaccagg tcggcggtgg cccatatgtc gtaagggctt ggctgcaccg gaatcagcac    6840
gaagtcggct gccttgatcg cggacacagc caagtccgcc gcctggggcg ctccgtcgat    6900
cactacgaag tcgcgccggc cgatggcctt cacgtcgcgg tcaatcgtcg ggcggtcgat    6960
gccgacaacg gttagcggtt gatcttcccg cacggccgcc caatcgcggg cactgccctg    7020
gggatcggaa tcgactaaca gaacatcggc cccggcgagt gcagggcgc gggctagatg    7080 ggttgcgatg gtcgtcttgc ctgacccgcc tttctggtta agtacagcga taaccttcat    7140
gcgttcccct tgcgtatttg tttatttact catcgcatca tatacgcagc gaccgcatga    7200
cgcaagctgt tttactcaaa tacacatcac cttttagac ggcggcgctc ggtttcttca    7260
gcggccaagc tggccggcca ggccgccagc ttggcatcag acaaaccggc caggatttca    7320
tgcagccgca cggttgagac gtgcgcgggc ggctcgaaca cgtacccggc cgcgatcatc    7380
tccgcctcga tctcttcggt aatgaaaaac ggttcgtcct ggccgtcctg gtgcggtttc    7440
atgcttgttc ctcttggcgt tcattctcgg cggccgccag ggcgtcggcc tcggtcaatg    7500
cgtcctcacg gaaggcaccg cgccgcctgg cctcggtggg cgtcacttcc tcgctgcgct    7560
caagtgcgcg gtacagggtc gagcgatgca cgccaagcag tgcagccgcc tctttcacgg    7620
tgcggccttc ctggtcgatc agctcgcggg cgtgcgcgat ctgtgccggg gtgagggtag    7680 ggcggggcc aaacttcacg cctcgggcct tggcggcctc gcgcccgctc cgggtgcggt    7740
cgatgattag ggaacgctcg aactcggcaa tgccggcgaa cacggtcaac accatgcggc    7800
cggccggcgt ggtggtgtcg gcccacggct ctgccaggct acgcaggccc gcgccggcct    7860
cctggatgcg ctcggcaatg tccagtaggt cgcgggtgct gcgggccagg cggtctagcc    7920
tggtcactgt cacaacgtcg ccagggcgta ggtggtcaag catcctggcc agctccgggc    7980
ggtcgcgcct ggtgccggtg atcttctcgg aaaacagctt ggtgcagccg gccgcgtgca    8040
gttcggcccg ttggttggtc aagtcctggt cgtcggtgct gacgcgggca tagcccagca    8100
ggccagcggc ggcgctcttg ttcatggcgt aatgtctccg gttctagtcg caagtattct    8160
actttatgcg actaaaacac gcgacaagaa aacgccagga aaagggcagg gcggcagcct    8220
gtcgcgtaac ttaggacttg tgcgacatgt cgttttcaga agacggctgc actgaacgtc    8280
agaagccgac tgcactatag cagcggaggg gttggatcaa agtactttga tcccgagggg    8340
aaccctgtgg ttggcatgca catacaaatg gacgaacgga taaaccttt cacgcccttt    8400 taaatatccg ttattctaat aaacgctctt ttctcttagg tttacccgcc aatatatcct    8460
gtcaaacact gatagtttaa actgaaggcg ggaaacgaca atctgatcca agctcaagct    8520
gctctagcat tcgccattca ggctgcgcaa ctgttgggaa gggcgatcgg tgcgggcctc    8580
ttcgctatta cgccagctgg cgaaagggg atgtgctgca aggcgattaa gttgggtaac    8640
gccagggttt tcccagtcac gacgttgtaa aacgacggcc agtgccaagc ttcattcgga    8700 gttttttgtat cttgtttcat agtttgtccc aggattagaa tgattaggca tcgaaccttc    8760
aagaatttga ttgaataaaa catcttcatt cttaagatat gaagataatc ttcaaaaggc    8820
ccctgggaat ctgaaagaag agaagcaggc ccatttatat gggaaagaac aatagtattt    8880
cttatatagg cccatttaag ttgaaaacaa tcttcaaaag tcccacatcg cttagataag    8940
aaaacgaagc tgagtttata tacagctaga gtcgaagtag tgcaaagaag ttcgggccct    9000
```

```
gttttagagc tagaaatagc aagttaaaat aaggctagtc cgttatcaac ttgaaaaagt   9060
ggcaccgagt cggtgctttt ttttgcgcac gaggtacgcc tgagcgtcta gatttgcatg   9120
cctgcaggtc aacatggtgg agcacgacac acttgtctac tccaaaaata tcaaagatac   9180
agtctcagaa gaccaaaggg caattgagac ttttcaacaa agggtaatat ccggaaacct   9240
cctcggattc cattgcccag ctatctgtca ctttattgtg aagatagtgg aaaaggaagg   9300
tggctcctac aaatgccatc attgcgataa aggaaaggcc atcgttgaag atgcctctgc   9360
cgacagtggt cccaaagatg acccccacc cacgaggagc atcgtggaaa aagaagacgt    9420
tccaaccacg tcttcaaagc aagtggattg atgtgataac atggtggagc acgacacact   9480
tgtctactcc aaaaatatca agatacagt ctcagaagac caaagggcaa ttgagacttt    9540
tcaacaaagg gtgatatccg gaaacctcct cggattccat tgcccagcta tctgtcactt   9600
tattgtgaag atagtggaaa aggaaggtgg ctcctacaaa tgccatcatt gcgataaagg   9660
aaaggccatc gttgaagatg cctctgccga cagtggtccc aaagatggac ccccacccac   9720
gaggagcatc gtggaaaaag aagacgttcc aaccacgtct tcaaagcaag tggattgatg   9780
tgatatctcc actgacgtaa gggatgacgc acaatcccac tatccttcgc aagacccttc   9840
ctctatataa ggaagttcat ttcatttgga gaggacctcg acctcaacac aacatataca   9900
aaacaaacga atctcaagca atcaagcatt ctacttctat tgcagcaatt taaatcattt   9960
ctttttaaagc aaaagcaatt ttctgaaaat tttcaccatt tacgaacgat actcgagatg  10020
gactacaagg accacgacgg agattacaaa gaccacgaca ttgattacaa ggatgatgac  10080
gacaagatgg ctcccaagaa gaagcgaaag gtgggcatcc acggcgtgcc cgctgccgac  10140
aaaaagtata gatcggact ggatattggc actaacagcg tgggatgggc cgtcatcacc   10200
gacgagtaca agtgccaag caagaagttc aaggtcctgg gaaacaccga tagacacagt   10260
atcaagaaaa atctgattgg agccctgctg ttcgactcag gggagacagc tgaagcaact  10320
aggctgaaaa gaacagctag gagacggtat actcgccgaa agaatcggat ctgctacctc  10380
caggagattt tctccaacga aatggccaag gtggacgata gtttctttca tcgcctggag  10440
gaatcattcc tggtcgagga agataagaaa cacgagaggc atcccatctt tggcaacatt  10500
gtggacgagg tcgcttatca cgaaaagtac cctacaatct atcatctgcg gaagaaactg  10560
gtggacagca ctgataaggc agacctgcgc ctgatctatc tggccctggc tcacatgatt  10620
aagtcagg ggcatttct gatcgagggc gatctgaacc cagacaattc cgatgtggac    10680
aagctgttca tccagctggt ccagacatac aatcagctgt ttgaggaaaa ccccattaat  10740
gcatctgggg tggacgcaaa agccatcctg agtgccagac tgtctaagag taggagactg  10800
gagaacctga tcgctcagct gccaggcgaa aagaaaaacg gcctgtttgg aaatctgatt  10860
gcactgtcac tgggactgac ccccaacttc aagagcaatt ttgatctggc cgaggacgct  10920
aagctccagc tgagcaagga cacctacgac gatgacctgg ataacctgct ggctcagatc  10980
ggcgatcagt acgcagacct gttcctggcc gctaagaatc tgtctgacgc catcctgctg  11040
agtgatattc tgagagtgaa caccgagatt acaaaagccc ccctgtcagc tagcatgatc  11100
aagagatatg acgagcacca tcaggatctg accctgctga aggctctggt gcggcagcag  11160
ctgcctgaga gtacaaaga aatcttcttt gatcagagca gaatgggta cgccggctat  11220
attgacggcg gagcttccca ggaggagttc tacaagtttat caaacctat tctggagaag  11280
atggacggca ctgaggaact gctggtgaaa ctgaatcggg aagacctgct gcggaagcag  11340
```

```
cgcaccttcg ataacggcag catccctcac cagattcatc tgggagagct gcacgcaatc    11400
ctgcggcgcc aggaagactt ctacccattt ctgaaggata accgggagaa gatcgaaaaa    11460
attctgactt tccgcatccc ctactatgtg gggcctctgg caagaggcaa ttcccggttt    11520
gcctggatga cccgcaagtc tgaggaaaca atcactccct gaacttcga ggaagtggtc     11580 gataagggcg cttccgcaca gtctttcatt gagaggatga caaattttga caagaacctg    11640
ccaaatgaaa aagtgctgcc caagcacagc ctgctgtacg agtatttcac cgtctataac    11700
gaactgacaa aggtgaaata cgtcactgag ggcatgagaa agcctgcctt cctgtccgga    11760
gaacagaaga aagctatcgt ggacctgctg tttaaaacca atcggaaggt gacagtcaag    11820
cagctgaaag aggactactt caagaaaatt gaatgtttcg attctgtgga gatcagtggg    11880
gtcgaagaca ggtttaacgc ctctctgggc acctaccacg atctgctgaa gatcattaag    11940
gataaagact tcctggacaa cgaggaaaat gaggacatcc tggaggacat tgtgctgacc    12000
ctgacactgt ttgaggatcg ggaaatgatc gaggaacgcc tgaagaccta cgcccatctg    12060
ttcgatgaca aagtgatgaa acagctgaag cgaaggagat acactgggtg gggccgactg    12120
agcaggaagc tgatcaatgg cattcgcgac aaacagagtg aaagacaat cctggacttt     12180 ctgaagtcag atggcttcgc taacaggaac ttcatgcagc tgattcacga tgactctctg    12240
actttcaaag gaacatcca gaaggcacag gtgtccggac aggggactc tctgcacgag      12300 catatcgcaa acctggccgg gagccctgcc atcaagaaag catcctcca gaccgtgaag     12360 gtggtggacg agctggtgaa agtcatggga agacataagc cagaaaacat cgtgattgag    12420
atggccaggg agaatcagac cacacagaaa gggcagaaga actctcggga gcgcatgaaa    12480
cgcatcgagg aaggaattaa ggaactgggg agtcagatcc tgaaagagca ccccgtggaa    12540
aacacacagc tccagaatga aagctgtat ctgtactacc tccagaatgg ccgcgatatg       12600
tacgtggacc aggagctgga tattaaccga ctgtcagatt atgacgtgga tcatatcgtc    12660
ccacagtcat tcctgaaaga tgacagcatt gacaataagg tgctgacccg cagcgacaaa    12720
aaccgaggaa agagtgataa tgtcccctca gaggaagtgg tcaagaaaat gaagaactac    12780
tggaggcagc tgctgaatgc caaactgatc acccagcgaa agtttgataa cctgacaaaa    12840
gctgagaggg ggggcctgtc cgaactggac aaagcaggct tcatcaagcg acagctggtg    12900
gagacaaggc agatcacaaa gcacgtcgct cagatcctgg acagcaggat gaacaccaag    12960
tacgatgaga atgacaaact gatccgggaa gtgaaggtca ttacactgaa gtcaaaactg    13020
gtgagcgact ttaggaaaga tttccagttc tacaaggtca gagagatcaa caactaccac    13080
catgctcatg acgcatacct gaacgcagtg gtcgggactg ccctgattaa gaaataccct    13140
aaactggagt ctgagttcgt gtacggcgac tataaggtgt acgatgtcag aaaaatgatc    13200
gccaagagcg agcaggaaat tggcaaagcc accgctaagt atttctttta ctccaacatc    13260
atgaatttct ttaagactga gatcaccctg gcaaatggcg aaatccgaaa gaggccactg    13320
attgagacta acggagagac aggggaaatc gtgtgggaca aaggaagaga ttttgctacc    13380
gtgcggaagg tcctgagtat gccccaagtg aatattgtca agaaaacaga ggtgcagact    13440
ggagggttca gtaaggaatc aattctgcct aaacgcaaca gcgataagct gatcgcccga    13500
aagaaagact gggaccccaa gaagtatggc ggattcgact ccccaaccgt ggcttactct    13560
gtcctggtgg tcgcaaaggt ggagaaggga aaaagcaaga actgaaatc cgtcaaggaa    13620 ctgctgggga tcacaattat ggagaggagc agcttcgaaa agaatccat cgattttctg    13680 gaggccaaag ggtataagga agtgaagaaa gacctgatca tcaagctgcc aaagtactct    13740
```

```
ctgtttgagc tggaaaacgg cagaaagcgg atgctggcaa gtgccggcga gctgcaaaaa    13800
ggaaatgaac tggccctgcc ctcaaagtac gtgaacttcc tgtatctggc tagccactac    13860
gagaagctga aaggctcccc tgaggataac gaacagaaac agctgtttgt ggagcagcac    13920
aagcattatc tggacgagat cattgaacag attagcgagt ctccaaacg cgtgatcctg     13980 gctgacgcaa atctggataa ggtcctgtct gcatacaaca acacaggga caagccaatc     14040 agagagcagg ccgaaaatat cattcatctg ttcactctga ccaacctggg agcccccgca    14100
gccttcaagt attttgacac taccatcgat cgcaaacgat acacaagcac taaggaggtg    14160
ctggatgcta ccctgatcca ccagagcatt actgggctgt acgagacaag gatcgacctg    14220
tcccagctgg ggggagacaa acgcccagcc gccaccaaga agcaggaca ggcaaagaag      14280 aagaagtgag agctctgatt gatcgataga gctcgaattt ccccgatcgt tcaaacattt    14340
ggcaataaag tttcttaaga ttgaatcctg ttgccggtct tgcgatgatt atcatataat    14400
ttctgttgaa ttacgttaag catgtaataa ttaacatgta atgcatgacg ttatttatga    14460
gatgggtttt tatgattaga gtcccgcaat tatacattta atacgcgata gaaaacaaaa    14520
tatagcgcgc aaactaggat aaattatcgc gcgcggtgtc atctatgtta ctagatcggg    14580
gatccgaatt c                                                         14591

<210> SEQ ID NO 17
<211> LENGTH: 23
<212> TYPE: DNA
<213> ORGANISM: Artificial Sequence
<220> FEATURE:
<223> OTHER INFORMATION: guide for ObHSK

<400> SEQUENCE: 17
gccaccgtcg ccaacttggg ccc                                             23

<210> SEQ ID NO 18
<211> LENGTH: 19
<212> TYPE: DNA
<213> ORGANISM: Artificial Sequence
<220> FEATURE:
<223> OTHER INFORMATION: guide for Ob2OGO

<400> SEQUENCE: 18
gcaaagaagt tcgggccct                                                  19

<210> SEQ ID NO 19
<211> LENGTH: 295
<212> TYPE: DNA
<213> ORGANISM: Arabidopsis thaliana

<400> SEQUENCE: 19
aagcttcatt cggagttttt gtatcttgtt tcatagtttg tcccaggatt agaatgatta    60
ggcatcgaac cttcaagaat ttgattgaat aaaacatctt cattcttaag atatgaagat    120
aatcttcaaa aggcccctgg gaatctgaaa gaagagaagc aggcccattt atatgggaaa    180
gaacaatagt atttcttata taggcccatt taagttgaaa acaatcttca aaagtcccac    240
atcgcttaga taagaaaacg aagctgagtt tatatacagc tagagtcgaa gtagt          295

<210> SEQ ID NO 20
<211> LENGTH: 14595
<212> TYPE: DNA
<213> ORGANISM: Artificial Sequence
<220> FEATURE:
```

<223> OTHER INFORMATION: Vector pRD322

<400> SEQUENCE: 20

```
gtaatcatgg tcatagctgt ttcctgtgtg aaattgttat ccgctcacaa ttccacacaa        60
catacgagcc ggaagcataa agtgtaaagc ctggggtgcc taatgagtga gctaactcac       120
attaattgcg ttgcgctcac tgcccgcttt ccagtcggga aacctgtcgt gccagctgca       180
ttaatgaatc ggccaacgcg cggggagagg cggtttgcgt attggctaga gcagcttgcc       240
aacatggtgg agcacgacac tctcgtctac tccaagaata tcaaagatac agtctcagaa       300
gaccaaaggg ctattgagac ttttcaacaa agggtaatat cgggaaacct cctcggattc       360
cattgcccag ctatctgtca cttcatcaaa aggacagtag aaaaggaagg tggcacctac       420
aaatgccatc attgcgataa aggaaaggct atcgttcaag atgcctctgc cgacagtggt       480
cccaaagatg accccaccc cacgaggagc atcgtggaaa aagaagacgt tccaaccacg        540
tcttcaaagc aagtggattg atgtgataac atggtggagc acgacactct cgtctactcc       600
aagaatatca agatacagt ctcagaagac caaagggcta ttgagacttt tcaacaaagg        660
gtaatatcgg gaaacctcct cggattccat tgcccagcta tctgtcactt catcaaaagg       720
acagtagaaa aggaaggtgg cacctacaaa tgccatcatt gcgataaagg aaaggctatc       780
gttcaagatg cctctgccga cagtggtccc aaagatggac ccccacccac gaggagcatc       840
gtggaaaaag aagacgttcc aaccacgtct tcaaagcaag tggattgatg tgatatctcc       900
actgacgtaa gggatgacgc acaatcccac tatccttcgc aagaccttcc tctatataag       960
gaagttcatt tcatttggag aggacacgct gaaatcacca gtctctctct acaaatctat      1020
ctctctcgag ctttcgcaga tctgtcgatc gaccatgggg attgaacaag atggattgca      1080
cgcaggttct ccggccgctt gggtggagag gctattcggc tatgactggg cacaacagac      1140
aatcggctgc tctgatgccg ccgtgttccg gctgtcagcg caggggcgcc cggttctttt      1200
tgtcaagacc gacctgtccg gtgccctgaa tgaactccag gacgaggcag cgcggctatc      1260
gtggctggcc acgacgggcg ttccttgcgc agctgtgctc gacgttgtca ctgaagcggg      1320
aagggactgg ctgctattgg gcgaagtgcc ggggcaggat ctcctgtcat ctcaccttgc      1380
tcctgccgag aaagtatcca tcatggctga tgcaatgcgg cggctgcata cgcttgatcc      1440
ggctacctgc ccattcgacc accaagcgaa acatcgcatc gagcgagcac gtactcggat      1500
ggaagccggt cttgtcgatc aggatgatct ggacgaagag catcaggggc tcgcgccagc      1560
cgaactgttc gccaggctca aggcgcgcat gcccgacggc gaggatctcg tcgtgacaca      1620
tggcgatgcc tgcttgccga atatcatggt ggaaaatggc cgcttttctg gattcatcga      1680
ctgtggccgg ctgggtgtgg cggaccgcta tcaggacata gcgttggcta cccgtgatat      1740
tgctgaagag cttggcggcg aatgggctga ccgcttcctc gtgctttacg gtatcgccgc      1800
tcccgattcg cagcgcatcg ccttctatcg ccttcttgac gagttcttct gagcgggact      1860
ctggggttcg gatcgatcct ctagctagag tcgatcgaca agctcgagtt tctccataat      1920
aatgtgtgag tagttcccag ataagggaat tagggttcct ataggggtttc gctcatgtgt      1980
tgagcatata agaaaccctt agtatgtatt tgtatttgta aaatacttct atcaataaaa      2040
tttctaattc ctaaaaccaa aatccagtac taaaatccag atccccgaa ttaattcggc        2100
gttaattcag tacattaaaa acgtccgcaa tgtgttatta agttgtctaa gcgtcaattt      2160
gtttacacca atatatatcc tgccaccagc cagccaacag ctccccgacc ggcagctcgg      2220
cacaaaatca ccactcgata caggcagccc atcagtccgg gacggcgtca gcgggagagc      2280
```

```
cgttgtaagg cggcagactt tgctcatgtt accgatgcta ttcggaagaa cggcaactaa      2340
gctgccgggt ttgaaacacg gatgatctcg cggagggtag catgttgatt gtaacgatga      2400
cagagcgttg ctgcctgtga tcaccgcggt ttcaaaatcg gctccgtcga tactatgtta      2460
tacgccaact ttgaaaacaa cttgaaaaa gctgttttct ggtatttaag gttttagaat       2520
gcaaggaaca gtgaattgga gttcgtcttg ttataattag cttcttgggg tatctttaaa      2580
tactgtagaa aagaggaagg aaataataaa tggctaaaat gagaatatca ccggaattga      2640
aaaaactgat cgaaaatac cgctgcgtaa aagatacgga aggaatgtct cctgctaagg        2700
tatataagct ggtgggagaa aatgaaaacc tatatttaaa aatgacggac agccggtata      2760
aagggaccac ctatgatgtg aacgggaaa aggacatgat gctatggctg aaggaaagc        2820 tgcctgttcc aaaggtcctg cactttgaac ggcatgatgg ctggagcaat ctgctcatga      2880
gtgaggccga tggcgtcctt tgctcggaag agtatgaaga tgaacaaagc cctgaaaaga      2940
ttatcgagct gtatgcggag tgcatcaggc tctttcactc catcgacata tcggattgtc      3000
cctatacgaa tagcttagac agccgcttag ccgaattgga ttacttactg aataacgatc      3060
tggccgatgt ggattgcgaa aactgggaag aagacactcc atttaaagat ccgcgcgagc      3120
tgtatgattt tttaaagacg gaaaagcccg aagaggaact tgtcttttcc cacggcgacc      3180
tgggagacag caacatcttt gtgaaagatg gcaaagtaag tggctttatt gatcttggga      3240
gaagcggcag ggcggacaag tggtatgaca ttgccttctg cgtccggtcg atcagggagg      3300
atatcgggga agaacagtat gtcgagctat tttttgactt actggggatc aagcctgatt      3360
gggagaaaat aaaatattat attttactgg atgaattgtt ttagtaccta gaatgcatga      3420
ccaaaatccc ttaacgtgag ttttcgttcc actgagcgtc agaccccgta gaaaagatca      3480
aaggatcttc ttgagatcct ttttttctgc gcgtaatctg ctgcttgcaa acaaaaaaac      3540
caccgctacc agcggtggtt tgtttgccgg atcaagagct accaactctt tttccgaagg      3600
taactggctt cagcagagcg cagataccaa atactgtcct tctagtgtag ccgtagttag      3660
gccaccactt caagaactct gtagcaccgc ctacatacct cgctctgcta atcctgttac      3720
cagtggctgc tgccagtggc gataagtcgt gtcttaccgg gttggactca agacgatagt      3780
taccggataa ggcgcagcgg tcgggctgaa cggggggttc gtgcacacag cccagcttgg      3840
agcgaacgac ctacaccgaa ctgagatacc tacagcgtga gctatgagaa agcgccacgc      3900
ttcccgaagg gagaaaggcg gacaggtatc cggtaagcgg cagggtcgga acaggagagc      3960
gcacgaggga gcttccaggg ggaaacgcct ggtatcttta tagtcctgtc gggtttcgcc      4020
acctctgact tgagcgtcga ttttttgtgat gctcgtcagg ggggcggagc ctatggaaaa      4080
acgccagcaa cgcggccttt ttacggttcc tggccttttg ctggcctttt gctcacatgt      4140
tctttcctgc gttatcccct gattctgtgg ataaccgtat taccgccttt gagtgagctg      4200
ataccgctcg ccgcagccga acgaccgagc gcagcgagtc agtgagcgag gaagcggaag      4260
agcgcctgat gcggtatttt ctccttacgc atctgtgcgg tatttcacac cgcatatggt      4320
gcactctcag tacaatctgc tctgatgccg catagttaag ccagtataca ctccgctatc      4380
gctacgtgac tgggtcatgg ctgcgccccg acacccgcca cacccgctg acgcgccctg        4440 acgggcttgt ctgctcccgg catccgctta cagacaagct gtgaccgtct ccgggagctg      4500
catgtgtcag aggttttcac cgtcatcacc gaaacgcgcg aggcagggtg ccttgatgtg      4560
ggcgccggcg gtcgagtggc gacggcgcgg cttgtccgcg ccctggtaga ttgcctggcc      4620
```

```
gtaggccagc cattttttgag cggccagcgg ccgcgatagg ccgacgcgaa gcggcggggc    4680
gtagggagcg cagcgaccga agggtaggcg cttttttgcag ctcttcggct gtgcgctggc    4740
cagacagtta tgcacaggcc aggcgggttt taagagtttt aataagtttt aaagagtttt    4800
aggcggaaaa atcgccttttt ttctctttta tatcagtcac ttacatgtgt gaccggttcc    4860
caatgtacgg ctttgggttc ccaatgtacg ggttccggtt cccaatgtac ggctttgggt    4920
tcccaatgta cgtgctatcc acaggaaaga gacctttttcg acctttttttcc cctgctaggg    4980 caatttgccc tagcatctgc tccgtacatt aggaaccggc ggatgcttcg ccctcgatca    5040
ggttgcggta gcgcatgact aggatcgggc cagcctgccc cgcctcctcc ttcaaatcgt    5100
actccggcag gtcatttgac ccgatcagct tgcgcacggt gaaacagaac ttcttgaact    5160
ctccggcgct gccactgcgt tcgtagatcg tcttgaacaa ccatctggct tctgccttgc    5220
ctgcggcgcg gcgtgccagg cggtagagaa acggccgat gccgggatcg atcaaaaagt    5280
aatcggggtg aaccgtcagc acgtccgggt tcttgccttc tgtgatctcg cggtacatcc    5340
aatcagctag ctcgatctcg atgtactccg gccgccggt ttcgctcttt acgatcttgt    5400
agcggctaat caaggcttca ccctcggata ccgtcaccag gcggccgttc ttggccttct    5460
tcgtacgctg catggcaacg tgcgtggtgt ttaaccgaat gcaggtttct accaggtcgt    5520
ctttctgctt ccgccatcg gctcgccggc agaacttgag tacgtccgca acgtgtggac    5580
ggaacacgcg gccgggcttg tctcccttcc cttcccggta tcggttcatg gattcggtta    5640
gatgggaaac cgccatcagt accaggtcgt aatcccacac actggccatg ccggccggcc    5700
ctgcggaaac ctctacgtgc ccgtctggaa gctcgtagcg gatcacctcg ccagctcgtc    5760
ggtcacgctt cgacagacgg aaaacggcca cgtccatgat gctgcgacta tcgcgggtgc    5820
ccacgtcata gagcatcgga acgaaaaaat ctggttgctc gtcgcccttg ggcggcttcc    5880
taatcgacgg cgcaccggct gccggcggtt gccgggattc tttgcggatt cgatcagcgg    5940
ccgcttgcca cgattcaccg gggcgtgctt ctgcctcgat gcgttgccgc tgggcggcct    6000
gcgcggcctt caacttctcc accaggtcat cacccagcgc cgcgccgatt tgtaccgggc    6060
cggatggttt gcgaccgctc acgccgattc ctcgggcttg ggggttccag tgccattgca    6120
gggccggcag acaacccagc cgcttacgcc tggccaaccg cccgttcctc cacacatggg    6180
gcattccacg gcgtcggtgc ctggttgttc ttgattttcc atgccgcctc ctttagccgc    6240
taaaattcat ctactcattt attcatttgc tcatttactc tggtagctgc gcgatgtatt    6300
cagatagcag ctcggtaatg gtcttgcctt ggcgtaccgc gtacatcttc agcttggtgt    6360
gatcctccgc cggcaactga aagttgaccc gcttcatggc tggcgtgtct gccaggctgg    6420
ccaacgttgc agccttgctg ctgcgtgcgc tcggacggcc ggcacttagc gtgtttgtgc    6480
ttttgctcat tttctctttta cctcattaac tcaaatgagt tttgatttaa tttcagcggc    6540
cagcgcctgg acctcgcggg cagcgtcgcc ctcgggttct gattcaagaa cggttgtgcc    6600
ggcggcggca gtgcctgggt agctcacgcg ctgcgtgata cgggactcaa gaatgggcag    6660
ctcgtacccg gccagcgcct cggcaacctc accgccgatg cgcgtgcctt tgatcgcccg    6720
cgacacgaca aaggccgctt gtagccttcc atccgtgacc tcaatgcgct gcttaaccag    6780
ctccaccagg tcggcggtgg cccatatgtc gtaagggctt ggctgcaccg gaatcagcac    6840
gaagtcggct gccttgatcg cggacacagc caagtccgcc gcctggggcg ctccgtcgat    6900
cactacgaag tcgcgccggc cgatggcctt acgtcgcgg tcaatcgtcg ggcggtcgat    6960
gccgacaacg gttagcggtt gatcttcccg cacggccgcc caatcgcggg cactgccctg    7020
```

```
gggatcggaa tcgactaaca gaacatcggc cccggcgagt tgcagggcgc gggctagatg    7080
ggttgcgatg gtcgtcttgc ctgacccgcc tttctggtta agtacagcga taaccttcat    7140
gcgttcccct tgcgtatttg tttatttact catcgcatca tatacgcagc gaccgcatga    7200
cgcaagctgt tttactcaaa tacacatcac cttttagac ggcggcgctc ggtttcttca     7260
gcggccaagc tggccggcca ggccgccagc ttggcatcag acaaaccggc caggatttca    7320
tgcagccgca cggttgagac gtgcgcgggc ggctcgaaca cgtacccggc cgcgatcatc    7380
tccgcctcga tctcttcggt aatgaaaaac ggttcgtcct ggccgtcctg gtgcggtttc    7440
atgcttgttc ctcttggcgt tcattctcgg cggccgccag ggcgtcggcc tcggtcaatg    7500
cgtcctcacg gaaggcaccg cgccgcctgg cctcggtggg cgtcacttcc tcgctgcgct    7560
caagtgcgcg gtacagggtc gagcgatgca cgccaagcag tgcagccgcc tctttcacgg    7620
tgcggccttc ctggtcgatc agctcgcggg cgtgcgcgat ctgtgccggg gtgagggtag    7680
ggcggggggc aaacttcacg cctcgggcct tggcggcctc gcgcccgctc cgggtgcggt    7740
cgatgattag ggaacgctcg aactcggcaa tgccggcgaa cacggtcaac accatgcggc    7800
cggccggcgt ggtggtgtcg gcccacggct ctgccaggct acgcaggccc gcgcggcct     7860
cctggatgcg ctcggcaatg tccagtaggt cgcgggtgct gcgggccagg cggtctagcc    7920
tggtcactgt cacaacgtcg ccagggcgta ggtggtcaag catcctggcc agctccgggc    7980
ggtcgcgcct ggtgccggtg atcttctcgg aaaacagctt ggtgcagccg ccgcgtgca    8040
gttcggcccg ttggttggtc aagtcctggt cgtcggtgct gacgcgggca tagcccagca    8100
ggccagcggc ggcgctcttg ttcatggcgt aatgtctccg gttctagtcg caagtattct    8160
actttatgcg actaaaacac gcgacaagaa aacgccagga aaagggcagg gcggcagcct    8220
gtcgcgtaac ttaggacttg tgcgacatgt cgttttcaga agacggctgc actgaacgtc    8280
agaagccgac tgcactatag cagcggaggg gttggatcaa agtactttga tcccgagggg    8340
aaccctgtgg ttggcatgca catacaaatg gacgaacgga taaaccttt cacgcccttt     8400
taaatatccg ttattctaat aaacgctctt ttctcttagg tttacccgcc aatatatcct    8460
gtcaaacact gatagtttaa actgaaggcg ggaaacgaca atctgatcca agctcaagct    8520
gctctagcat tcgccattca ggctgcgcaa ctgttgggaa gggcgatcgg tgcgggcctc    8580
ttcgctatta cgccagctgg cgaaaggggg atgtgctgca aggcgattaa gttgggtaac    8640
gccagggttt tcccagtcac gacgttgtaa aacgacggcc agtgccaagc ttcattcgga    8700
gtttttgtat cttgtttcat agtttgtccc aggattagaa tgattaggca tcgaaccttc    8760
aagaatttga ttgaataaaa catcttcatt cttaagatat gaagataatc ttcaaaggc     8820
ccctgggaat ctgaaagaag agaagcaggc ccatttatat gggaagaac aatagtattt     8880
cttatatagg cccatttaag ttgaaaacaa tcttcaaaag tcccacatcg cttagataag    8940
aaaacgaagc tgagtttata tacagctaga gtcgaagtag tgccaccgtc gccaacttgg    9000
gcccgtttta gagctagaaa tagcaagtta aaataaggct agtccgttat caacttgaaa    9060
aagtggcacc gagtcggtgc tttttttgc gcacgaggta cgcctgagcg tctagatttg     9120
catgcctgca ggtcaacatg gtggagcacg acacacttgt ctactccaaa aatatcaaag    9180
atacagtctc agaagaccaa agggcaattg agacttttca acaaagggta atatccggaa    9240
acctcctcgg attccattgc ccagctatct gtcactttat tgtgaagata gtggaaaagg    9300
aaggtggctc ctacaaatgc catcattgcg ataaaggaaa ggccatcgtt gaagatgcct    9360
```

```
ctgccgacag tggtcccaaa gatggacccc cacccacgag gagcatcgtg gaaaaagaag   9420
acgttccaac cacgtcttca aagcaagtgg attgatgtga taacatggtg gagcacgaca   9480
cacttgtcta ctccaaaaat atcaaagata cagtctcaga agaccaaagg gcaattgaga   9540
cttttcaaca aagggtgata tccggaaacc tcctcggatt ccattgccca gctatctgtc   9600
actttattgt gaagatagtg gaaaaggaag gtggctccta caaatgccat cattgcgata   9660
aaggaaaggc catcgttgaa gatgcctctg ccgacagtgg tcccaaagat ggaccccac    9720 ccacgaggag catcgtggaa aaagaagacg ttccaaccac gtcttcaaag caagtggatt   9780
gatgtgatat ctccactgac gtaagggatg acgcacaatc ccactatcct tcgcaagacc   9840
cttcctctat ataaggaagt tcatttcatt tggagaggac ctcgacctca acacaacata   9900
tacaaaacaa acgaatctca agcaatcaag cattctactt ctattgcagc aatttaaatc   9960 atttcttta aagcaaaagc aattttctga aaattttcac catttacgaa cgatactcga   10020
gatggactac aaggaccacg acggagatta caaagaccac gacattgatt acaaggatga   10080
tgacgacaag atggctccca agaagaagcg aaaggtgggc atccacggcg tgcccgctgc   10140
cgacaaaaag tatagtatcg gactggatat tggcactaac agcgtgggat gggccgtcat   10200
caccgacgag tacaaagtgc caagcaagaa gttcaaggtc ctgggaaaca ccgatagaca   10260
cagtatcaag aaaaatctga ttggagccct gctgttcgac tcaggggaga cagctgaagc   10320
aactaggctg aaaagaacag ctaggagacg gtatactcgc cgaaagaatc ggatctgcta   10380
cctccaggag attttctcca acgaaatggc caaggtggac gatagtttct ttcatcgcct   10440
ggaggaatca ttcctggtcg aggaagataa gaaacacgag aggcatccca tctttggcaa   10500
cattgtggac gaggtcgctt atcacgaaaa gtaccctaca atctatcatc tgcggaagaa   10560
actggtggac agcactgata aggcagacct gcgcctgatc tatctggccc tggctcacat   10620
gattaagttc agggggcatt ttctgatcga gggcgatctg aacccagaca attccgatgt   10680
ggacaagctg ttcatccagc tggtccagac atacaatcag ctgtttgagg aaaaccccat   10740
taatgcatct ggggtggacg caaaagccat cctgagtgcc agactgtcta agagtaggag   10800
actggagaac ctgatcgctc agctgccagg cgaaaagaaa aacggcctgt ttggaaatct   10860
gattgcactg tcactgggac tgaccccaa cttcaagagc aattttgatc tggccgagga   10920
cgctaagctc cagctgagca aggacaccta cgacgatgac ctggataacc tgctggctca   10980
gatcggcgat cagtacgcag acctgttcct ggccgctaag aatctgtctg acgccatcct   11040
gctgagtgat attctgagag tgaacaccga gattacaaaa gccccctgt cagctagcat    11100 gatcaagaga tatgacgagc accatcagga tctgacectg ctgaaggctc tggtgcggca   11160
gcagctgcct gagaagtaca agaaatctct ctttgatcag agcaagaatg ggtacgccgg   11220
ctatattgac ggcggagctt cccaggagga gttctacaag tttatcaaac ctattctgga   11280
gaagatggac ggcactgagg aactgctggt gaaactgaat cgggaagacc tgctgcggaa   11340
gcagcgcacc ttcgataacg gcagcatccc tcaccagatt catctgggag agctgcacgc   11400
aatcctgcgg cgccaggaag acttctaccc atttctgaag gataaccggg agaagatcga   11460
aaaaattctg actttccgca tcccctacta tgtgggccct ctggcaagag gcaattcccg   11520
gtttgcctgg atgacccgca agtctgagga aacaatcact ccctggaact tcgaggaagt   11580
ggtcgataag ggcgcttccg cacagtcttt cattgagagg atgacaaatt ttgacaagaa   11640
cctgccaaat gaaaaagtgc tgcccaagca cagcctgctg tacgagtatt tcaccgtcta   11700
taacgaactg acaaaggtga aatacgtcac tgagggcatg agaaagcctg ccttcctgtc   11760
```

```
cggagaacag aagaaagcta tcgtggacct gctgtttaaa accaatcgga aggtgacagt   11820
caagcagctg aaagaggact acttcaagaa aattgaatgt ttcgattctg tggagatcag   11880
tggggtcgaa gacaggttta acgcctctct gggcacctac cacgatctgc tgaagatcat   11940
taaggataaa gacttcctgg acaacgagga aaatgaggac atcctggagg acattgtgct   12000
gaccctgaca ctgtttgagg atcgggaaat gatcgaggaa cgcctgaaga cctacgccca   12060
tctgttcgat gacaaagtga tgaaacagct gaagcgaagg agatacactg ggtggggccg   12120
actgagcagg aagctgatca atggcattcg cgacaaacag agtggaaaga caatcctgga   12180
ctttctgaag tcagatggct tcgctaacag gaacttcatg cagctgattc acgatgactc   12240
tctgactttc aaagaggaca tccagaaggc acaggtgtcc ggacaggggg actctctgca   12300
cgagcatatc gcaaacctgg ccgggagccc tgccatcaag aaaggcatcc tccagaccgt   12360
gaaggtggtg gacgagctgg tgaaagtcat gggaagacat aagccagaaa acatcgtgat   12420
tgagatggcc agggagaatc agaccacaca gaaagggcaa gaactctc gggagcgcat   12480 gaaacgcatc gaggaaggaa ttaaggaact ggggagtcag atcctgaaag agcacccgt   12540 ggaaaacaca cagctccaga tgagaagct gtatctgtac tacctccaga atggccgcga   12600
tatgtacgtg gaccaggagc tggatattaa ccgactgtca gattatgacg tggatcatat   12660
cgtcccacag tcattcctga agatgacaca cattgacaat aaggtgctga cccgcagcga   12720 caaaaccga ggaaagagtg ataatgtccc ctcagaggaa gtggtcaaga aaatgaagaa   12780
ctactggagg cagctgctga atgccaaact gatcacccag cgaaagtttg ataacctgac   12840
aaaagctgag aggggggcc tgtccgaact ggacaaagca ggcttcatca agcgacagct   12900
ggtggagaca aggcagatca caaagcacgt cgctcagatc ctggacagca ggatgaacac   12960
caagtacgat gagaatgaca aactgatccg ggaagtgaag gtcattacac tgaagtcaaa   13020
actggtgagc gactttagga agatttccca gttctacaag gtcagagaga tcaacaacta   13080
ccaccatgct catgacgcat acctgaacgc agtggtcggg actgccctga ttaagaaata   13140
ccctaaactg gagtctgagt tcgtgtacgg cgactataag gtgtacgatg tcagaaaaat   13200
gatcgccaag agcgagcagg aaattggcaa agccaccgct aagtatttct tttactccaa   13260
catcatgaat ttcttttaaga ctgagatcac cctggcaaat ggcgaaatcc gaaagaggcc   13320
actgattgag actaacggag agacagggga aatcgtgtgg gacaaaggaa gagattttgc   13380
taccgtgcgg aaggtcctga gtatgcccca agtgaatatt gtcaagaaaa cagaggtgca   13440
gactggaggg ttcagtaagg aatcaattct gcctaaacgc aacagcgata gctgatcgc   13500 ccgaaagaaa gactgggacc ccaagaagta tggcggattc gactccccaa ccgtggctta   13560
ctctgtcctg gtggtcgcaa aggtggagaa gggaaaaagc aagaaactga atccgtcaa   13620 ggaactgctg gggatcacaa ttatggagag gagcagcttc gaaaagaatc ctatcgattt   13680
tctggaggcc aaagggtata aggaagtgaa gaaagacctg atcatcaagc tgccaaagta   13740
ctctctgttt gagctggaaa acggcagaaa gcggatgctg gcaagtgccg cgagctgca   13800 aaaaggaaat gaactggccc tgccctcaaa gtacgtgaac ttcctgtatc tggctagcca   13860
ctacgagaag ctgaaaggct cccctgagga taacgaacag aaacagctgt ttgtggagca   13920
gcacaagcat tatctggacg agatcattga acagattagc gagttctcca acgcgtgat   13980 cctggctgac gcaaatctgg ataaggtcct gtctgcatac aacaaacaca gggacaagcc   14040
aatcagagag caggccgaaa atatcattca tctgttcact ctgaccaacc tgggagcccc   14100
```

```
cgcagccttc aagtattttg acactaccat cgatcgcaaa cgatacacaa gcactaagga      14160
ggtgctggat gctaccctga tccaccagag cattactggg ctgtacgaga caaggatcga      14220
cctgtcccag ctgggggag acaaacgccc agccgccacc aagaaagcag acaggcaaa        14280 gaagaagaag tgagagctct gattgatcga tagagctcga atttccccga tcgttcaaac      14340
atttggcaat aaagtttctt aagattgaat cctgttgccg gtcttgcgat gattatcata     14400
taatttctgt tgaattacgt taagcatgta ataattaaca tgtaatgcat gacgttattt     14460
atgagatggg tttttatgat tagagtcccg caattataca tttaatacgc gatagaaaac     14520
aaaatatagc gcgcaaacta ggataaatta tcgcgcgcgg tgtcatctat gttactagat     14580
cggggatccg aattc                                                      14595
```

<210> SEQ ID NO 21
<211> LENGTH: 14595
<212> TYPE: DNA
<213> ORGANISM: Artificial Sequence
<220> FEATURE:
<223> OTHER INFORMATION: Vector pRD488

<400> SEQUENCE: 21

```
gtaatcatgg tcatagctgt ttcctgtgtg aaattgttat ccgctcacaa ttccacacaa        60
catacgagcc ggaagcataa agtgtaaagc ctggggtgcc taatgagtga gctaactcac       120
attaattgcg ttgcgctcac tgcccgcttt ccagtcggga aacctgtcgt gccagctgca       180
ttaatgaatc ggccaacgcg cggggagagg cggtttgcgt attggctaga gcagcttgcc       240
aacatggtgg agcacgacac tctcgtctac tccaagaata tcaaagatac agtctcagaa       300
gaccaaaggg ctattgagac ttttcaacaa agggtaatat cgggaaacct cctcggattc       360
cattgcccag ctatctgtca cttcatcaaa aggacagtag aaaaggaagg tggcacctac       420
aaatgccatc attgcgataa aggaaaggct atcgttcaag atgcctctgc cgacagtggt       480
cccaaagatg gaccccccacc cacgaggagc atcgtggaaa aagaagacgt tccaaccacg      540
tcttcaaagc aagtggattg atgtgataac atggtggagc acgacactct cgtctactcc      600
aagaatatca agatacagt ctcagaagac caaagggcta ttgactttt caacaaagg         660 gtaatatcgg gaaacctcct cggattccat tgcccagcta tctgtcactt catcaaaagg      720
acagtagaaa aggaaggtgg cacctacaaa tgccatcatt gcgataaagg aaaggctatc      780
gttcaagatg cctctgccga cagtggtccc aaagatggac ccccacccac gaggagcatc      840
gtggaaaaag aagacgttcc aaccacgtct tcaaagcaag tggattgatg tgatatctcc      900
actgacgtaa gggatgacgc acaatcccac tatccttcgc aagaccttcc tctatataag      960
gaagttcatt tcatttggag aggacacgct gaaatcacca gtctctctct acaaatctat     1020
ctctctcgag ctttcgcaga tctgtcgatc gaccatgggg attgaacaag atggattgca     1080
cgcaggttct ccggccgctt gggtggagag gctattcggc tatgactggg cacaacagac     1140
aatcggctgc tctgatgccg ccgtgttccg gctgtcagcg caggggcgcc cggttctttt     1200
tgtcaagacc gacctgtccg gtgccctgaa tgaactccag gacgaggcag cgcggctatc     1260
gtggctggcc acgacgggcg ttccttgcgc agctgtgctc gacgttgtca ctgaagcggg     1320
aagggactgg ctgctattgg gcgaagtgcc ggggcaggat ctcctgtcat ctcaccttgc     1380
tcctgccgag aaagtatcca tcatggctga tgcaatgcgg cggctgcata cgcttgatcc     1440
ggctacctgc ccattcgacc accaagcgaa acatcgcatc gagcgagcac gtactcggat     1500
ggaagccggt cttgtcgatc aggatgatct ggacgaagag catcaggggc tcgcgccagc     1560
```

```
cgaactgttc gccaggctca aggcgcgcat gcccgacggc gaggatctcg tcgtgacaca    1620
tggcgatgcc tgcttgccga atatcatggt ggaaaatggc cgcttttctg gattcatcga    1680
ctgtggccgg ctgggtgtgg cggaccgcta tcaggacata gcgttggcta cccgtgatat    1740
tgctgaagag cttggcggcg aatgggctga ccgcttcctc gtgctttacg gtatcgccgc    1800
tcccgattcg cagcgcatcg ccttctatcg ccttcttgac gagttcttct gagcgggact    1860
ctggggttcg gatcgatcct ctagctagag tcgatcgaca agctcgagtt tctccataat    1920
aatgtgtgag tagttcccag ataagggaat tagggttcct atagggtttc gctcatgtgt    1980
tgagcatata agaaaccctt agtatgtatt tgtatttgta aaatacttct atcaataaaa    2040
tttctaattc ctaaaaccaa aatccagtac taaaatccag atcccccgaa ttaattcggc    2100
gttaattcag tacattaaaa acgtccgcaa tgtgttatta agttgtctaa gcgtcaattt    2160
gtttacacca caatatatcc tgccaccagc cagccaacag ctccccgacc ggcagctcgg    2220
cacaaaatca ccactcgata caggcagccc atcagtccgg gacggcgtca gcgggagagc    2280
cgttgtaagg cggcagactt tgctcatgtt accgatgcta ttcggaagaa cggcaactaa    2340
gctgccgggt ttgaaacacg gatgatctcg cggagggtag catgttgatt gtaacgatga    2400
cagagcgttg ctgcctgtga tcaccgcggt ttcaaaatcg gctccgtcga tactatgtta    2460
tacgccaact ttgaaaacaa cttttgaaaaa gctgttttct ggtatttaag gttttagaat    2520
gcaaggaaca gtgaattgga gttcgtcttg ttataattag cttcttgggg tatctttaaa    2580
tactgtagaa aagaggaagg aaataataaa tggctaaaat gagaatatca ccggaattga    2640
aaaaactgat cgaaaaatac cgctgcgtaa aagatacgga aggaatgtct cctgctaagg    2700
tatataagct ggtgggagaa aatgaaaacc tatatttaaa aatgacggac agccggtata    2760
aagggaccac ctatgatgtg aacgggaaa aggacatgat gctatggctg aaggaaaagc    2820
tgcctgttcc aaaggtcctg cactttgaac ggcatgatgg ctggagcaat ctgctcatga    2880
gtgaggccga tggcgtcctt tgctcggaag agtatgaaga tgaacaaagc cctgaaaaga    2940
ttatcgagct gtatgcggag tgcatcaggc tctttcactc catcgacata tcggattgtc    3000
cctatacgaa tagcttagac agccgcttag ccgaattgga ttacttactg aataacgatc    3060
tggccgatgt ggattgcgaa aactgggaag aagacactcc atttaaagat ccgcgcgagc    3120
tgtatgattt tttaaagacg gaaaagcccg aagaggaact tgtctttttcc cacggcgacc    3180 tgggagacag caacatcttt gtgaaagatg gcaaagtaag tggctttatt gatcttggga    3240
gaagcggcag ggcggacaag tggtatgaca ttgccttctg cgtccggtcg atcagggagg    3300
atatcgggga agaacagtat gtcgagctat ttttgactt actggggatc aagcctgatt    3360
gggagaaaat aaaatattat attttactgg atgaattgtt ttagtaccta gaatgcatga    3420
ccaaaatccc ttaacgtgag ttttcgttcc actgagcgtc agaccccgta gaaaagatca    3480
aaggatcttc ttgagatcct tttttctgc gcgtaatctg ctgcttgcaa acaaaaaaac    3540
caccgctacc agcggtggtt tgtttgccgg atcaagagct accaactctt tttccgaagg    3600
taactggctt cagcagagcg cagataccaa atactgtcct tctagtgtag ccgtagttag    3660
gccaccactt caagaactct gtagcaccgc ctacatacct cgctctgcta atcctgttac    3720
cagtggctgc tgccagtggc gataagtcgt gtcttaccgg gttggactca agacgatagt    3780
taccggataa ggcgcagcgg tcgggctgaa cggggggttc gtgcacacag cccagcttgg    3840
agcgaacgac ctacaccgaa ctgagatacc tacagcgtga gctatgagaa agcgccacgc    3900
```

-continued

```
ttcccgaagg gagaaaggcg gacaggtatc cggtaagcgg cagggtcgga acaggagagc    3960
gcacgaggga gcttccaggg ggaaacgcct ggtatcttta tagtcctgtc gggtttcgcc    4020
acctctgact tgagcgtcga tttttgtgat gctcgtcagg ggggcggagc ctatggaaaa    4080
acgccagcaa cgcggccttt ttacggttcc tggccttttg ctggccttt gctcacatgt    4140 tctttcctgc gttatcccct gattctgtgg ataaccgtat taccgccttt gagtgagctg    4200
ataccgctcg ccgcagccga acgaccgagc gcagcgagtc agtgagcgag gaagcggaag    4260
agcgcctgat gcggtatttt ctccttacgc atctgtgcgg tatttcacac cgcatatggt    4320
gcactctcag tacaatctgc tctgatgccg catagttaag ccagtataca ctccgctatc    4380
gctacgtgac tgggtcatgg ctgcgccccg acacccgcca cacccgctg acgcgccctg     4440 acggcttgt ctgctcccgg catccgctta cagacaagct gtgaccgtct ccggagctg      4500 catgtgtcag aggttttcac cgtcatcacc gaaacgcgcg aggcagggtg ccttgatgtg    4560
ggcgccggcg gtcgagtggc gacggcgcgg cttgtccgcg ccctggtaga ttgcctggcc    4620
gtaggccagc cattttgag cggccagcgg ccgcgatagg ccgacgcgaa gcggcgggc     4680 gtagggagcg cagcgaccga agggtaggcg cttttttgcag ctcttcggct gtgcgctggc    4740
cagacagtta tgcacaggcc aggcgggttt taagagtttt aataagtttt aaagagtttt    4800
aggcggaaaa atcgcctttt ttctcttta tatcagtcac ttacatgtgt gaccggttcc     4860
caatgtacgg ctttgggttc ccaatgtacg ggttccggtt cccaatgtac ggctttgggt    4920
tcccaatgta cgtgctatcc acaggaaaga gaccttttcg accttttcc cctgctaggg     4980 caatttgccc tagcatctgc tccgtacatt aggaaccggc ggatgcttcg ccctcgatca    5040
ggttgcggta gcgcatgact aggatcgggc cagcctgccc cgcctcctcc ttcaaatcgt    5100
actccggcag gtcatttgac ccgatcagct tgcgcacggt gaaacagaac ttcttgaact    5160
ctccggcgct gccactgcgt tcgtagatcg tcttgaacaa ccatctggct tctgccttgc    5220
ctgcggcgcg cgtgccagg cggtagagaa acggccgat gccgggatcg atcaaaaagt      5280
aatcggggtg aaccgtcagc acgtccgggt tcttgccttc tgtgatctcg cggtacatcc    5340
aatcagctag ctcgatctcg atgtactccg gccgccggt tcgctcttt acgatcttgt     5400 agcggctaat caaggcttca ccctcggata ccgtcaccag gcggccgttc ttggccttct    5460
tcgtacgctg catggcaacg tgcgtggtgt ttaaccgaat gcaggtttct accaggtcgt    5520 cttttctgctt tccgccatcg gctcgccggc agaacttgag tacgtccgca acgtgtggac    5580
ggaacacgcg gccgggcttg tctcccttcc cttcccggta tcggttcatg gattcggtta    5640
gatgggaaac cgccatcagt accaggtcgt aatcccacac actggccatg ccggccggcc    5700
ctgcggaaac ctctacgtgc ccgtctggaa gctcgtagcg gatcacctcg ccagctcgtc    5760
ggtcacgctt cgacagacgg aaaacggcca cgtccatgat gctgcgacta tcgcgggtgc    5820
ccacgtcata gagcatcgga acgaaaaaat ctggttgctc gtcgcccttg gcggcgttcc    5880
taatcgacgg cgcaccggct gccggcggtt gccgggattc tttgcggatt cgatcagcgg    5940
ccgcttgcca cgattcaccg gggcgtgctt ctgcctcgat gcgttgccgc tgggcggcct    6000
gcgcggcctt caacttctcc accaggtcat cacccagcgc cgcgccgatt tgtaccgggc    6060
cggatggttt gcgaccgctc acgccgattc ctcgggcttg ggggttccag tgccattgca    6120
gggccggcag acaacccagc cgcttacgcc tggccaaccg cccgttcctc cacacatggg    6180
gcattccacg gcgtcggtgc ctggttgttc ttgattttcc atgccgcctc ctttagccgc    6240
taaaattcat ctactcattt attcatttgc tcatttactc tggtagctgc gcgatgtatt    6300
```

```
cagatagcag ctcggtaatg gtcttgcctt ggcgtaccgc gtacatcttc agcttggtgt   6360
gatcctccgc cggcaactga aagttgaccc gcttcatggc tggcgtgtct gccaggctgg   6420
ccaacgttgc agccttgctg ctgcgtgcgc tcggacggcc ggcacttagc gtgtttgtgc   6480
ttttgctcat tttctcttta cctcattaac tcaaatgagt tttgatttaa tttcagcggc   6540
cagcgcctgg acctcgcggg cagcgtcgcc ctcgggttct gattcaagaa cggttgtgcc   6600
ggcggcggca gtgcctgggt agctcacgcg ctgcgtgata cgggactcaa gaatgggcag   6660
ctcgtacccg gccagcgcct cggcaacctc accgccgatg cgcgtgcctt tgatcgcccg   6720
cgacacgaca aaggccgctt gtagccttcc atccgtgacc tcaatgcgct gcttaaccag   6780
ctccaccagg tcggcggtgg cccatatgtc gtaagggctt ggctgcaccg gaatcagcac   6840
gaagtcggct gccttgatcg cggacacagc caagtccgcc gcctggggcg ctccgtcgat   6900
cactacgaag tcgcgccggc cgatggcctt cacgtcgcgg tcaatcgtcg ggcggtcgat   6960
gccgacaacg gttagcggtt gatcttcccg cacggccgcc caatcgcggg cactgccctg   7020
gggatcggaa tcgactaaca gaacatcggc cccggcgagt tgcagggcgc gggctagatg   7080
ggttgcgatg tcgtcttgc ctgacccgcc tttctggtta agtacagcga taaccttcat   7140
gcgttcccct tgcgtatttg tttatttact catcgcatca tatacgcagc gaccgcatga   7200
cgcaagctgt tttactcaaa tacacatcac cttttttagac ggcggcgctc ggttttcttca   7260 gcggccaagc tggccggcca ggccgccagc ttggcatcag acaaaccggc caggatttca   7320
tgcagccgca cggttgagac gtgcgcgggc ggctcgaaca cgtacccggc cgcgatcatc   7380
tccgcctcga tctcttcggt aatgaaaaac ggttcgtcct ggccgtcctg gtgcggtttc   7440
atgcttgttc ctcttggcgt tcattctcgg cggccgccag ggcgtcggcc tcggtcaatg   7500
cgtcctcacg gaaggcaccg cgccgcctgg cctcggtggg cgtcacttcc tcgctgcgct   7560
caagtgcgcg gtacagggtc gagcgatgca cgccaagcag tgcagccgcc tctttcacgg   7620
tgcggccttc ctggtcgatc agctcgcggg cgtgcgcgat ctgtgccggg gtgagggtag   7680
ggcgggggcc aaacttcacg cctcgggcct tggcggcctc gcgcccgctc cgggtgcggt   7740
cgatgattag ggaacgctcg aactcggcaa tgccggcgaa cacggtcaac accatgcggc   7800
cggccggcgt ggtggtgtcg gcccacggct ctgccaggct acgcaggccc gcgccggcct   7860
cctggatgcg ctcggcaatg tccagtaggt cgcgggtgct gcgggccagg cggtctagcc   7920
tggtcactgt cacaacgtcg ccagggcgta ggtggtcaag catcctggcc agctccgggc   7980
ggtcgcgcct ggtgccggtg atcttctcgg aaaacagctt ggtgcagccg gccgcgtgca   8040
gttcggcccg ttggttggtc aagtcctggt cgtcggtgct gacgcgggca tagcccagca   8100
ggccagcggc ggcgctcttg ttcatggcgt aatgtctccg gttctagtcg caagtattct   8160
actttatgcg actaaaacac gcgacaagaa aacgccagga aaagggcagg cggcagcct   8220 gtcgcgtaac ttaggacttg tgcgacatgt cgttttcaga agacggctgc actgaacgtc   8280
agaagccgac tgcactatag cagcggaggg gttggatcaa agtactttga tcccgagggg   8340
aaccctgtgg ttggcatgca catacaaatg gacgaacgga taaaccttt cacgcccttt   8400 taaatatccg ttattctaat aaacgctctt ttctcttagg tttacccgcc aatatatcct   8460
gtcaaacact gatagtttaa actgaaggcg ggaaacgaca atctgatcca agctcaagct   8520
gctctagcat tcgccattca ggctgcgcaa ctgttgggaa gggcgatcgg tgcggcctc   8580 ttcgctatta cgccagctgg cgaaaggggg atgtgctgca aggcgattaa gttgggtaac   8640
```

-continued

```
gccagggttt tcccagtcac gacgttgtaa aacgacggcc agtgccaagc ttcattcgga   8700
gtttttgtat cttgtttcat agtttgtccc aggattagaa tgattaggca tcgaaccttc   8760
aagaatttga ttgaataaaa catcttcatt cttaagatat gaagataatc ttcaaaaggc   8820
ccctgggaat ctgaaagaag agaagcaggc ccatttatat gggaaagaac aatagtattt   8880
cttatatagg cccatttaag ttgaaaacaa tcttcaaaag tcccacatcg cttagataag   8940
aaaacgaagc tgagtttata tacagctaga gtcgaagtag tgaccagtaa ctctcgtcga   9000
tcgtgtttta gagctagaaa tagcaagtta aaataaggct agtccgttat caacttgaaa   9060
aagtggcacc gagtcggtgc ttttttttgc gcacgaggta cgcctgagcg tctagatttg   9120
catgcctgca ggtcaacatg gtggagcacg acacacttgt ctactccaaa aatatcaaag   9180
atacagtctc agaagaccaa agggcaattg agacttttca acaagggta atatccggaa    9240 acctcctcgg attccattgc ccagctatct gtcactttat tgtgaagata gtggaaaagg   9300
aaggtggctc ctacaaatgc catcattgcg ataaaggaaa ggccatcgtt gaagatgcct   9360
ctgccgacag tggtcccaaa gatggacccc cacccacgag gagcatcgtg gaaaagaag    9420 acgttccaac cacgtcttca aagcaagtgg attgatgtga taacatggtg gagcacgaca   9480
cacttgtcta ctccaaaaat atcaaagata cagtctcaga agaccaaagg caattgaga    9540 cttttcaaca aagggtgata tccggaaacc tcctcggatt ccattgccca gctatctgtc   9600
actttattgt gaagatagtg gaaaggaag gtggctccta caaatgccat cattgcgata   9660
aaggaaaggc catcgttgaa gatgcctctg ccgacagtgg tcccaaagat ggaccccac    9720 ccacgaggag catcgtggaa aaagaagacg ttccaaccac gtcttcaaag caagtggatt   9780
gatgtgatat ctccactgac gtaagggatg acgcacaatc ccactatcct tcgcaagacc   9840
cttcctctat ataaggaagt tcatttcatt tggagaggac ctcgacctca acacaacata   9900
tacaaaacaa acgaatctca agcaatcaag cattctactt ctattgcagc aatttaaatc   9960 atttcttta aagcaaaagc aattttctga aaatttcac catttacgaa cgatactcga    10020
gatggactac aaggaccacg acggagatta caaagaccac gacattgatt acaaggatga   10080
tgacgacaag atggctccca agaagaagcg aaaggtgggc atccacggcg tgcccgctgc   10140
cgacaaaaag tatagtatcg gactggatat tggcactaac agcgtgggat gggccgtcat   10200
caccgacgag tacaaagtgc caagcaagaa gttcaaggtc ctgggaaaca ccgatagaca   10260
cagtatcaag aaaaatctga ttggagccct gctgttcgac tcaggggaga cagctgaagc   10320
aactaggctg aaaagaacag ctaggagacg gtatactcgc cgaaagaatc ggatctgcta   10380
cctccaggag attttctcca acgaaatggc caaggtggac gatagtttct ttcatcgcct   10440
ggaggaatca ttcctggtcg aggaagataa gaaacacgag aggcatccca tctttggcaa   10500
cattgtggac gaggtcgctt atcacgaaaa gtaccctaca atctatcatc tgcggaagaa   10560
actggtggac agcactgata aggcagacct gcgcctgatc tatctggccc tggctcacat   10620
gattaagttc aggggggcatt ttctgatcga gggcgatctg aacccagaca attccgatgt   10680
ggacaagctg ttcatccagc tggtccagac atacaatcag ctgtttgagg aaaaccccat   10740
taatgcatct ggggtggacg caaaagccat cctgagtgcc agactgtcta agagtaggag   10800
actggagaac ctgatcgctc agctgccagg cgaaaagaaa aacggcctgt ttggaaatct   10860
gattgcactg tcactgggac tgaccccaa cttcaagagc aatttgatc tggccgagga   10920 cgctaagctc cagctgagca aggacaccta cgacgatgac ctggataacc tgctggctca   10980
gatcggcgat cagtacgcag acctgttcct ggccgctaag aatctgtctg acgccatcct   11040
```

```
gctgagtgat attctgagag tgaacaccga gattacaaaa gcccccctgt cagctagcat    11100
gatcaagaga tatgacgagc accatcagga tctgaccctg ctgaaggctc tggtgcggca    11160
gcagctgcct gagaagtaca agaaatctt ctttgatcag agcaagaatg ggtacgccgg    11220
ctatattgac ggcggagctt cccaggagga gttctacaag tttatcaaac ctattctgga    11280
gaagatggac ggcactgagg aactgctggt gaaactgaat cgggaagacc tgctgcggaa    11340
gcagcgcacc ttcgataacg gcagcatccc tcaccagatt catctgggag agctgcacgc    11400
aatcctgcgg cgccaggaag acttctaccc atttctgaag gataaccggg agaagatcga    11460
aaaaattctg actttccgca tccctacta tgtgggcct ctggcaagag gcaattcccg    11520
gtttgcctgg atgacccgca agtctgagga acaatcact ccctggaact cgaggaagt    11580
ggtcgataag ggcgcttccg cacagtcttt cattgagagg atgacaaatt ttgacaagaa    11640
cctgccaaat gaaaaagtgc tgcccaagca cagcctgctg tacgagtatt tcaccgtcta    11700
taacgaactg acaaaggtga aatacgtcac tgagggcatg agaaagcctg ccttcctgtc    11760
cggagaacag aagaaagcta tcgtggacct gctgtttaaa accaatcgga aggtgacagt    11820
caagcagctg aaagaggact acttcaagaa aattgaatgt ttcgattctg tggagatcag    11880
tggggtcgaa gacaggttta cgcctctct gggcacctac cacgatctgc tgaagatcat    11940
taaggataaa gacttcctgg acaacgagga aaatgaggac atcctggagg acattgtgct    12000
gaccctgaca ctgtttgagg atcgggaaat gatcgaggaa cgcctgaaga cctacgccca    12060
tctgttcgat gacaaagtga tgaaacagct gaagcgaagg agatacactg ggtggggccg    12120
actgagcagg aagctgatca atggcattcg cgacaaacag agtggaaaga caatcctgga    12180
ctttctgaag tcagatggct tcgctaacag gaacttcatg cagctgattc acgatgactc    12240
tctgactttc aaagaggaca tccagaaggc acaggtgtcc ggacagggg actctctgca    12300
cgagcatatc gcaaacctgg ccgggagccc tgccatcaag aaaggcatcc tccagaccgt    12360
gaaggtggtg gacgagctgg tgaaagtcat gggaagacat aagccagaaa acatcgtgat    12420
tgagatggcc agggagaatc agaccacaca gaaaggcag aagaactctc gggagcgcat    12480
gaaacgcatc gaggaaggaa ttaaggaact ggggagtcag atcctgaaag cacccccgt    12540
ggaaaacaca cagctccaga tgagaagct gtatctgtac tacctccaga atggccgcga    12600
tatgtacgtg gaccaggagc tggatattaa ccgactgtca gattatgacg tggatcatat    12660
cgtcccacag tcattcctga agatgacag cattgacaat aaggtgctga cccgcagcga    12720
caaaaaccga ggaaagagtg ataatgtccc ctcagaggaa gtggtcaaga aaatgaagaa    12780
ctactggagg cagctgctga atgccaaact gatcacccag cgaaagtttg ataacctgac    12840
aaaagctgag aggggggcc tgtccgaact ggacaaagca ggcttcatca agcgacagct    12900
ggtggagaca aggcagatca caaagcacgt cgctcagatc ctggacagca ggatgaacac    12960
caagtacgat gagaatgaca aactgatccg ggaagtgaag gtcattacac tgaagtcaaa    13020
actggtgagc gactttagga agatttccca gttctacaag gtcagagaga tcaacaacta    13080
ccaccatgct catgacgcat acctgaacgc agtggtcggg actgccctga ttaagaaata    13140
ccctaaactg gagtctgagt tcgtgtacgg cgactataag gtgtacgatg tcagaaaaat    13200
gatcgccaag agcgagcagg aaattggcaa agccaccgct aagtatttct tttactccaa    13260
catcatgaat ttcttaaga ctgagatcac cctggcaaat ggcgaaatcc gaaagaggcc    13320
actgattgag actaacggag agacagggga atcgtgtgg gacaaggaa gagattttgc    13380
```

```
taccgtgcgg aaggtcctga gtatgcccca agtgaatatt gtcaagaaaa cagaggtgca    13440
gactggaggg ttcagtaagg aatcaattct gcctaaacgc aacagcgata agctgatcgc    13500
ccgaaagaaa gactgggacc ccaagaagta tggcggattc gactccccaa ccgtggctta    13560
ctctgtcctg gtggtcgcaa aggtggagaa gggaaaaagc aagaaactga aatccgtcaa    13620
ggaactgctg gggatcacaa ttatggagag gagcagcttc gaaaagaatc ctatcgattt    13680
tctggaggcc aaagggtata aggaagtgaa gaaagacctg atcatcaagc tgccaaagta    13740
ctctctgttt gagctggaaa acggcagaaa gcggatgctg gcaagtgccg gcgagctgca    13800
aaaaggaaat gaactggccc tgccctcaaa gtacgtgaac ttcctgtatc tggctagcca    13860
ctacgagaag ctgaaaggct cccctgagga taacgaacag aaacagctgt tgtggagca    13920 gcacaagcat tatctggacg agatcattga acagattagc gagttctcca acgcgtgat    13980 cctggctgac gcaaatctgg ataaggtcct gtctgcatac aacaaacaca gggacaagcc    14040
aatcagagag caggccgaaa atatcattca tctgttcact ctgaccaacc tgggagcccc    14100
cgcagccttc aagtattttg acactaccat cgatcgcaaa cgatacacaa gcactaagga    14160
ggtgctggat gctaccctga tccaccagag cattactggg ctgtacgaga caaggatcga    14220
cctgtcccag ctgggggag acaaacgccc agccgccacc aagaaagcag acaggcaaa    14280 gaagaagaag tgagagctct gattgatcga tagagctcga atttccccga tcgttcaaac    14340
atttggcaat aaagtttctt aagattgaat cctgttgccg tcttgcgat gattatcata    14400 taatttctgt tgaattacgt taagcatgta ataattaaca tgtaatgcat gacgttattt    14460
atgagatggg tttttatgat tagagtcccg caattataca tttaatacgc gatagaaaac    14520
aaaatatagc gcgcaaacta ggataaatta tcgcgcgcgg tgtcatctat gttactagat    14580
cggggatccg aattc                                                   14595

<210> SEQ ID NO 22
<211> LENGTH: 23
<212> TYPE: DNA
<213> ORGANISM: Artificial Sequence
<220> FEATURE:
<223> OTHER INFORMATION: Ob2MYB14 guide

<400> SEQUENCE: 22
gaccagtaac tctcgtcgat cgt                                             23

<210> SEQ ID NO 23
<211> LENGTH: 30
<212> TYPE: DNA
<213> ORGANISM: Artificial Sequence
<220> FEATURE:
<223> OTHER INFORMATION: primer

<400> SEQUENCE: 23
ggtctagaat ggccgccgtc tgcctgaagc                                      30

<210> SEQ ID NO 24
<211> LENGTH: 29
<212> TYPE: DNA
<213> ORGANISM: Artificial Sequence
<220> FEATURE:
<223> OTHER INFORMATION: primer

<400> SEQUENCE: 24
gggagctctc atctgggaac actgctgac                                       29
```

```
<210> SEQ ID NO 25
<211> LENGTH: 25
<212> TYPE: DNA
<213> ORGANISM: Artificial Sequence
<220> FEATURE:
<223> OTHER INFORMATION: primer

<400> SEQUENCE: 25
aagcttcatt cggagttttt gtatc                                         25

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
ggaaatggaa acttcgccgg                                               20

<210> SEQ ID NO 27
<211> LENGTH: 30
<212> TYPE: DNA
<213> ORGANISM: Artificial Sequence
<220> FEATURE:
<223> OTHER INFORMATION: primer

<400> SEQUENCE: 27
ggtctagaat ggccgccgtc tgcctgaagc                                    30

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
ggaaatggaa acttcgccgg                                               20

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
cggctgaaca ggcgctgatt g                                             21

<210> SEQ ID NO 30
<211> LENGTH: 25
<212> TYPE: DNA
<213> ORGANISM: Artificial Sequence
<220> FEATURE:
<223> OTHER INFORMATION: primer

<400> SEQUENCE: 30
caacatacga ctacggttca tcaag                                         25

<210> SEQ ID NO 31
<211> LENGTH: 21
<212> TYPE: DNA
<213> ORGANISM: Artificial Sequence
<220> FEATURE:
<223> OTHER INFORMATION: primer
```

```
<400> SEQUENCE: 31
ccattccctc gcctgcattt c                                              21

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
gctgggatcc gcgcgatgtg                                                20

<210> SEQ ID NO 33
<211> LENGTH: 63
<212> TYPE: DNA
<213> ORGANISM: Ocimum basilicum

<400> SEQUENCE: 33
tcaaatcttt cgcccccgcc accgtcgcca acttgggccc aggcttcgac tttctgggat    60
gcg                                                                  63

<210> SEQ ID NO 34
<211> LENGTH: 62
<212> TYPE: DNA
<213> ORGANISM: Artificial Sequence
<220> FEATURE:
<223> OTHER INFORMATION: portion of mutant ObHSK sequence

<400> SEQUENCE: 34
tcaaatcttt cgcccccgcc accgtcgcca acttgggcca ggcttcgact ttctgggatg    60
cg                                                                   62

<210> SEQ ID NO 35
<211> LENGTH: 50
<212> TYPE: DNA
<213> ORGANISM: Artificial Sequence
<220> FEATURE:
<223> OTHER INFORMATION: portion of mutant ObHSK sequence

<400> SEQUENCE: 35
tcaaatcttt cgcccccgcc accgtcgcca acttgggttt ctgggatgcg               50

<210> SEQ ID NO 36
<211> LENGTH: 72
<212> TYPE: DNA
<213> ORGANISM: Artificial Sequence
<220> FEATURE:
<223> OTHER INFORMATION: portion of mutant ObHSK sequence
<220> FEATURE:
<221> NAME/KEY: misc_feature
<222> LOCATION: (41)..(46)
<223> OTHER INFORMATION: n is a, c, g, or t

<400> SEQUENCE: 36
tcaaatcttt cgcccccgcc accgtcgcca acttgggccc nnnnnnccca ggcttcgact    60
ttctgggatg cg                                                        72

<210> SEQ ID NO 37
<211> LENGTH: 81
<212> TYPE: DNA
<213> ORGANISM: Artificial Sequence
<220> FEATURE:
<223> OTHER INFORMATION: portion of mutant ObHSK sequence
```

```
<220> FEATURE:
<221> NAME/KEY: misc_feature
<222> LOCATION: (41)..(55)
<223> OTHER INFORMATION: n is a, c, g, or t

<400> SEQUENCE: 37 tcaaatctttt cgcccccgcc accgtcgcca acttgggccc nnnnnnnnnn nnnnncccag    60
gcttcgactt tctgggatgc g                                               81

<210> SEQ ID NO 38
<211> LENGTH: 62
<212> TYPE: DNA
<213> ORGANISM: Artificial Sequence
<220> FEATURE:
<223> OTHER INFORMATION: portion of mutant ObHSK sequence

<400> SEQUENCE: 38 tcaaatctttt cgcccccgcc accgtcgcca acttgggcca ggcttcgact ttctgggatg    60
cg                                                                    62

<210> SEQ ID NO 39
<211> LENGTH: 61
<212> TYPE: DNA
<213> ORGANISM: Artificial Sequence
<220> FEATURE:
<223> OTHER INFORMATION: portion of mutant ObHSK sequence

<400> SEQUENCE: 39 tcaaatctttt cgcccccgcc accgtcgcca acttgggcag gcttcgactt tctgggatgc    60
g                                                                     61

<210> SEQ ID NO 40
<211> LENGTH: 53
<212> TYPE: DNA
<213> ORGANISM: Artificial Sequence
<220> FEATURE:
<223> OTHER INFORMATION: portion of mutant ObHSK sequence

<400> SEQUENCE: 40 tcaaatctttt cgcccccgcc accgtcgcca aggcttcgac tttctgggat gcg           53

<210> SEQ ID NO 41
<211> LENGTH: 50
<212> TYPE: DNA
<213> ORGANISM: Artificial Sequence
<220> FEATURE:
<223> OTHER INFORMATION: portion of mutant ObHSK sequence

<400> SEQUENCE: 41 tcaaatctttt cgcccccgcc accgtcgcca acttgggttt ctgggatgcg               50

<210> SEQ ID NO 42
<211> LENGTH: 39
<212> TYPE: DNA
<213> ORGANISM: Artificial Sequence
<220> FEATURE:
<223> OTHER INFORMATION: portion of mutant ObHSK sequence

<400> SEQUENCE: 42 tcaaatctttt cgcccccgcc accgtctttc tgggatgcg                           39

<210> SEQ ID NO 43
<211> LENGTH: 69
<212> TYPE: DNA
```

```
<213> ORGANISM: Artificial Sequence
<220> FEATURE:
<223> OTHER INFORMATION: portion of mutant ObHSK sequence
<220> FEATURE:
<221> NAME/KEY: misc_feature
<222> LOCATION: (38)..(43)
<223> OTHER INFORMATION: n is a, c, g, or t

<400> SEQUENCE: 43 tcaaatctttt cgcccccgcc accgtcgcca acttgggnnn nnncccaggc ttcgactttc    60
tgggatgcg                                                             69

<210> SEQ ID NO 44
<211> LENGTH: 78
<212> TYPE: DNA
<213> ORGANISM: Artificial Sequence
<220> FEATURE:
<223> OTHER INFORMATION: portion of mutant ObHSK sequence
<220> FEATURE:
<221> NAME/KEY: misc_feature
<222> LOCATION: (38)..(52)
<223> OTHER INFORMATION: n is a, c, g, or t

<400> SEQUENCE: 44 tcaaatctttt cgcccccgcc accgtcgcca acttgggnnn nnnnnnnnn nncccaggct    60 tcgactttct gggatgcg                                                   78

<210> SEQ ID NO 45
<211> LENGTH: 62
<212> TYPE: DNA
<213> ORGANISM: Artificial Sequence
<220> FEATURE:
<223> OTHER INFORMATION: portion of mutant ObHSK sequence

<400> SEQUENCE: 45 tcaaatctttt cgcccccgcc accgtcgcca acttgggcca ggcttcgact ttctgggatg    60
cg                                                                    62

<210> SEQ ID NO 46
<211> LENGTH: 50
<212> TYPE: DNA
<213> ORGANISM: Artificial Sequence
<220> FEATURE:
<223> OTHER INFORMATION: portion of mutant ObHSK sequence

<400> SEQUENCE: 46 tcaaatctttt cgcccccgcc accgtcgcca acttgggttt ctgggatgcg                50

<210> SEQ ID NO 47
<211> LENGTH: 69
<212> TYPE: DNA
<213> ORGANISM: Artificial Sequence
<220> FEATURE:
<223> OTHER INFORMATION: portion of mutant ObHSK sequence
<220> FEATURE:
<221> NAME/KEY: misc_feature
<222> LOCATION: (38)..(43)
<223> OTHER INFORMATION: n is a, c, g, or t

<400> SEQUENCE: 47 tcaaatctttt cgcccccgcc accgtcgcca acttgggnnn nnncccaggc ttcgactttc    60
tgggatgcg                                                             69

<210> SEQ ID NO 48
<211> LENGTH: 78
```

<212> TYPE: DNA
<213> ORGANISM: Artificial Sequence
<220> FEATURE:
<223> OTHER INFORMATION: portion of mutant ObHSK sequence
<220> FEATURE:
<221> NAME/KEY: misc_feature
<222> LOCATION: (38)..(52)
<223> OTHER INFORMATION: n is a, c, g, or t

<400> SEQUENCE: 48
tcaaatcttt cgcccccgcc accgtcgcca acttgggnnn nnnnnnnnn nncccaggct    60 tcgactttct gggatgcg                                                 78

<210> SEQ ID NO 49
<211> LENGTH: 48
<212> TYPE: DNA
<213> ORGANISM: Artificial Sequence
<220> FEATURE:
<223> OTHER INFORMATION: portion of mutant ObHSK sequence

<400> SEQUENCE: 49
tcaaatcttt cgcccccgcc accgtcgcca acttgggtct gggatgcg                48

<210> SEQ ID NO 50
<211> LENGTH: 44
<212> TYPE: DNA
<213> ORGANISM: Artificial Sequence
<220> FEATURE:
<223> OTHER INFORMATION: portion of mutant ObHSK sequence

<400> SEQUENCE: 50
tcaaatcttt cgcccccgcc accgtcgcca acttctggga tgcg                    44

<210> SEQ ID NO 51
<211> LENGTH: 75
<212> TYPE: DNA
<213> ORGANISM: Artificial Sequence
<220> FEATURE:
<223> OTHER INFORMATION: portion of mutant ObHSK sequence
<220> FEATURE:
<221> NAME/KEY: misc_feature
<222> LOCATION: (49)..(49)
<223> OTHER INFORMATION: n is a, c, g, or t

<400> SEQUENCE: 51
tctgggatgc gtcaaatctt tcgccccgc caccgtcgcc aacttgggnc ccaggcttcg    60
actttctggg atgcg                                                    75

<210> SEQ ID NO 52
<211> LENGTH: 62
<212> TYPE: DNA
<213> ORGANISM: Artificial Sequence
<220> FEATURE:
<223> OTHER INFORMATION: portion of mutant ObHSK sequence

<400> SEQUENCE: 52
tcaaatcttt cgcccccgcc accgtcgcca acttgggcca ggcttcgact ttctgggatg    60
cg                                                                  62

<210> SEQ ID NO 53
<211> LENGTH: 50
<212> TYPE: DNA
<213> ORGANISM: Artificial Sequence
<220> FEATURE:
<223> OTHER INFORMATION: portion of mutant ObHSK sequence

```
<400> SEQUENCE: 53
tcaaatcttt cgcccccgcc accgtcgcca acttgggttt ctgggatgcg              50

<210> SEQ ID NO 54
<211> LENGTH: 47
<212> TYPE: DNA
<213> ORGANISM: Artificial Sequence
<220> FEATURE:
<223> OTHER INFORMATION: portion of mutant ObHSK sequence

<400> SEQUENCE: 54
tcaaatcttt cgcccccgcc acccaggctt cgactttctg ggatgcg                 47

<210> SEQ ID NO 55
<211> LENGTH: 69
<212> TYPE: DNA
<213> ORGANISM: Artificial Sequence
<220> FEATURE:
<223> OTHER INFORMATION: portion of mutant ObHSK sequence
<220> FEATURE:
<221> NAME/KEY: misc_feature
<222> LOCATION: (38)..(43)
<223> OTHER INFORMATION: n is a, c, g, or t

<400> SEQUENCE: 55
tcaaatcttt cgcccccgcc accgtcgcca acttgggnnn nnncccaggc ttcgactttc   60
tgggatgcg                                                           69

<210> SEQ ID NO 56
<211> LENGTH: 78
<212> TYPE: DNA
<213> ORGANISM: Artificial Sequence
<220> FEATURE:
<223> OTHER INFORMATION: portion of mutant ObHSK sequence
<220> FEATURE:
<221> NAME/KEY: misc_feature
<222> LOCATION: (38)..(52)
<223> OTHER INFORMATION: n is a, c, g, or t

<400> SEQUENCE: 56
tcaaatcttt cgcccccgcc accgtcgcca acttgggnnn nnnnnnnnnn nncccaggct   60
tcgactttct gggatgcg                                                 78

<210> SEQ ID NO 57
<211> LENGTH: 62
<212> TYPE: DNA
<213> ORGANISM: Artificial Sequence
<220> FEATURE:
<223> OTHER INFORMATION: portion of mutant ObHSK sequence

<400> SEQUENCE: 57
tcaaatcttt cgcccccgcc accgtcgcca acttgggcca ggcttcgact ttctgggatg   60
cg                                                                  62

<210> SEQ ID NO 58
<211> LENGTH: 53
<212> TYPE: DNA
<213> ORGANISM: Artificial Sequence
<220> FEATURE:
<223> OTHER INFORMATION: portion of mutant ObHSK sequence

<400> SEQUENCE: 58
tcaaatcttt cgcccccgcc accgtcgcca aggcttcgac tttctgggat gcg           53
```

```
<210> SEQ ID NO 59
<211> LENGTH: 50
<212> TYPE: DNA
<213> ORGANISM: Artificial Sequence
<220> FEATURE:
<223> OTHER INFORMATION: portion of mutant ObHSK sequence

<400> SEQUENCE: 59 tcaaatctttt cgcccccgcc accgcccagg cttcgactttt ctgggatgcg          50

<210> SEQ ID NO 60
<211> LENGTH: 39
<212> TYPE: DNA
<213> ORGANISM: Artificial Sequence
<220> FEATURE:
<223> OTHER INFORMATION: portion of mutant ObHSK sequence

<400> SEQUENCE: 60 tcaaatctttt cgcccccgcc accgtctttc tgggatgcg                       39

<210> SEQ ID NO 61
<211> LENGTH: 69
<212> TYPE: DNA
<213> ORGANISM: Artificial Sequence
<220> FEATURE:
<223> OTHER INFORMATION: portion of mutant ObHSK sequence
<220> FEATURE:
<221> NAME/KEY: misc_feature
<222> LOCATION: (38)..(43)
<223> OTHER INFORMATION: n is a, c, g, or t

<400> SEQUENCE: 61 tcaaatctttt cgcccccgcc accgtcgcca acttgggnnn nnncccaggc ttcgactttc  60
tgggatgcg                                                          69

<210> SEQ ID NO 62
<211> LENGTH: 78
<212> TYPE: DNA
<213> ORGANISM: Artificial Sequence
<220> FEATURE:
<223> OTHER INFORMATION: portion of mutant ObHSK sequence
<220> FEATURE:
<221> NAME/KEY: misc_feature
<222> LOCATION: (38)..(52)
<223> OTHER INFORMATION: n is a, c, g, or t

<400> SEQUENCE: 62 tcaaatctttt cgcccccgcc accgtcgcca acttgggnnn nnnnnnnnn nncccaggct   60 tcgactttct gggatgcg                                                78

<210> SEQ ID NO 63
<211> LENGTH: 62
<212> TYPE: DNA
<213> ORGANISM: Artificial Sequence
<220> FEATURE:
<223> OTHER INFORMATION: portion of mutant ObHSK sequence

<400> SEQUENCE: 63 tcaaatctttt cgcccccgcc accgtcgcca acttgggcca ggcttcgact ttctgggatg  60
cg                                                                 62

<210> SEQ ID NO 64
<211> LENGTH: 53
<212> TYPE: DNA
<213> ORGANISM: Artificial Sequence
<220> FEATURE:
```

<223> OTHER INFORMATION: portion of mutant ObHSK sequence

<400> SEQUENCE: 64 tcaaatctttt cgcccccgcc accgtcgcca aggcttcgac tttctgggat gcg    53

<210> SEQ ID NO 65
<211> LENGTH: 50
<212> TYPE: DNA
<213> ORGANISM: Artificial Sequence
<220> FEATURE:
<223> OTHER INFORMATION: portion of mutant ObHSK sequence

<400> SEQUENCE: 65 tcaaatctttt cgcccccgcc accgcccagg cttcgacttt ctgggatgcg    50

<210> SEQ ID NO 66
<211> LENGTH: 39
<212> TYPE: DNA
<213> ORGANISM: Artificial Sequence
<220> FEATURE:
<223> OTHER INFORMATION: portion of mutant ObHSK sequence

<400> SEQUENCE: 66 tcaaatctttt cgcccccgcc accgtctttc tgggatgcg    39

<210> SEQ ID NO 67
<211> LENGTH: 62
<212> TYPE: DNA
<213> ORGANISM: Artificial Sequence
<220> FEATURE:
<223> OTHER INFORMATION: portion of mutant ObHSK sequence

<400> SEQUENCE: 67 tcaaatctttt cgcccccgcc accgtcgcca acttgggcca ggcttcgact ttctgggatg    60
cg    62

<210> SEQ ID NO 68
<211> LENGTH: 53
<212> TYPE: DNA
<213> ORGANISM: Artificial Sequence
<220> FEATURE:
<223> OTHER INFORMATION: portion of mutant ObHSK sequence

<400> SEQUENCE: 68 tcaaatctttt cgcccccgcc accgtcgcca aggcttcgac tttctgggat gcg    53

<210> SEQ ID NO 69
<211> LENGTH: 50
<212> TYPE: DNA
<213> ORGANISM: Artificial Sequence
<220> FEATURE:
<223> OTHER INFORMATION: portion of mutant ObHSK sequence

<400> SEQUENCE: 69 tcaaatctttt cgcccccgcc accgtcgcca acttgggttt ctgggatgcg    50

<210> SEQ ID NO 70
<211> LENGTH: 69
<212> TYPE: DNA
<213> ORGANISM: Artificial Sequence
<220> FEATURE:
<223> OTHER INFORMATION: portion of mutant ObHSK sequence
<220> FEATURE:
<221> NAME/KEY: misc_feature
<222> LOCATION: (38)..(43)
<223> OTHER INFORMATION: n is a, c, g, or t

<400> SEQUENCE: 70 tcaaatctttt cgcccccgcc accgtcgcca acttgggnnn nnnccaggc ttcgactttc        60 tgggatgcg        69

<210> SEQ ID NO 71
<211> LENGTH: 78
<212> TYPE: DNA
<213> ORGANISM: Artificial Sequence
<220> FEATURE:
<223> OTHER INFORMATION: portion of mutant ObHSK sequence
<220> FEATURE:
<221> NAME/KEY: misc_feature
<222> LOCATION: (38)..(52)
<223> OTHER INFORMATION: n is a, c, g, or t

<400> SEQUENCE: 71 tcaaatctttt cgcccccgcc accgtcgcca acttgggnnn nnnnnnnnn nncccaggct        60 tcgactttct gggatgcg        78

<210> SEQ ID NO 72
<211> LENGTH: 44
<212> TYPE: DNA
<213> ORGANISM: Ocimum basilicum

<400> SEQUENCE: 72
tccgtcaaat ctttcgcccc cgccaccgtc gccaacttgg ccca        44

<210> SEQ ID NO 73
<211> LENGTH: 45
<212> TYPE: DNA
<213> ORGANISM: Ocimum basilicum

<400> SEQUENCE: 73
tccgtcaaat ctttcgcccc cgccaccgtc gccaacttgg gccct        45

<210> SEQ ID NO 74
<211> LENGTH: 43
<212> TYPE: DNA
<213> ORGANISM: Ocimum basilicum

<400> SEQUENCE: 74
atggccgccg tctgtgaagc tcaatttcgc cgccgccgcc gcc        43

<210> SEQ ID NO 75
<211> LENGTH: 45
<212> TYPE: DNA
<213> ORGANISM: Ocimum basilicum

<400> SEQUENCE: 75
atggccgccg tctgcctgaa gctcaatttc gccgccgccg ccgcc        45

<210> SEQ ID NO 76
<211> LENGTH: 55
<212> TYPE: DNA
<213> ORGANISM: Ocimum basilicum

<400> SEQUENCE: 76
gaagcctggg ccaagttggc gacggtggcg ggggcgaaag atttgacgga atgag        55

<210> SEQ ID NO 77
<211> LENGTH: 54
<212> TYPE: DNA

```
<213> ORGANISM: Ocimum basilicum

<400> SEQUENCE: 77
ggcggcggcg gcggcggcga aattgagctt cacagacggc ggccattcta gacc        54

<210> SEQ ID NO 78
<211> LENGTH: 23
<212> TYPE: DNA
<213> ORGANISM: Ocimum basilicum

<400> SEQUENCE: 78 ttcgccccg ccaccgtcgc caa                                           23

<210> SEQ ID NO 79
<211> LENGTH: 24
<212> TYPE: DNA
<213> ORGANISM: Ocimum basilicum

<400> SEQUENCE: 79
tttcgccccc gccaccgtcg ccaa                                         24

<210> SEQ ID NO 80
<211> LENGTH: 31
<212> TYPE: DNA
<213> ORGANISM: Ocimum basilicum

<400> SEQUENCE: 80
ccccgccacc gtcgccaact tgggccctgg c                                 31

<210> SEQ ID NO 81
<211> LENGTH: 31
<212> TYPE: DNA
<213> ORGANISM: Ocimum basilicum

<400> SEQUENCE: 81
ccctttcacc gccgccaact tgggcccagg g                                 31

<210> SEQ ID NO 82
<211> LENGTH: 31
<212> TYPE: DNA
<213> ORGANISM: Ocimum basilicum

<400> SEQUENCE: 82 cccccttcacc gccgccaact tgggcccagg g                                31
```